US011203643B2

(12) United States Patent
Wang et al.

(10) Patent No.: US 11,203,643 B2
(45) Date of Patent: Dec. 21, 2021

(54) HUMANIZED ANTI-CD137 ANTIBODIES AND USES THEREOF

(71) Applicant: LYVGEN BIOPHARMA HOLDINGS LIMITED, Grand Cayman (KY)

(72) Inventors: Jieyi Wang, Belmont, CA (US); Yi Wu, Shanghai (CN)

(73) Assignee: LYVGEN BIOPHARMA HOLDINGS LIMITED, Grand Cayman (KY)

( * ) Notice: Subject to any disclaimer, the term of this patent is extended or adjusted under 35 U.S.C. 154(b) by 0 days.

(21) Appl. No.: 17/206,730

(22) Filed: Mar. 19, 2021

(65) Prior Publication Data
US 2021/0246218 A1 Aug. 12, 2021

Related U.S. Application Data

(63) Continuation of application No. PCT/US2020/032095, filed on May 8, 2020.

(30) Foreign Application Priority Data

May 10, 2019 (WO) .............. PCT/CN2019/086364

(51) Int. Cl.
C07K 16/28 (2006.01)
A61K 39/395 (2006.01)
A61P 35/00 (2006.01)
A61K 39/00 (2006.01)

(52) U.S. Cl.
CPC .... C07K 16/2878 (2013.01); *A61K 2039/505* (2013.01); *A61K 2039/507* (2013.01); *A61P 35/00* (2018.01); *C07K 16/2818* (2013.01); *C07K 2317/24* (2013.01); *C07K 2317/71* (2013.01); *C07K 2317/72* (2013.01); *C07K 2317/92* (2013.01)

(58) Field of Classification Search
None
See application file for complete search history.

(56) References Cited

U.S. PATENT DOCUMENTS 6,458,934 B1 * 10/2002 Hong ................ C07K 16/2878
530/387.3
6,569,997 B1 5/2003 Kwon
2003/0223989 A1 12/2003 Pluenneke et al.
2008/0286290 A1 11/2008 Furusako et al.
(Continued)

FOREIGN PATENT DOCUMENTS

WO WO 2003/049755 A1 6/2003
WO WO 2005/120568 A1 12/2005
(Continued)

OTHER PUBLICATIONS

U.S. Appl. No. 17/280,426, filed Mar. 26, 2021, Wang et al.
(Continued)

*Primary Examiner* — Claire Kaufman
(74) *Attorney, Agent, or Firm* — McDermott Will & Emery LLP

(57) ABSTRACT

Disclosed herein are humanized anti-CD137 antibodies and methods of using such for eliciting CD137 signaling, thereby enhancing immune responses such as T cell functions. The antibodies disclosed within may be used to treat diseases, such as cancer and immune disorders.

17 Claims, 18 Drawing Sheets
Specification includes a Sequence Listing.

(56) References Cited

U.S. PATENT DOCUMENTS

| | | |
|---|---|---|
| 2009/0304718 A1 | 12/2009 | Adolf et al. |
| 2010/0183621 A1 | 7/2010 | Jure-Kunkel et al. |
| 2014/0127225 A1 | 5/2014 | Basi et al. |
| 2016/0272708 A1 | 9/2016 | Chen |
| 2017/0247455 A1 | 8/2017 | Jure-Kunkel et al. |
| 2018/0237495 A1 | 8/2018 | Gieffers et al. |
| 2020/0385479 A1* | 12/2020 | Wang .................... C07K 16/28 |

FOREIGN PATENT DOCUMENTS

| | | |
|---|---|---|
| WO | WO 2012/032433 A1 | 3/2012 |
| WO | WO 2015/179236 A1 | 11/2015 |
| WO | WO 2017/087599 A1 | 5/2017 |
| WO | WO 2017/205745 A1 | 11/2017 |
| WO | WO 2019/113039 A1 | 6/2019 |

OTHER PUBLICATIONS

U.S. Appl. No. 16/769,463, filed Jun. 3, 2020, Wang et al.

[No Author Listed], CD137 [Macaca fascicularis]. GenBank Accession No. ABY47575.1. Published Dec. 5, 2008, 2 pages.

Chin et al., Structure of the 4-1BB/4-1BBL complex and distinct binding and functional properties of utomilumab and urelumab. Nat Commun. Nov. 8, 2018;9(1):4679.

Li et al., Immunotherapy of melanoma with the immune costimulatory monoclonal antibodies targeting CD137, Clin Pharmacol. Sep. 2, 2013;5(Suppl 1):47-53.

Lin et al., Fc-dependent expression of CD 137 on human NK cells: insights into "agonistic" effects of anti-CD137 monoclonal antibodies. Blood. Aug. 1, 2008;112(3):699-707, Epub Jun. 2, 2008.

\* cited by examiner

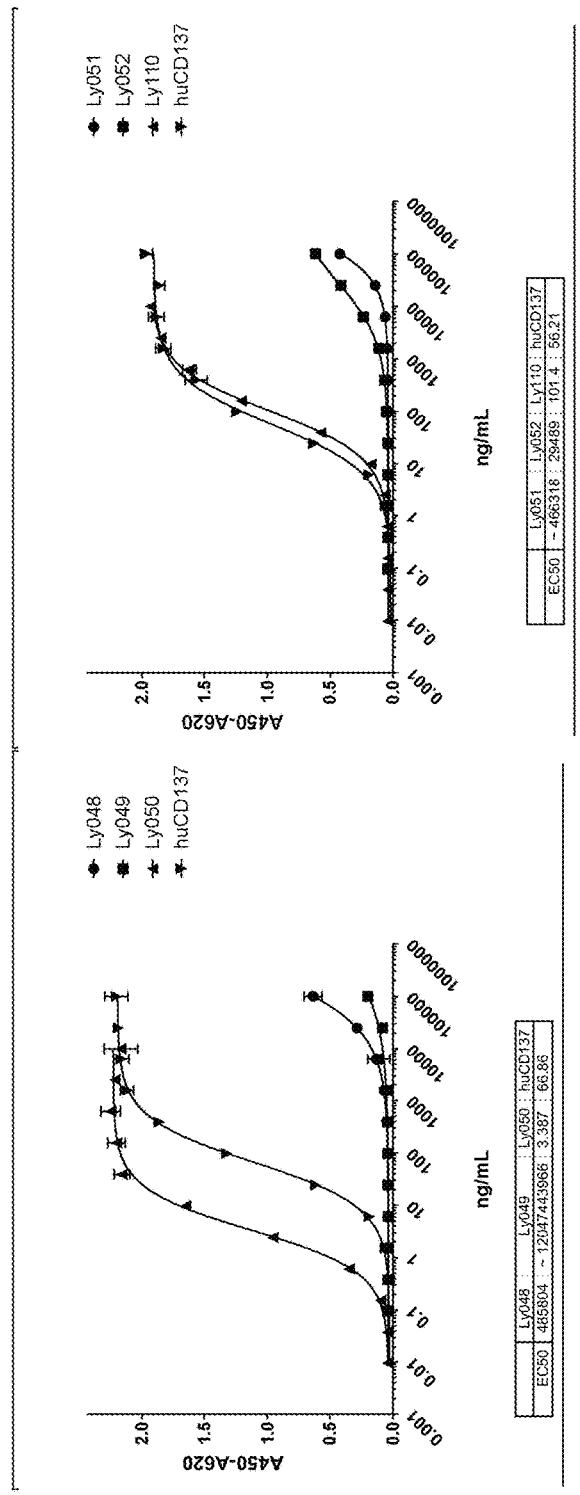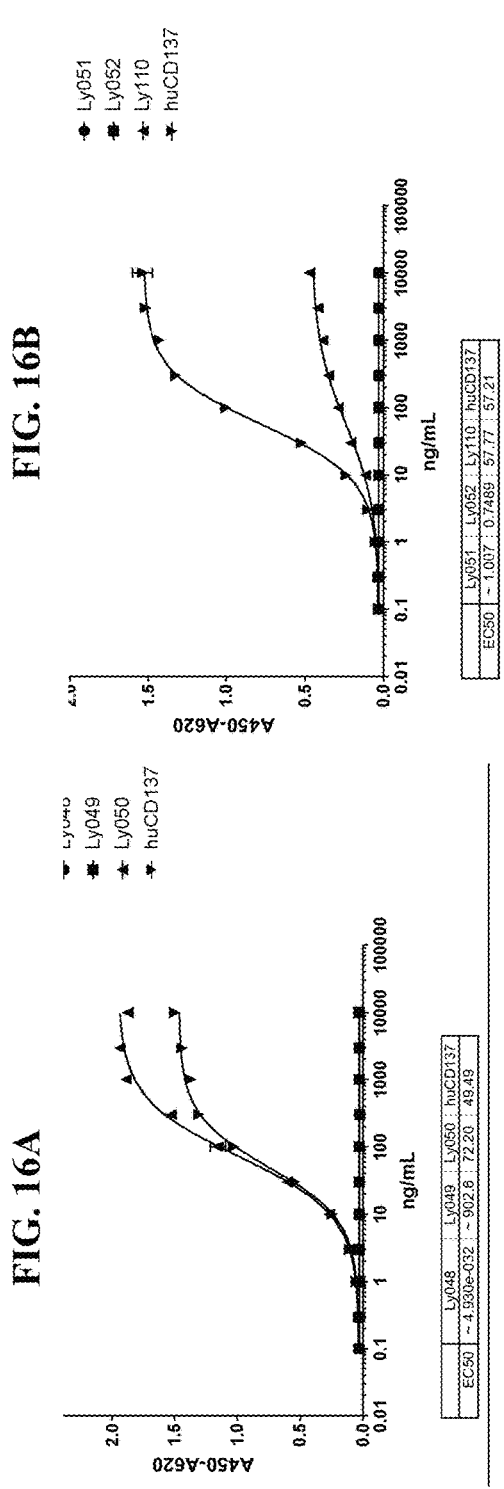
FIG. 16A  FIG. 16B  FIG. 16C  FIG. 16D

US 11,203,643 B2

HUMANIZED ANTI-CD137 ANTIBODIES AND USES THEREOF

RELATED APPLICATION

This application is a Continuation of International Patent Application No. PCT/US2020/03 2095, filed May 8, 2020, which claims the benefit of International Patent Application No. PCT/CN2019/086364, filed on May 10, 2019, each of which is incorporated by reference herein in its entirety.

SEQUENCE LISTING

The application contains a Sequence Listing that has been filed electronically in the form of a text file, created Mar. 18, 2021, and named "112238-0068-70007US00_SEQ.TXT" (29,000 bytes), the contents of which are incorporated by reference herein in their entirety.

BACKGROUND OF INVENTION

CD137, also known as 4-1BB or tumor necrosis factor receptor subfamily 9 (TNFRSF9), is a member of the tumor necrosis factor (TNF) receptor family It is expressed by activated T cells (more prevalently by $CD8^+$ than $CD4^+$), as well as dendritic cells, B cells, follicular dendritic cells, natural killer cells, granulocytes, and in the cells of blood vessel walls at sites of inflammation.

CD137 is a co-stimulator receptor for activated T cells and the crosslinking of CD137 enhances T cell proliferation, IL-2 secretion, survival, and cytolytic activity. CD137 can also induce proliferation in peripheral monocytes, enhance T cell apoptosis induced by TCR/CD3-triggered activation and regulated CD28 co-stimulation, resulting in the promotion of Th1 cell responses. Its expression is induced by lymphocyte activation, and TNF receptor associated factor (TRAF) adaptor proteins, in addition to CD ligand (CD137L) have been found to bind to the receptor, leading to the transduction of signals activating NF-κB.

Both antagonistic and agonistic antibodies specific to CD137 have been developed. U.S. Pat. Nos. 6,569,997, 8,137,667, and Fisher et al., Cancer Immunol Immunother (2012) 61:1721-1733. Agonist antibodies specific to CD137 have been reported to enhance T-cell function and promote anti-tumor activity. Fisher et al., Cancer Immunol Immunother (2012) 61:1721-1733. On the other hand, agonist antibodies specific to CD137 have also been reported to induce significant liver toxicity in patients. Segal et al., Clin Can Res., 2017, 23: 1929-1936.

It is therefore of interest to develop effective and safe CD137 agonists for therapeutic applications.

SUMMARY OF INVENTION

The present disclosure is based, at least in part, on the development of superior humanized anti-CD137 antibodies, which optionally may be full-length antibodies comprising a Fc variant having modified binding activity to one or more Fc receptors. Such humanized anti-CD137 antibodies have demonstrated for possessing various superior features as reported in the Examples below.

Accordingly, one aspect of the present disclosure provides an humanized antibody that binds CD137. Such an antibody may comprise (i) a heavy chain variable domain ($V_H$), and (ii) a light chain variable domain ($V_L$). The $V_H$ comprises the same heavy chain complementary determining regions (CDRs) 1-3 as reference antibody 371, the heavy chain CDRs being grafted in a human IGHV1-2*2 framework. The $V_L$ comprises the same light chain CDRs 1-3 as reference antibody 371, the light chain CDRs being grafted in a human IGKV1-39*01 framework.

In some embodiments, the humanized anti-CD137 antibody may comprise a heavy chain CDR1 (HC CDR1) comprising the amino acid sequence of SEQ ID NO: 12, a HC CDR2 comprising the amino acid sequence of SEQ ID NO: 14, a HC CDR3 comprising the amino acid sequence of SEQ ID NO: 16. Alternatively or in addition, the humanized anti-CD137 antibody may comprise a light chain CDR1 (LC CDR1) comprising the amino acid sequence of SEQ ID NO:29, a LC CDR2 comprising the amino acid sequence of SEQ ID NO: 31, and a LC CDR3 comprising the amino acid sequence of SEQ ID NO: 33.

In some embodiments, the humanized anti-CD137 antibody disclosed herein may comprise a heavy chain framework region 1 (HC FR1) comprising the amino acid sequence of SEQ ID NO: 18 or a variant thereof having no more than three back mutations, a HC FR2 comprising the amino acid sequence of SEQ ID NO: 19 or a variant thereof having no more than three back mutations, a HC FR3 comprising the amino acid sequence of SEQ ID NO: 20 or a variant thereof having no more than three back mutations, and/or a HC FR4 comprising the amino acid sequence of SEQ ID NO: 21 or a variant thereof having no more than three back mutations.

Alternatively or in addition, the humanized anti-CD137 antibody disclosed herein may comprise a light chain framework region 1 (LC FR1) comprising the amino acid sequence of SEQ ID NO: 35 or a variant thereof having no more than three back mutations, a LC FR2 comprising the amino acid sequence of SEQ ID NO: 36 or a variant thereof having no more than three back mutations, a LC FR3 comprising the amino acid sequence of SEQ ID NO: 37 or a variant thereof having no more than three back mutations, and/or a LC FR4 comprising the amino acid sequence of SEQ ID NO: 38 or a variant thereof having no more than three back mutations.

In some examples, the humanized anti-CD137 antibody may a humanized light chain variable region comprising one or more back mutations at positions K42 (e.g., K42G), P44 (e.g., P44V), F71 (e.g., F71Y), Y87 (e.g., Y87F), and V104 (e.g., V104L) in SEQ ID NO:4. In one example, the humanized antibody comprises a LC FR1 comprising the amino acid sequence of SEQ ID NO: 35, a LC FR2 comprising the amino acid sequence of SEQ ID NO: 36 or SEQ ID NO: 39, a LC FR3 comprising the sequence selected from SEQ ID NO: 37 and SEQ ID NO: 40, and/or a LC FR4 comprising the sequence of SEQ ID NO: 38 or SEQ ID NO:41. In specific examples, the humanized antibody of claim 4 comprises a LC FR1 comprising the sequence of SEQ ID NO: 35, a LC FR2 comprising the sequence of SEQ ID NO: 39, a LC FR3 comprising the sequence of SEQ ID NO: 40, and a LC FR4 comprising the sequence of SEQ ID NO: 38.

In some examples, the humanized anti-CD137 antibody disclosed herein may comprise a VH comprising the amino acid sequence of SEQ ID NO: 3, 8, or 9; and/or a VL comprise comprising the amino acid sequence of SEQ ID NO: 4, 5, or 10. In specific examples, the humanized antibody may comprise a VH comprising the amino acid sequence of SEQ ID NO:3 and a VL comprising the amino acid sequence of SEQ ID NO: 5.

In some embodiments, the humanized antibody may be a full-length antibody (e.g., an IgG molecule such as an IgG1 molecule). Alternatively, the humanized antibody may be an antigen-binding fragment thereof. In some examples, the full-length antibody may comprise a wild-type Fc region. In other examples, the full-length antibody may comprise a Fc variant having modified effector activity. One examples is the Fc region comprising the amino acid sequence of SEQ ID NO: 42. In specific examples, the humanized antibody disclosed herein may comprise a heavy chain having the amino acid sequence of SEQ ID NO: 6, and/or a light chain having the amino acid sequence of SEQ ID NO: 7.

In some embodiments, the humanized anti-CD137 antibody disclosed herein may be part of a multi-specific antibody, which further binds FcγRIIB.

In another aspect, provided herein is an isolated nucleic acid or set of nucleic acids, which collectively encode any of the humanized anti-CD137 antibodies disclosed herein. In some embodiments, the isolated nucleic acid or set of nucleic acids are located on one vector. In other embodiments, the set of nucleic acids are located on two vectors. In some examples, the one or two vectors are one or two expression vectors.

In yet another aspect, provided herein is a host cell comprising any of the isolated nucleic acid or set of nucleic acids disclosed herein. For example, the host cell may comprise one or more expression vectors for producing the humanized anti-CD137 antibodies.

In addition, the present disclosure features a pharmaceutical composition, comprising any of the humanized anti-CD137 antibodies disclosed herein, or the nucleic acid(s) encoding such.

In another aspect, the present disclosure provides a method of modulating immune responses in a subject, the method comprising administering to a subject in need thereof an effective amount of any of the pharmaceutical composition disclosed herein that comprise a humanized anti-CD137 antibody as also disclosed herein. In some embodiments, the subject may be on a therapy involving an immune checkpoint inhibitor. In other embodiments, the method may further comprise administering to the subject an immune checkpoint inhibitor. Exemplary checkpoint inhibitors include anti-PD-1 antibodies or anti-PD-L1 antibodies. One example is pembrolizumab.

In some embodiments, the subject to be treated may be a human patient having, suspected of having, or at risk for a cancer. Examples include prostate cancer, colon cancer, or melanoma. In some examples, the cancer is an advanced, a metastatic, or an unresectable malignancy. In some examples, the cancer is confirmed histologically or cytologically.

In some embodiments, the subject to be treated may be a human patient having, suspected of having, or at risk for an immune disorder. In some examples, the immune disorder can be an autoimmune disease. Examples include rheumatoid arthritis (RA), systemic lupus erythematosus (SLE), Type I diabetes, multiple sclerosis, Celiac Disease, and graft-versus-host (GVH) disease.

In some embodiments, the subject (e.g., a human patient) has undergone or is undergoing a therapy for the cancer or the immune disorder.

In some embodiments, the humanized anti-CD137 antibody (e.g., clone 3712-IgG1v) can be administered to the subject at a dose of about 0.3 to 10 mg/kg. In some embodiments, the humanized anti-CD137 antibody is administered to the subject once every 2-4 weeks, optionally once every three weeks.

In addition, provided herein is a method of producing a humanized anti-CD137 antibody, comprising: (i) culturing the host cell disclosed herein that comprise one or more expression vectors coding for any of the humanized anti-CD137 antibodies disclosed herein under conditions allowing for expression of the anti-CD137 antibody; and (ii) harvesting the anti-CD137 antibody thus produced from the cell culture. In some embodiments, the method may further comprise isolating the antibody from the host cells or from the culture supernatant.

Also within the scope of the present disclosure is humanized anti-CD137 as disclosed herein for use in treating cancer or immune disorders as also disclosed herein, as well as uses of such humanized anti-CD137 antibodies for manufacturing a medicament for use in treating the cancer or immune disorders.

The details of one or more embodiments of the invention are set forth in the description below. Other features or advantages of the present invention will be apparent from the following drawing and detailed description of several embodiments, and also from the appended claims.

BRIEF DESCRIPTION OF DRAWINGS

The following drawings form part of the present specification and are included to further demonstrate certain aspects of the present disclosure, which can be better understood by reference to the drawing in combination with the detailed description of specific embodiments presented herein.

In FIG. 8A, FcRn at final concentrations of 10000, 5000, 2500, 1250, 625, 312.5, and 156.3 ng/mL, as shown on the x-axis, were added to plates coated with clone 3712 or Avastin. The FcRn bound to the coated antibody was detected by an anti-His Tag-HRP antibody. In FIG. 8B, clone 3712 or Avastin at concentrations of 0.125, 0.25, 0.5, 1, 2, 4, and 8 μg/mL, as shown on the x-axis, were coated on ELISA plates and C1q at 2 mg/mL was added to plates. C1q bound to antibody was detected by an anti-human C1q-HRP antibody.

FIGS. 12A-12B are graphs showing tumor growth curves of various groups in a mouse tumor model. Murine colon cancer MC38 cells were subcutaneously implanted into homozygous B-h4-1BB mice on day 0. Mice with established tumors were divided into control and treatment groups (n=6) on day 7, and treatments as shown were administered by intraperitoneal injections. Tumor sizes were measured by caliber 2 times a week and calculated as tumor volume using formula of $0.5 \times length \times width^2$. The average ±SEM of tumor sizes are shown in FIG. 12A, whereas FIG. 12B shows the individual mouse data.

FIG. 13A compares treatment with clone 3712 with two reference antibodies reported in literature. FIG. 13B shows dosing effects of clone 3712. Tumor sizes were measured by caliber 2 times a week and calculated as tumor volume using formula of $0.5 \times length \times width^2$. The average ±SEM of tumor sizes are shown. Mean values were compared using multiple t tests in Prism. Statistically significant differences p<0.05, and p<0.01 are noted with *, and ** respectively when compared to the clone 3712 10 mg/kg group in both FIG. 13A and FIG. 13B.

FIGS. 16A-16 D include diagrams that show binding of clone 3712 with various chimeric CD137 receptor proteins. FIG. 16A and FIG. 16C: binding of clone 3712 to CD137 receptor proteins Ly048, Ly049, and ly050 relative to human CD137. FIG. 16B and FIG. 16D: binding of clone 3712 to CD137 receptor proteins Ly051, Ly052, and ly110 relative to human CD137.

DETAILED DESCRIPTION OF INVENTION

Figure 1:
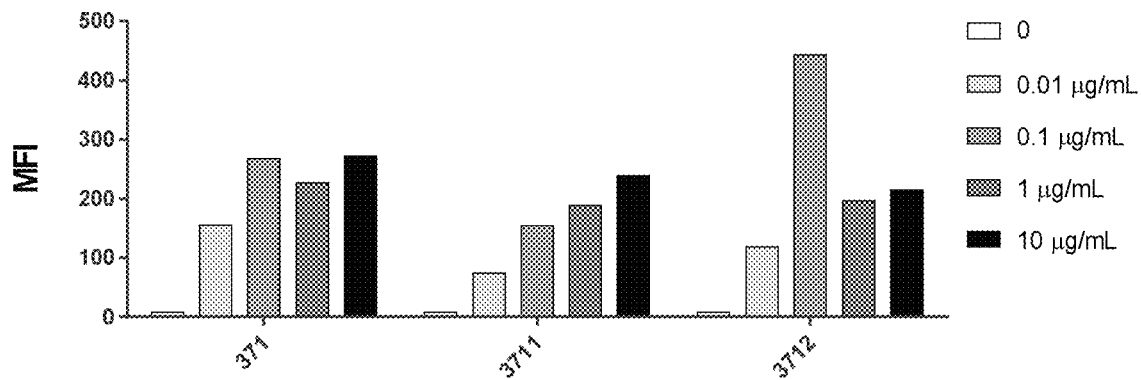
FIG. 1 is a graph showing FACS analysis of reference antibody 371 (murine/human chimeric) and humanized version thereof, clones 3711 and 3712, for binding to CHO cells over-expressing human CD137. Antibodies in serial dilution at final concentrations as shown were incubated with CHO-human CD137 cells. Mean fluorescence intensity (MFI), shown on the y-axis, indicates antibody binding.

Provided herein are humanized agonistic antibodies capable of binding to CD137 and FcγRIIB (e.g., via a suitable Fc portion) and enhancing the signaling mediated by CD137 in the presence of FcγRIIB. Such anti-CD137 antibodies may be derived from reference anti-CD137 antibody clone 371 (a mouse parent), which is disclosed herein. The humanized anti-CD137 antibodies disclosed herein showed similar or superior bioactivities relative to the parent clone as shown in the Examples below. For example, humanized anti-CD137 antibody clone 3712 (e.g., in IgG1 format, which may comprise an IgG Fc variant) had comparable CD137 binding affinity, selective binding to FcγRIIB, and superior T cell stimulation activity to the parent antibody, and demonstrated superior anti-tumor activity to known anti-CD137 antibodies. The humanized antibodies were safe as investigated in an animal model. The humanized antibodies are expected to show a safety profile in human. In addition, the humanized anti-CD137 antibodies described herein may have synergistic activities in combination with anti-PD-1 and other immunotherapeutics, as well as cancer vaccine, cellular therapy, and/or other oncology therapeutic methods.

CD137 (also known as 4-1BB or TNFRSF9), is a member of the tumor necrosis factor (TNF) receptor family It is expressed by activated T cells (more prevalently by CD8+ than CD4+ (Gramaglia et al., *Eur. J. Immunol.*, 30(2):392-402 (2000)), as well as dendritic cells, B cells, follicular dendritic cells, natural killer cells, granulocytes, and in the cells of blood vessel walls at sites of inflammation. CD137 expression on dendritic cells has been shown to lead to the secretion of IL-6 and IL-12, as well as an increased ability of the DC to stimulate T cell responses to alloantigens as well as to infiltrate tumors (Pan et al., *J. Immunol.*, 172(8): 4779-89 (2004)). Activated natural killer cells express CD137 after stimulation with cytokines, promoting the proliferation of natural killer cells and IFN-γ secretion without affecting cytolytic activity (Wilcox et al., *J. Immunol.*, 169(8):4230-6 (2002)).

Accordingly, described herein are humanized anti-CD137 antibodies (e.g., agonistic anti-CD137 antibodies), nucleic acids encoding such, pharmaceutical compositions comprising the antibody or the encoding nucleic acid(s), as well as uses of such antibodies in therapeutic applications.

Humanized Antibodies Binding to CD137

The present disclosure provides humanized antibodies that bind CD137, particularly human and/or monkey CD137. Such antibodies may be agonistic antibodies, which, upon binding to CD137, elicit cell signaling medicated by CD137.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

A typical antibody molecule comprises a heavy chain variable region ($V_H$) and a light chain variable region ($V_L$), which are usually involved in antigen binding. The $V_H$ and $V_L$ regions can be further subdivided into regions of hypervariability, also known as "complementarity determining regions" ("CDR"), interspersed with regions that are more conserved, which are known as "framework regions" ("FR"). Each $V_H$ and $V_L$ is typically composed of three CDRs and four FRs, arranged from amino-terminus to carboxy-terminus in the following order: FR1, CDR1, FR2, CDR2, FR3, CDR3, FR4. The extent of the framework region and CDRs can be precisely identified using methodology known in the art, for example, by the Kabat definition, the Chothia definition, the AbM definition, and/or the contact definition, all of which are well known in the art. See, e.g., Kabat, E. A., et al. (1991) *Sequences of Proteins of Immunological Interest, Fifth Edition*, U.S. Department of Health and Human Services, NIH Publication No. 91-3242, Chothia et al., (1989) *Nature* 342:877; Chothia, C. et al. (1987) *J. Mol. Biol.* 196:901-917, Al-lazikani et al (1997) *J. Molec. Biol.* 273:927-948; and Almagro, J. Mol. Recognit. 17:132-143 (2004). See also hgmp.mrc.ac.uk and bioinf.org.uk/abs.

Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, or six) which are altered with respect to the original antibody, which are also termed one or more CDRs "derived from" one or more CDRs from the original antibody. Humanized antibodies may also involve affinity maturation.

Methods for constructing humanized antibodies are also well known in the art. See, e.g., Queen et al., *Proc. Natl. Acad. Sci. USA*, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions can be used to substitute for the corresponding residues in the human acceptor genes.

In some embodiments, an anti-CD137 antibody as described herein has a suitable binding affinity for the target antigen (e.g., CD137) or antigenic epitopes thereof. As used herein, "binding affinity" refers to the apparent association constant or $K_A$. The $K_A$ is the reciprocal of the dissociation constant ($K_D$). The anti-CD137 antibody described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the anti-CD137 antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[Bound]=[Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The humanized anti-CD137 antibody described herein may be derived from antibody clone 371, the $V_H$ and $V_L$ sequences of which are provided below with CDRs in boldface (determined by Kabat numbering). Further information of reference antibody 371 can be found in WO2019/113039, the relevant disclosures of which are herein incorporated by reference for the purposes or subject matter referenced herein.

```
>LYV371_VH
                                           (SEQ ID NO: 1)
QVQLQQSGAELVRPGASVTLSCKASGYTFAGFEMHWIKQTPVHGLGWIG

AIDPKTGGTDYNQKFKDKALLTADKSSNTAYMELR

SLTSEDSAVYYCTRDLGYFDVWGTGTTVTVSS

>LYV371_VL
                                           (SEQ ID NO: 2)
DIQMTQTTSSLSASLGDRVTISCRASQDIRSNLNWYQQKPDGTVKLLIY

YTSRLHSGVPSRFSGSGSGTDYSLTISNLEQEDIATYFCQQSEKLPRTF

GGGTKLEIRR
```

The humanized anti-CD137 antibodies derived from reference antibody 371 may comprise substantially similar heavy chain and light chain complementary regions (CDRs), which can be grafted into a suitable human $V_H$ framework and a suitable $V_L$ framework, respectively. An antibody having "substantially similar" heavy chain CDRs or light chain CDRs relative to the corresponding CDRs in a reference antibody means that the heavy chain or light chain CDRs in the antibody, in collection, contain less than 10 amino acid residue variations (e.g., less than 9, 8, 7, 6, 5, 4, 3, 2, or 1 amino acid variation) relative to the corresponding CDRs, in connection, in the reference antibody. For example, the humanized antibody may comprise only up to 8 (e.g., 8, 7, 6, 5, 4, 3, 2, or 1) amino acid residue variations in the total heavy chain and/or light chain CDR regions and binds the same epitope of CD137 with substantially similar affinity (e.g., having a $K_D$ value in the same order) as the reference antibody.

In some instances, the humanized antibody disclosed herein may have the same heavy chain CDR3 as reference antibody 371, and optionally the same light chain CDR3 as the reference antibody. Alternatively or in addition, the humanized antibody may have the same heavy chain CDR1 and/or CDR2 as the reference antibody, and optionally the same light chain CDR1 and/or CDR2 as the reference antibody.

The amino acid residue variations can be conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the humanized anti-CD137 antibody disclosed herein contains the same heavy chain and light chain CDRs as reference antibody 371. Two antibodies having the same $V_H$ and/or $V_L$ CDRs means that their CDRs are identical when determined by the same approach (e.g., the Kabat approach, the Chothia approach, the AbM approach, the Contact approach, or the IMGT approach as known in the art. See, e.g., bioinf.org.uk/abs/).

In some embodiments, the humanized anti-CD137 antibodies disclosed herein comprise heavy chain and light chain CDRs derived from the parent antibody 371 (substantially similar or identical), which can be grafted to the framework of a suitable recipient human $V_H$ gene and $V_L$ gene. In some example, the recipient human $V_H$ gene can be IGH1-2*02. Alternatively or in addition, the recipient human $V_L$ gene can be a Vκ gene, which can be IGKV1-39*01.

In some embodiments, the heavy and light chain CDRs from clone 371 can be grafted into the framework of the suitable recipient $V_H$ and $V_L$ genes without introducing further mutations into the framework regions. In other embodiments, one or more back mutations can be introduced into the framework regions to enhance binding activity, stability, and/or other preferred properties. As used herein, "back mutation" refers to converting the amino acid residue at a particular position in the human recipient $V_H$ or $V_L$ framework back to the amino acid residue at the corresponding position in the mouse parent antibody framework.

Provided below are exemplary humanized VH and VL chains derived from reference antibody 371 (CDRs following the Kabat numbering scheme are in boldface and back mutations in boldface and underlined):

>LYV371_VH-1
(SEQ ID NO: 3)
QVQLVQSGAEVKKPGASVKVSCKASGYTFAGFEMHWVRQAPGQGLEWMG

AIDPKTGGTDYNQKFKDRVTMTRDTSISTAYMEL

SRLRSDDTAVYYCARDLGYFDVWGQGTLVTVSS

>LYV371_VH-2
(SEQ ID NO: 8)
QVQLVQSGAEVKPGASVKVSCKASGYTFAGFEMHWVRQAPGQGLGWMG

AIDPKTGGTDYNQKFKDRVTMTADTSISTAYMELSRLRSDDTAVYYCT

RDLGYFDVWGQGTLVTVSS

>LYV371_VH-3
(SEQ ID NO: 9)
QVQLVQSGAEVKPGASVKLSCKASGYTFAGFEMHWIRQAPGQGLGWIG

AIDPKTGGTDYNQKFKDRATLTADTSISTAYMELSRLRSDDTAVYYCT

RDLGYFDVWGQGTLVTVSS

>LYV371_VL-1
(SEQ ID NO: 4)
DIQMTQSPSSLSASVGDRVTITCRASQDIRSNLNWYQQKPGKAPKLLIY

YTSRLHSGVPSRFSGSGSGTDFTLTISSLQPEDFATYYCQQSEKLPRTF

GGGTKVEIRR

>LYV371_VL-2
(SEQ ID NO: 5)
DIQMTQSPSSLSASVGDRVTITCRASQDIRSNLNWYQQKPGGAVKLLIY

YTSRLHSGVPSRFSGSGSGTDYTLTISSLQPEDFATYFCQQSEKLPRTF

GGGTKVEIRR

>LYV371_VL-3
(SEQ ID NO: 10)
DIQMTQSPSSLSASVGDRVTITCRASQDIRSNLNWYQQKPGGAVKLLIY

YTSRLHSGVPSRFSGSGSGTDYTLTISSLQPEDFATYFCQQSEKLPRTF

GGGTKLEIRR

Tables 1 and 2 below provide the heavy chain and light chain framework regions (FRs) and CDRs sequences of the parent antibody and the exemplary humanized $V_H$ and $V_L$ chains derived therefrom:

TABLE 1

Heavy Chain FRs and CDRs

| | VH of Antibody 371 | Humanized VH-1 | Humanized VH-2 | Humanized VH-3 |
|---|---|---|---|---|
| HC FR1 | QVQLQQSGAELVRPGASVTLSCKAS (SEQ ID NO: 11) | QVQLVQSGAEVKKPGASVKVSCKAS (SEQ ID NO: 18) | QVQLVQSGAEVVKPGASVKVSCKAS (SEQ ID NO: 22) | QVQLVQSGAEVVKPGASVKLSCKAS (SEQ ID NO: 25) |
| HC CDR1 | GYTFAGFEMH (SEQ ID NO: 12) | GYTFAGFEMH (SEQ ID NO: 12) | GYTFAGFEMH (SEQ ID NO: 12) | GYTFAGFEMH (SEQ ID NO: 12) |
| HC FR2 | WIKQTPVHGLGWIG (SEQ ID NO: 13) | VRQAPGQGLEWMG (SEQ ID NO: 19) | VRQAPGQGLGWMG (SEQ ID NO: 23) | IRQAPGQGLGWIG (SEQ ID NO: 26) |
| HC CDR2 | AIDPKTGGTDYNQKFKD (SEQ ID NO: 14) | AIDPKTGGTDYNQKFKD (SEQ ID NO: 14) | AIDPKTGGTDYNQKFKD (SEQ ID NO: 14) | AIDPKTGGTDYNQKFKD (SEQ ID NO: 14) |
| HC FR3 | KALLTADKSSNTAYMELRSLTSEDSAVYYCTR (SEQ ID NO: 15) | RVTMTRDTSISTAYMELSRLRSDDTAVYYCAR (SEQ ID NO: 20) | RVTMTADTSISTAYMELSRLRSDDTAVYYCTR (SEQ ID NO: 24) | RATLTADTSISTAYMELSRLRSDDTAVYYCTR (SEQ ID NO: 27) |
| HC CDR3 | DLGYFDV (SEQ ID NO: 16) | DLGYFDV (SEQ ID NO: 16) | DLGYFDV (SEQ ID NO: 16) | DLGYFDV (SEQ ID NO: 16) |
| HC FR4 | WGTGTTVTVSS (SEQ ID NO: 17) | WGQGTLVTVSS (SEQ ID NO: 21) | WGQGTLVTVSS (SEQ ID NO: 21) | WGQGTLVTVSS (SEQ ID NO: 21) |

TABLE 2

Light Chain FRs and CDRs

| | VL of Antibody 371 | Humanized VL-1 | Humanized VL-2 | Humanized VL-3 |
|---|---|---|---|---|
| LC FR1 | DIQMTQTTSSLSASLGDRVTISC (SEQ ID NO: 28) | DIQMTQSPSSLSASVGDRVTITC (SEQ ID NO: 35) | DIQMTQSPSSLSASVGDRVTITC (SEQ ID NO: 35) | DIQMTQSPSSLSASVGDRVTITC (SEQ ID NO: 35) |
| LC CDR1 | RASQDIRSNLN (SEQ ID NO: 29) | RASQDIRSNLN (SEQ ID NO: 29) | RASQDIRSNLN (SEQ ID NO: 29) | RASQDIRSNLN (SEQ ID NO: 29) |
| LC FR2 | WYQQKPDGTYVKLLI (SEQ ID NO: 30) | WYQQKPGKAPKLLIY (SEQ ID NO: 36) | WYQQKPGGAVKLLIY (SEQ ID NO: 39) | WYQQKPGGAVKLLIY (SEQ ID NO: 39) |
| LC CDR2 | YTSRLHS (SEQ ID NO: 31) | YTSRLHS (SEQ ID NO: 31) | YTSRLHS (SEQ ID NO: 31) | YTSRLHS (SEQ ID NO: 31) |
| LC FR3 | GVPSRFSGSGSGTDYSLTISNLEQEDIATYFC (SEQ ID NO: 32) | GVPSRFSGSGSGTDFTLTISSLQPEDFATYYC (SEQ ID NO: 37) | GVPSRFSGSGSGTDYTLTISSLQPEDFATYFC (SEQ ID NO: 40) | GVPSRFSGSGSGTDYTLTISSLQPEDFATYFC (SEQ ID NO: 40) |
| LC CDR3 | QQSEKLPRT (SEQ ID NO: 33) | QQSEKLPRT (SEQ ID NO: 33) | QQSEKLPRT (SEQ ID NO: 33) | QQSEKLPRT (SEQ ID NO: 33) |

TABLE 2-continued

Light Chain FRs and CDRs

| | VL of Antibody 371 | Humanized VL-1 | Humanized VL-2 | Humanized VL-3 |
|---|---|---|---|---|
| LC FR4 | FGGGTKLEIR (SEQ ID NO: 34) | FGGGTKVEIRR (SEQ ID NO: 38) | FGGGTKVEIRR (SEQ ID NO: 38) | FGGGTKLEIRR (SEQ ID NO: 41) |

In some embodiments, the humanized anti-CD137 antibody disclosed herein comprises a heavy chain CDR1 (HC CDR1) comprising the sequence of SEQ ID NO: 12, a HC CDR2 comprising the sequence of SEQ ID NO: 14, a HC CDR3 comprising the sequence of SEQ ID NO: 16, and/or a light chain CDR1 (LC CDR1) comprising the sequence of SEQ ID NO:29, a LC CDR2 comprising the sequence of SEQ ID NO: 31, and a LC CDR3 comprising the sequence of SEQ ID NO: 33.

In some embodiments, the humanized anti-CD137 antibody disclosed herein may further comprise the same heavy chain framework region 1 (HC FR1) as LYV371_VH-1 (e.g., SEQ ID NO: 18) or a variant thereof having no more than one, two or three back mutations. Alternatively or in addition, the humanized anti-CD137 antibody may further comprise the same HC FR2 as LYV371_VH-1 (e.g., SEQ ID NO:19) or a variant thereof having no more than one, two or three back mutations. Alternatively or in addition, the humanized anti-CD137 antibody may further comprise the same HC FR3 as LYV371_VH-1 (e.g., SEQ ID NO:20) or a variant thereof having no more than one, two or three back mutations. Alternatively or in addition, the humanized anti-CD137 antibody may comprise the same HC FR4 as LYV371_VH-1 (e.g., SEQ ID NO:21) or a variant thereof having no more than one, two or three back mutations. Exemplary back mutations may occur at one or more of positions K12 (e.g., K12V), V20 (e.g., V20L) in FR1, V37 (e.g., V37I), E46 (e.g., E46G), and W48 (e.g., W48I) in FR2, V68 (e.g., V68A), M70 (e.g., M70L), R72 (e.g., R72A) and A97 (e.g., A97T) in FR3.

In some embodiments, the humanized anti-CD137 antibody disclosed herein comprises: (i) a HC FR1 of SEQ ID NO:18, SEQ ID NO:22, or SEQ ID NO:25; (ii) a HC FR2 of SEQ ID NO:19, SEQ ID NO:23, or SEQ ID NO:26, (iii) a HC FR3 of SEQ ID NO:20, SEQ ID NO:24, or SEQ ID NO:27; and/or (iv) a HC FR4 of SEQ ID NO:21. In some examples, the humanized anti-CD137 antibody has the same heavy chain FR1, FR2, FR3, and FR4 as VH-1, VH-2, or VH-3 shown in Table 1.

In some embodiments, the humanized anti-CD137 antibody disclosed herein may further comprises the light chain framework region 1 (LC FR1) as LYV371_VL-1 (e.g., SEQ ID NO: 35) or a variant thereof having no more than one, two or three back mutations. Alternatively or in addition, the humanized anti-CD137 antibody disclosed herein may further comprise the same LC FR2 as c LYV371_VL-1 (e.g., SEQ ID NO: 36) or a variant thereof having no more than one, two or three back mutations. Alternatively or in addition, the humanized anti-CD137 antibody may further comprise the same LC FR3 as LYV371_VL-1 (e.g., SEQ ID NO: 37) or a variant thereof having no more than one, two or three back mutations. Alternatively or in addition, the humanized anti-CD137 antibody may further comprise the same LC FR4 as LYV371_VL-1 (e.g., SEQ ID NO: 338) or a variant thereof having no more than one, two or three back mutations.

In some embodiments, the humanized anti-CD137 antibody disclosed herein comprises a humanized light chain variable region comprising one or more (e.g. 1, 2, 3, or 4) back mutations at one or more positions K42 (e.g., K42G) and P44 (e.g., P44V) in FR2, F71 (e.g., F71Y) and Y87 (e.g., Y87F) in FR3, and V104 (e.g., V104L) in FR4.

In some embodiments, the humanized anti-CD137 antibody disclosed herein further comprises: (i) a LC FR1 comprising the sequence of SEQ ID NO: 35, (ii) a LC FR2 comprising the sequence of SEQ ID NO: 36 or SEQ ID NO: 39, (iii) a LC FR3 comprising the sequence of SEQ ID NO: 37 or SEQ ID NO: 40, and/or (iv) a LC FR4 comprising the sequence of SEQ ID NO: 41. In some examples, the humanized anti-CD137 antibody comprises the same LC FR1, LC FR2, LC FR3, and LC FR4 as VL-1, VL-2, or VL-3 shown in Table 2.

In specific examples, the humanized anti-CD137 antibody disclosed herein comprises a VH chain comprising the amino acid sequence of SEQ ID NO: 3, SEQ ID NO:8, or SEQ ID NO: 9. Alternatively or in addition, the humanized anti-CD137 antibody disclosed herein comprises a VL chain comprising the amino acid sequence of SEQ ID NO: 4, SEQ ID NO:5, or SEQ ID NO: 10. Exemplary humanized anti-CD137 antibodies provided herein include clones 3711, 3712, 3713, 3714, 3715, 3716, 3717, 3718, and 3719. See Table 3 below for the VH and VL components of these exemplary humanized anti-CD137 antibodies. Such exemplary antibodies may be in any antibody format as disclosed herein, for example, single-chain antibody, Fab fragment, or full-length antibody.

In some embodiments, the heavy chain of any of the anti-CD137 antibodies as described herein may further comprise a heavy chain constant region (CH) or a portion thereof (e.g., CH1, CH2, CH3, or a combination thereof). The heavy chain constant region of the antibodies described herein may comprise a single domain (e.g., CH1, CH2, or CH3) or a combination of any of the single domains.

In one specific example, the heavy chain constant region is from a human IgG (a gamma heavy chain) of any IgG subfamily as described herein. In one example, the constant region is from human Ig molecule such as an IgG1. The Fc regions of any of the humanized anti-CD137 antibodies disclosed herein may be a wild-type Fc domain. Alternatively, the Fc domain may be an Fc variant comprising one or more mutations relative to the wild-type counterpart to modulate one or more effector activities. For example, it may comprise a modified constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in *Eur. J. Immunol.* (1999) 29:2613-2624; PCT Application No. PCT/GB99/01441; and/or UK Patent Application No. 9809951.8. In some embodiments, the anti-CD137 antibody described herein may contain a mutated Fc region as compared with a wild-type counterpart such that the antibody has a higher binding affinity to an Fc receptor, for example, FcγRIIB (CD32B). Such antibodies may engage FcγRIIB-expressing cells efficiently, thereby enhancing therapeutic effects. In other embodiments, the anti-CD137 antibody described herein may contain a mutated Fc region as compared with a wild-type counterpart such that the antibody has a selective binding affinity to an Fc receptor, for example, FcγRIIB (CD32B). Such antibodies may engage FcγRIIB-expressing cells selectively and efficiently, thereby enhancing therapeutic effects.

Fc variants for use in making the humanized anti-CD137 antibodies can be found in, e.g., WO2018/183520, the relevant disclosures of which are incorporated by reference herein for the purpose of subject matter referenced herein. In some instances, the Fc variant may contain an S/P substitution at position 228 (EU numbering). In one example, the humanized anti-CD137 antibodies disclosed herein may comprise an Fc domain comprising the following amino acid sequence of which is provided below (SEQ ID NO: 42):

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGPSVFLFPPKPKDTLMISRTPEVTCVVVDVEH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK

Any of the anti-CD137 antibodies described herein may comprise a light chain that further comprises a light chain constant region, which can be any CL known in the art. In some examples, the CL is a kappa light chain.

Antibody heavy and light chain constant regions are well known in the art, e.g., those provided in the IMGT database (imgt.org) or at vbase2.org/vbstat.php., both of which are incorporated by reference herein.

Provided below are the amino acid sequences of one exemplary full-length humanized anti-CD137 antibody Clone 3712 (IgG1v/kappa):

Heavy Chain of Clone 3712-IgG1v
(SEQ ID NO: 6)
QVQLVQSGAEVKKPGASVKVSCKASGYTFAGF

EMHWVRQAPGQGLEWMGAIDPKTGGTDYNQKF

KDRVTMTRDTSISTAYMELSRLRSDDTAVYYC

ARDLGYFDVWGQGTLVTVSS

ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGPSVFLFPPKPKDTLMISRTPEVTCVVVDVEH

EDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCL

VKGFYPSDIAVEWESNGQPENNYKTTPPVLDSDGSFFLYSKLTVDKSRWQ

QGNVFSCSVMHEALHNHYTQKSLSLSPGK*

Light Chain of Clone 3712-IgG1v
(SEQ ID NO: 7)
DIQMTQSPSSLSASVGDRVTITCRASQDIRSN

LNWYQQKPGGAVKLLIYYTSRLHSGVPSRFSG

SGSGTDYTLTISSLQPEDFATYFCQQSEKLPR

TFGGGTKVEIRR

TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC*

In some embodiments, the anti-CD137 antibody is a bi-specific antibody capable of binding to both CD137 and FcγRIIB (not via Fc-FcR interaction). Such a bi-specific antibody may comprise a first antigen-binding region and a second antigen-binding region, each of which may comprise a $V_H/V_L$ pair. The first antigen-binding region binds CD137 while the second antigen-binding region binds FcγRIIB.

In some embodiments, the anti-CD137 antibody is a bi-specific or multi-specific (e.g., tri-specific) antibody capable of binding to both CD137 and one or more other antigens of interest. Such a bi-specific or multi-specific antibody may comprise a first antigen-binding region, a second antigen-binding region, and optionally a third antigen-binding region, each of which may comprise a $V_H/V_L$ pair. The first antigen-binding region binds CD137 while the second antigen-binding region binds another antigen of interest.

Preparation of Humanized Anti-CD137 Antibodies

Methods for constructing humanized antibodies are well known in the art. See, e.g., Queen et al., *Proc. Nall. Acad. Sci. USA*, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

In some examples, a humanized anti-CD137 antibody as disclosed herein can be prepared by recombinant technology as exemplified below.

Nucleic acids encoding the heavy and light chain of an anti-CD137 antibody as described herein can be cloned into one expression vector, each nucleotide sequence being in operable linkage to a suitable promoter. In one example, each of the nucleotide sequences encoding the heavy chain and light chain is in operable linkage to a distinct prompter. Alternatively, the nucleotide sequences encoding the heavy chain and the light chain can be in operable linkage with a single promoter, such that both heavy and light chains are expressed from the same promoter. When necessary, an internal ribosomal entry site (IRES) can be inserted between the heavy chain and light chain encoding sequences.

In some examples, the nucleotide sequences encoding the two chains of the antibody are cloned into two vectors, which can be introduced into the same or different cells. When the two chains are expressed in different cells, each of them can be isolated from the host cells expressing such and the isolated heavy chains and light chains can be mixed and incubated under suitable conditions allowing for the formation of the antibody.

Generally, a nucleic acid sequence encoding one or all chains of an antibody can be cloned into a suitable expression vector in operable linkage with a suitable promoter using methods known in the art. For example, the nucleotide sequence and vector can be contacted, under suitable conditions, with a restriction enzyme to create complementary ends on each molecule that can pair with each other and be joined together with a ligase. Alternatively, synthetic nucleic acid linkers can be ligated to the termini of a gene. These synthetic linkers contain nucleic acid sequences that correspond to a particular restriction site in the vector. The selection of expression vectors/promoter would depend on the type of host cells for use in producing the antibodies.

A variety of promoters can be used for expression of the antibodies described herein, including, but not limited to, cytomegalovirus (CMV) intermediate early promoter, a viral LTR such as the Rous sarcoma virus LTR, HIV-LTR, HTLV-1 LTR, the simian virus 40 (SV40) early promoter, *E. coli* lac UV5 promoter, and the herpes simplex tk virus promoter. Regulatable promoters can also be used. Such regulatable promoters include those using the lac repressor from *E. coli* as a transcription modulator to regulate transcription from lac operator-bearing mammalian cell promoters [Brown, M. et al., *Cell*, 49:603-612 (1987)], those using the tetracycline repressor (tetR) [Gossen, M., and Bujard, H., *Proc. Natl. Acad. Sci. USA* 89:5547-5551 (1992); Yao, F. et al., *Human Gene Therapy*, 9:1939-1950 (1998); Shockelt, P., et al., *Proc. Natl. Acad. Sci. USA*, 92:6522-6526 (1995)]. Other systems include FK506 dimer, VP16 or p65 using astradiol, RU486, diphenol murislerone, or rapamycin. Inducible systems are available from Invitrogen, Clontech and Ariad.

Regulatable promoters that include a repressor with the operon can be used. In one embodiment, the lac repressor from *E. coli* can function as a transcriptional modulator to regulate transcription from lac operator-bearing mammalian cell promoters [M. Brown et al., *Cell*, 49:603-612 (1987); Gossen and Bujard (1992); M. Gossen et al., *Natl. Acad. Sci. USA*, 89:5547-5551 (1992)] combined the tetracycline repressor (tetR) with the transcription activator (VP 16) to create a tetR-mammalian cell transcription activator fusion protein, tTa (tetR-VP 16), with the tetO-bearing minimal promoter derived from the human cytomegalovirus (hCMV) major immediate-early promoter to create a tetR-tet operator system to control gene expression in mammalian cells. In one embodiment, a tetracycline inducible switch is used. The tetracycline repressor (tetR) alone, rather than the tetR-mammalian cell transcription factor fusion derivatives can function as potent trans-modulator to regulate gene expression in mammalian cells when the tetracycline operator is properly positioned downstream for the TATA element of the CMVIE promoter (Yao et al., *Human Gene Therapy*, 10(16):1392-1399 (2003)). One particular advantage of this tetracycline inducible switch is that it does not require the use of a tetracycline repressor-mammalian cells transactivator or repressor fusion protein, which in some instances can be toxic to cells (Gossen et al., *Natl. Acad. Sci. USA*, 89:5547-5551 (1992); Shockett et al., *Proc. Natl. Acad. Sci. USA*, 92:6522-6526 (1995)), to achieve its regulatable effects.

Additionally, the vector can contain, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; and T7 and SP6 RNA promoters for in vitro transcription of sense and antisense RNA. Suitable vectors and methods for producing vectors containing transgenes are well known and available in the art.

Examples of polyadenylation signals useful to practice the methods described herein include, but are not limited to, human collagen I polyadenylation signal, human collagen II polyadenylation signal, and SV40 polyadenylation signal.

One or more vectors (e.g., expression vectors) comprising nucleic acids encoding any of the antibodies may be introduced into suitable host cells for producing the antibodies. The host cells can be cultured under suitable conditions for expression of the antibody or any polypeptide chain thereof. Such antibodies or polypeptide chains thereof can be recovered by the cultured cells (e.g., from the cells or the culture supernatant) via a conventional method, e.g., affinity purification. If necessary, polypeptide chains of the antibody can be incubated under suitable conditions for a suitable period of time allowing for production of the antibody.

In some embodiments, methods for preparing an antibody described herein involve a recombinant expression vector that encodes both the heavy chain and the light chain of an anti-CD137 antibody, as also described herein. The recombinant expression vector can be introduced into a suitable host cell (e.g., a dhfr-CHO cell) by a conventional method, e.g., calcium phosphate-mediated transfection. Positive transformant host cells can be selected and cultured under suitable conditions allowing for the expression of the two polypeptide chains that form the antibody, which can be recovered from the cells or from the culture medium. When necessary, the two chains recovered from the host cells can be incubated under suitable conditions allowing for the formation of the antibody.

In one example, two recombinant expression vectors are provided, one encoding the heavy chain of the anti-CD137 antibody and the other encoding the light chain of the anti-CD137 antibody. Both of the two recombinant expression vectors can be introduced into a suitable host cell (e.g., dhfr-CHO cell) by a conventional method, e.g., calcium phosphate-mediated transfection. Alternatively, each of the expression vectors can be introduced into suitable host cells. Positive transformants can be selected and cultured under suitable conditions allowing for the expression of the polypeptide chains of the antibody. When the two expression vectors are introduced into the same host cells, the antibody produced therein can be recovered from the host cells or from the culture medium. If necessary, the polypeptide chains can be recovered from the host cells or from the culture medium and then incubated under suitable conditions allowing for formation of the antibody. When the two expression vectors are introduced into different host cells, each of them can be recovered from the corresponding host cells or from the corresponding culture media. The two polypeptide chains can then be incubated under suitable conditions for formation of the antibody.

Standard molecular biology techniques are used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

Any of the nucleic acids encoding the heavy chain, the light chain, or both of an anti-CD137 antibody as described herein, vectors (e.g., expression vectors) containing such; and host cells comprising the vectors are within the scope of the present disclosure.

Anti-CD137 antibodies thus prepared can be can be characterized using methods known in the art, whereby an increase in CD137 biological activity is detected and/or measured. For example, an ELISA-type assay may be suitable for qualitative or quantitative measurement of CD137 promotion of T cell proliferation.

Methods of Treatment

The present disclosure provides methods of treating a disease, for example a cancer or an immune disorder such as autoimmune disease, by administering a therapeutically effective amount of an anti-CD137 antibody. In some instances, any of the humanized anti-CD137 antibodies as disclosed herein may be co-used with an immune checkpoint inhibitor, such as an anti-PD-1 antibody. In one example, the anti-PD-1 antibody may be the anti-PD-1 antibody SSI-361 disclosed in WO2017087599, the relevant disclosure of which is incorporated by reference for the subject matter and purpose referenced herein, nivolumab (OPDIVO®), pembrolizumab (KEYTRUDA®), avelumab (BAVENCIO®), durvalumab (IMFINZI®), or atezolizumab (TECENTRIQ®). In particular, the anti-PD-1 antibody may be pembrolizumab.

Pharmaceutical Compositions

The antibodies, as well as the encoding nucleic acids or nucleic acid sets, vectors comprising such, or host cells comprising the vectors, as described herein can be mixed with a pharmaceutically acceptable carrier (excipient) to form a pharmaceutical composition for use in treating a target disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

In some examples, the pharmaceutical composition described herein comprises liposomes containing the antibodies (or the encoding nucleic acids) which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The antibodies, or the encoding nucleic acid(s), may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing an antibody with Intralipid™ or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulized by use of gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

Therapeutic Applications

To practice the method disclosed herein, an effective amount of the pharmaceutical composition described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. Commercially available nebulizers for liquid formulations, including jet nebulizers and ultrasonic nebulizers are useful for administration. Liquid formulations can be directly nebulized and lyophilized powder can be nebulized after reconstitution. Alternatively, the antibodies as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as a cancer, an immune disorder such as an autoimmune disease, or infection. In some embodiments, the pharmaceutical composition comprising the humanized anti-CD137 antibody is for use in enhancing immune responses in a subject, which is also within the scope of the present disclosure.

Examples of cancers include, but are not limited to, breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia, e.g., B Cell CLL; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

In one example, the cancer may be an advanced, a metastatic, or an unresectable malignancy. The malignancy may be confirmed histologically or cytologically. In particular, the malignancy may be advanced or metastatic.

A subject having a target cancer can be identified by routine medical examination, e.g., laboratory tests, organ functional tests, CT scans, or ultrasounds. A target cancer can also be identified histologically and/or cytologically. In some embodiments, the subject to be treated by the method described herein may be a human cancer patient who has undergone or is subjecting to an anti-cancer therapy, for example, chemotherapy, radiotherapy, immunotherapy, or surgery.

In some embodiments, the subject to be treated by the methods (e.g., involving clone 3712-IgG1v) disclosed herein may be a human patient at the age of 18 or older. The patient may: (i) have a histologically or cytologically confirmed metastatic or unresectable malignancy, (ii) have adequate bone marrow, liver, and renal functions, and/or (iii) recovered from all reversible AEs of previous anticancer therapies to baseline. Patients infected with HIV may be treated by the methods disclosed herein if the disease is under control of effective therapy.

Alternatively or in addition, the subject may be a human patient who does not have one or more of the following: (1) receipt of systemic anticancer therapy 5 half-lives of the first dose of the anti-CD137 antibody disclosed herein; (2) previous radiotherapy within 14 days of the first dose of the anti-CD137 antibody disclosed herein; (3) have active CNS metastasis and/or carcinomatous meningitis; (4) have received a live-virus vaccine within 30 days; (5) have had a Grade⩾3 allergic reaction to treatment with a monoclonal antibody; (6) abnormality of QT interval or syndrome; (7) with history of Grade⩾3 immune-related AEs (irAEs) or irAE; (8) is receiving an immunologically-based treatment for any reason; (9) on treatment with systemic immune-stimulatory agents within 4 weeks prior to the first dose of the anti-CD137 antibody; (10) have active chronic autoimmune disease that has required systemic treatment in the past 2 years or who are receiving systemic therapy for an autoimmune or inflammatory disease; (11) have a clinically significant cardiac condition, including unstable angina, acute myocardial infarction within 6 months; (12) have an active infection requiring intravenous (i.v.) anti-infectives within 14 days before the first dose of the anti-CD137 antibody; (13) show current evidence or history of interstitial lung disease or active, noninfectious pneumonitis requiring treatment such as oral or intravenous glucocorticoids to assist with management; (14) show evidence of severe or uncontrolled systemic disease; (15) have another disease or clinically significant abnormality in laboratory parameters; and/or (16) have previously had a stem cell or bone marrow or solid organ transplant.

In some embodiments, the methods disclosed herein is for treating an immune disorder. Immune disorders refer to a dysfunction of the immune system. Examples include autoimmune diseases, immunodeficiencies, or allergies. In some embodiments, the target disease for treatment is an autoimmune disease. Examples include, but are not limited to, rheumatoid arthritis (RA), systemic lupus erythematosus (SLE), Myasthenia Gravis (MG), Graves' Disease, Idiopathic Thrombocytopenia Purpura (ITP), Guillain-Barre Syndrome, autoimmune myocarditis, Membrane Glomerulonephritis, diabetes mellitus, Type I or Type II diabetes, multiple sclerosis, Reynaud's syndrome, autoimmune thyroiditis, gastritis, Celiac Disease, Vitiligo, Hepatitis, primary biliary cirrhosis, inflammatory bowel disease, spondyloarthropathies, experimental autoimmune encephalomyelitis, immune neutropenia, juvenile onset diabetes, and immune responses associated with delayed hypersensitivity mediated by cytokines, T-lymphocytes typically found in tuberculosis, sarcoidosis, and polymyositis, polyarteritis, cutaneous vasculitis, pemphigus, pemphigold, Goodpasture's syndrome, Kawasaki's disease, systemic sclerosis, anti-phospholipid syndrome, Sjogren's syndrome, graft-versus-host (GVH) disease, and immune thrombocytopenia.

A subject having a target autoimmune disease can be identified by routine medical examination, e.g., presence of antinuclear antibodies, anti-mitochondrial autoantibodies, anti-neutrophil cytoplasmic antibody, anti-phospholipid antibodies, anti-citrullinated peptide (anti-CCP), anti-rheumatoid factor, immunoglobulin A, C-reactive protein test, complement test, erythrocyte sedimentation rate (ESR) test, blood clotting profile, and protein electrophoresis/immunofixation electrophoresis, among others. In some embodiments, the subject to be treated by the method described herein may be a human subject with an autoimmune disease who has undergone or is subjecting to an autoimmune disease treatment, for example, immunosuppressive mediation, hormone replacement therapy, blood transfusions, anti-inflammatory medication, and/or pain medication.

A subject suspected of having any of such target disease/disorder might show one or more symptoms of the disease/disorder. A subject at risk for the disease/disorder can be a subject having one or more of the risk factors for that disease/disorder.

As used herein, "an effective amount" refers to the amount of each active agent required to confer therapeutic effect on the subject, either alone or in combination with one or more other active agents. In some embodiments, the therapeutic effect is increased CD137 activity, increased T cell proliferation and survival, and/or increased anti-tumor immune responses. Determination of whether an amount of the antibody achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a target disease/disorder. Alternatively, sustained continuous release formulations of an antibody may be appropriate. Various formulations and devices for achieving sustained release are known in the art.

In one example, dosages for an antibody as described herein may be determined empirically in individuals who have been given one or more administration(s) of the antibody. Individuals are given incremental dosages of the agonist. To assess efficacy of the agonist, an indicator of the disease/disorder can be followed.

Generally, for administration of any of the antibodies described herein, an initial candidate dosage can be about 2 mg/kg. For the purpose of the present disclosure, a typical daily dosage might range from about any of 0.1 µg/kg to 3 µg/kg to 30 µg/kg to 300 µg/kg to 3 mg/kg, to 30 mg/kg to 100 mg/kg or more, depending on the factors mentioned above. In some embodiments, a daily dosage may be 10 mg/kg. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. Each such period can be referred to as a cycle. In some embodiments, as many as 40 cycles, and particularly 35 cycles, may be administered. The progress of this therapy is easily monitored by conventional techniques and assays. The dosing regimen (including the antibody used) can vary over time.

In one example, the dosing frequency is once every 3 weeks. In particular, 0.3 to 10 mg/kg of the humanized anti-CD137 antibody disclosed herein (e.g., clone 3712-IgG1v) may be administered once every 3 weeks. As many as 35 cycles may be administered. The mode of administration in these embodiments may be intravenous.

In some embodiments, for an adult patient of normal weight, doses ranging from about 0.3 to 5.00 mg/kg may be administered. In some examples, the dosage of the anti-CD137 antibody described herein can be 10 mg/kg. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of an antibody as described herein will depend on the specific antibody, antibodies, and/or non-antibody peptide (or compositions thereof) employed, the type and severity of the disease/disorder, whether the antibody is administered for preventive or therapeutic purposes, previous therapy, the patient's clinical history and response to the agonist, and the discretion of the attending physician. Typically the clinician will administer an antibody, until a dosage is reached that achieves the desired result. In some embodiments, the desired result is an increase in anti-tumor immune response in the tumor microenvironment. Methods of determining whether a dosage resulted in the desired result would be evident to one of skill in the art. Administration of one or more antibodies can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity or prolonging survival. Alleviating the disease or prolonging survival does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

In some embodiments, the antibodies described herein are administered to a subject in need of the treatment at an amount sufficient to enhance the activity of CD137 (and/or T cell proliferation) by at least 10% (e.g., 20%, 30%, 40%, 50%, 60%, 70%, 80%, 90% or greater) in vivo.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, an antibody is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., *Trends Biotechnol*. (1993) 11:202; Chiou et al., Gene Therapeutics: Methods And Applications Of Direct Gene Transfer (J. A. Wolff, ed.) (1994); Wu et al., *J. Biol. Chem*. (1988) 263:621; Wu et al., *J. Biol. Chem*. (1994) 269:542; Zenke et al., *Proc. Natl. Acad. Sci. USA* (1990) 87:3655; Wu et al., *J. Biol. Chem*. (1991) 266:338.

Therapeutic compositions containing a polynucleotide (e.g., those encoding the antibodies described herein) are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther*. (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther*. (1992) 3:147); ligand-linked DNA (see, e.g., Wu, *J. Biol. Chem*. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, *Mol. Cell. Biol*. (1994) 14:2411, and in Woffendin, *Proc. Natl. Acad. Sci*. (1994) 91:1581.

The particular dosage regimen, i.e., dose, timing and repetition, used in the method described herein will depend on the particular subject and that subject's medical history.

In some embodiments, more than one antibody, or a combination of an antibody and another suitable therapeutic agent, may be administered to a subject in need of the treatment. The antibody can also be used in conjunction with other agents that serve to enhance and/or complement the effectiveness of the agents.

Treatment efficacy for a target disease/disorder can be assessed by methods well-known in the art.

Combined Therapy

The anti-CD137 antibodies described herein may be utilized in conjunction with other types of therapy for the target disease such as cancer, immune disorders, or infection.

When an anti-CD137 antibody as described herein is used for treating a cancer, it can be combined with an anti-cancer therapy, for example, those known in the art. Additional anti-cancer therapy includes chemotherapy, surgery, radiation, immunotherapy, gene therapy, and so forth. Such therapies can be administered simultaneously or sequentially (in any order) with the immunotherapy according to the present disclosure.

In some embodiments, the anti-CD137 antibody can be combined with other immunomodulatory treatments such as, e.g., inhibitors of a checkpoint molecule (e.g., PD-1, PD-L1, PD-L2, CTLA-4, CD40, LAG3, TIM-3, or A2aR). As demonstrated in FIG. 14, the combined treatment of an anti-CD137 antibody and an anti-PD-1 antibody resulted in a synergistic effect: tumor growth was significantly inhibited in a mouse model, compared to either of the two treatments alone.

Alternatively or in addition, the treatment of the present disclosure can be combined with a chemotherapeutic agent, for example, pyrimidine analogs (5-fluorouracil, floxuridine, capecitabine, gemcitabine and cytarabine), purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

When the anti-CD137 antibody as described herein for treating an immune disorder, it can be co-used with other immunomodulatory treatments such as, e.g., therapeutic vaccines (including but not limited to GVAX, DC-based vaccines, etc.). In some instances, the antibody can be combined with another therapy for autoimmune diseases. Examples include, but are not limited to, intravenous Ig therapy; nonsteroidal anti-inflammatory drugs (NSAID); corticosteroids; cyclosporins, rapamycins, ascomycins; cyclophosphamide; azathioprene; methotrexate; brequinar; FTY 720; leflunomide; mizoribine; mycophenolic acid; mycophenolate mofetil; 15-deoxyspergualine; an immunosuppressive agent, or an adhesion molecule inhibitor.

For examples of additional useful agents see also Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

When co-administered with an additional therapeutic agent, suitable therapeutically effective dosages for each agent may be lowered due to the additive action or synergy.

Kits for Use in Treatment of Diseases

The present disclosure also provides kits for use in treating or alleviating a target diseases, such as cancer, immune disorders, or infection as described herein. Such kits can include one or more containers comprising an anti-CD137 antibody, e.g., any of those described herein, and optionally a second therapeutic agent to be co-used with the anti-CD137 antibody, which is also described herein.

In some embodiments, the kit can comprise instructions for use in accordance with any of the methods described herein. The included instructions can comprise a description of administration of the anti-CD137 antibody, and optionally the second therapeutic agent, to treat, delay the onset, or alleviate a target disease as those described herein. The kit may further comprise a description of selecting an individual suitable for treatment based on identifying whether that individual has the target disease, e.g., applying the diagnostic method as described herein. In still other embodiments, the instructions comprise a description of administering an antibody to an individual at risk of the target disease.

The instructions relating to the use of an anti-CD137 antibody generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating the disease, such as cancer, immune disorders (e.g., an autoimmune disease), or infectious diseases. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an anti-CD137 antibody as those described herein.

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C.

Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

against the protein data bank (PDB) antibody database to identify templates for the Fv fragments and to build the domain interface. Structural template 1NMB (Malby et al., *Structure*, 1994 Aug. 15; 2(8):733-46) was selected, as its identity was 78%. The amino acid sequence alignment between reference antibody 371 antibody (SEQ ID NO: 2 before the break and SEQ ID:1 after the break) and the 1NMB template (SEQ ID NO: 45) is shown below, where I is the chain break and * indicates identical amino acid residues in both sequences.

```
1NMB  DIQMTQTTSSLSASLGDRVTISCRASQDISNYLNWYQQNPDGTVKLLIYYTSNLHSEVPS
371   DIQMTQTTSSLSASLGDRVTISCRASQDIRSNLNWYQQKPDGTVKLLIYYTSRLHSGVPS
      ****************************** .******:*************.*** ***

1NMB  RFSGSGSGTDYSLTISNLEQEDIATYFCQQDFTLPFTFGGGTKLEIRRA|QVQLQQPGAEL
371   RFSGSGSGTDYSLTISNLEQEDIATYFCQQSEKLPRTFGGGTKLEIR--|QVQLQQSGAEL
      ****************************** .** ***********:  ****** ****

1NMB  VKPGASVRMSCKASGYTFTNYNMYWVKQSPGQGLEWIGIFYPGNGDTSYNQKFKDKATLT
371   VRPGASVTLSCKASGYTFAGFEMHWIKQTPVHGLGWIGAIDPKTGGTDYNQKFKDKALLT
      *:***** :********: .:.:*:*:**:* :** *** : * .*.*.********* **

1NMB  ADKSSNTAYMQLSSLTSEDSAVYYCARSGGSYRYDGGFDYWGQGTTLTVSS
371   ADKSSNTAYMELRSLTSEDSAVYYCTRDL------GYFDVWGTGTTVTVSS
      **********:* *************:*.      * ** ** ***:****
```

EXAMPLES

Example 1: Generation of Humanized Anti-CD137 Antibodies

Humanization and Back Mutation Design

Reference antibody 371 was humanized as described below. Sequence alignments comparing the reference antibody 371 variable domains to human germlines were generated (Glanville J. et al. PNAS 2009; 106 (48) 20216-21). Based on overall sequence identity, matching interface positions, and similarly classed CDR canonical positions, a germline family was identified for each of the light and heavy chains as containing the most appropriate acceptor frameworks: IGKV1-39*01 for the light chain and IGHV1-2*02 for the heavy chain. The identified human heavy and light chain variable acceptor framework amino acid sequences are provided below:

$V_H$ amino acid sequence (AAP97932.1):
(SEQ ID NO: 43)
QVQLVQSGAEVKKPGASVKVSCKASGYTFTGYYMHWVRQAPGQGLEWMGW

INPNSGGTNYAQKFQGRVTMTRDTSISTAYMELSRLRSDDTAVYYCARTT

GTTYFDYWGQGTLVTVSS $V_L$ amino acid sequence (BAH04687.1):
(SEQ ID NO: 44)
DIQMTQSPSSLSASVCDRVTITCRASQSISSYLNWYQQKPGKAPKLLIYA

ASSLQSGVPSRFSGSGSGTDFTLTISSLQPEDFATYYCQQSYSTPLTFGG

GTKVEIR

Humanization of clone 371 was performed by CDR-grafting to the selected human frameworks (SEQ ID NOs: 3 and 4, for the heavy and light chains, respectively).

Homology modeling of the 371 antibody Fv fragments was carried out. Clone 371 sequences were BLAST searched Homology models were built using a customized Build Homology Models protocol. Disulfide bridges were specified and linked. Loops were optimized using the DOPE method. Based on the homology model of 1NMB, the sequences of reference antibody 371 were analyzed. Framework region (FR) residues that were believed to be important for the binding activity, i.e., canonical FR residues and $V_H$-$V_L$ interface residues of the antibody were identified. The framework residues in the inner core were analyzed further. Four residues of reference antibody 371_$Y_L$-1 (grafted reference antibody 371_$Y_L$; SEQ ID NO: 2) were identified for back mutation: K42 (buried residue with side chain charge), P44 (buried residue at $V_H$/$V_L$ interface), F71 (buried canonical residue), and Y87 (buried residue at $V_H$/$V_L$ interface). A humanized variant, reference antibody 371_$V_L$-2 (SEQ ID NO: 5), was designed to have the identified residues reverted to the reference antibody 371 residues (K42G, P44V, F71Y, and Y87F), in order to test if these were required to retain optimal activity.

Recombinant full human IgG4/kappa of humanized reference antibody 371 antibodies were constructed with human IgG4 containing the hinge S228P (EU numbering; Kabat numbering 241) stabilizing mutation (Angal et al., Mol. Immunol 30:105, 1993) and human kappa light chain constant region. The humanized reference antibody 371, clone 3711 is the CDR-grafted 371 of $V_H$-1 and $V_L$-1 without the back mutations, while clone 3712 has $V_H$-1 and $V_L$-2, which contains the back mutations of four amino acid residues counterparts (K42G, P44V, F71Y, and Y87F).

Additional humanized $V_H$ chains ($V_H$-2 ad $V_H$-3) and $V_L$ chain ($V_L$-3) were also constructed. The amino acid sequences of the $V_H$ and $V_L$ of the parent clone 371, and all humanized $V_H$ and $V_L$ chains derived therefrom are provided above.

Humanized anti-CD137 antibodies comprising a random combination of the humanized $V_H$ and $V_L$ chains listed above were constructed. See Table 3 below.

TABLE 3

V_H and V_L Chains of Anti-CD137 Antibody Clones

| Clone ID | VH | VL |
|---|---|---|
| 371 (chimera) | LYV371_V_H (SEQ ID NO: 1) | LYV371_V_L (SEQ ID NO: 2) |
| 3711 | LYV371_V_H1 (SEQ ID NO: 3) | LYV371_V_L-1 (SEQ ID NO: 4) |
| 3712 | LYV371_V_H1 (SEQ ID NO: 3) | LYV371_V_L-2 (SEQ ID NO: 5) |
| 3713 | LYV371_V_H1 (SEQ ID NO: 3) | LYV371_V_L-3 (SEQ ID NO: 10) |
| 3714 | LYV371_V_H2 (SEQ ID NO: 8) | LYV371_V_L-1 (SEQ ID NO: 4) |
| 3715 | LYV371_V_H2 (SEQ ID NO: 8) | LYV371_V_L-2 (SEQ ID NO: 5) |
| 3716 | LYV371_V_H2 (SEQ ID NO: 8) | LYV371_V_L-3 (SEQ ID NO: 10) |
| 3717 | LYV371_V_H3 (SEQ ID NO: 9) | LYV371_V_L-1 (SEQ ID NO: 4) |
| 3718 | LYV371_V_H3 (SEQ ID NO: 9) | LYV371_V_L-2 (SEQ ID NO: 5) |
| 3719 | LYV371_V_H3 (SEQ ID NO: 9) | LYV371_V_L-3 (SEQ ID NO: 10) |

The cDNA sequences encoding the anti-CD137 antibody variable domain sequences were synthesized as chimeras to human IgG4 heavy chain constant regions containing the hinge S228P (EU numbering; Kabat numbering 241) stabilizing mutation (Angal et al., Mol. Immunol 30:105, 1993) or human kappa light chain constant region. HEK293 and/or CHO transient expression was carried out with plasmids containing the corresponding heavy and light chain sequences. These chimeric and humanized antibodies were purified by protein affinity chromatography. The purified antibodies were checked for endotoxin (<5 EU/mg) and monomerization (>95%).

Example 2: Evaluation of Anti-CD137 Humanized Antibodies $K_D$ Measurement of CD137 Antigen Binding The chimeric and humanized antibodies were tested in an antigen binding assay on Octet Red 96 to estimate binding kinetics. Antibodies were loaded onto anti-human Fc (AHC) biosensors. Loaded sensors were dipped into a serial dilution of CD137 protein (300 nM, 1:3 down, 7 points) in assay buffer (PBS with 0.1% BSA, 0.02% Tween-20 (pH 7.2)). Kinetic constants calculated using a monovalent (1:1) model are shown in Table 4 below. Humanized antibody 3711 showed binding kinetics similar to the parental chimeric reference antibody 371. Antibody 3712, which has the back mutations, showed a lower affinity due to 3-fold higher off-rate.

TABLE 4

Kinetic Constants of Anti-CD137 Antibodies

| Antibody | $K_D$(M) | $k_{on}$(1/Ms) | $K_{dis}$(1/s) |
|---|---|---|---|
| 371 (chimera) | 3.9E−09 | 2.8E+05 | 1.1E−03 |
| 3711 (CDR grafted) | 2.4E−09 | 1.9E+05 | 4.6E−04 |
| 3712 (with back mutation) | 1.0E−08 | 3.1E+05 | 3.1E−03 |

CD137 Binding FACS

CHO cells over-expressing human CD137 were harvested using trypsin-EDTA partial digestion followed by centrifugation at 1000 g for 3 minutes. The cells were resuspended in cold PBS-BSA (2%) at $5 \times 10^6$/mL and aliquoted out to 100 µL/tube. The anti-CD137 antibodies were diluted in PBS-BSA in three times (final concentrations were 0.01, 0.1, 1, and 10 µg/mL) and 50 µL of each concentration was added to the CHO-CD137 cells. The cell solutions were mixed and incubated at 4° C. in the dark for 2 hours. The cells were then washed with PBS-BSA twice. Secondary antibody conjugates (goat F(ab')2 anti-human IgG-Fc (PE), pre-adsorbed (ab98596)) at a concentration of 1 µg/mL 100 µL/well was added and the cells were mixed and incubated 4° C. in dark for 1 hour. The cells were then washed twice with PBS-BSA, followed by fixation in 2% PFA, and were then subjected to FACS analysis. As shown in FIG. 1, reference antibody 371 and humanized antibody 3711 and 3712 exhibited similar binding affinity to the CHO cells over-expressing human CD137.

T Cell Functional Assays

Fresh PBMCs were isolated from four healthy volunteers and resuspended in PRMI-1640 containing 10% FBS at $1 \times 10^6$/mL. CD8$^+$ T cells were isolated from the samples using EasySep™ Human CD8$^+$ T Cell Isolation Kit (Stemcell, 17953). The resulting T cells were diluted into concentrations of $5 \times 10^5$/mL in RPMI 1640 (10% FBS).

Figure 2:
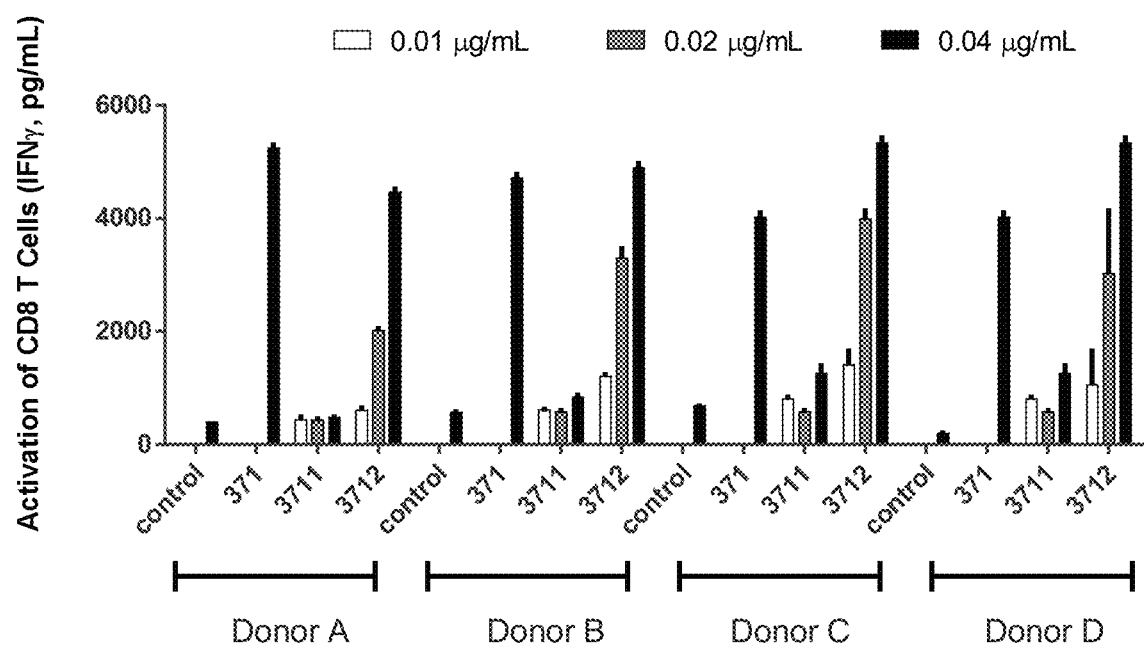
FIG. 2 is a bar graph depicting a comparison of reference antibody 371 and humanized antibodies 3711 and 3712 antibodies in a human $CD8^+$ T cell co-stimulation assay. Antibodies in serial dilution at final concentrations of 10, 20, and 40 ng/mL as shown were added to a plate in which human $CD8^+$ T cells were co-cultured with CHO-K1-huFcγRIIB cells. IFNγ concentration, shown on the y-axis, indicates activation of the human $CD8^+$ T cells.

Co-stimulation assays of human CD8-positive T cells were performed under co-culture with CHO cells expressing human FcγRIIB. To run co-culture assays, CHO cells engineered to express human FcγRIIB were plated in 96-well culture plates at a concentration of $2.5 \times 10^4$ cells/well. The cells were allowed to attach during an overnight incubation period in a cell culture incubator at 37° C. and 5% $CO_2$. Human CD8$^+$ T cells from four donors were added at $1 \times 10^5$ cells/well, OKT3 was added at 0.1 µg/mL, and CD137 antibodies were added at 0, 0.01, 0.02, and 0.04 µg/mL final concentration. The culture plates were incubated for 3 days in cell culture incubator at 37° C. and 5% $CO_2$. The IFN-γ content in the culture supernatants was determined by ELISA (eBioscience, 88-7316-88). As shown in FIG. 2, chimeric and humanized antibodies showed the ability to co-stimulate human CD8-positive T lymphocytes in the presence of FcγRIIB-expressing CHO cells. It was noted that, unexpectedly, antibody 3711 showed weaker potency than the parental reference antibody 371 and clone 3712 (back mutations). Therefore, clone 3712, the humanized antibody containing back mutations in the variable region of light chain, was selected as the desired humanization sequences for Fc engineering.

Example 3: Fc Engineering and Characterization of Anti-CD137 Humanized Antibodie s Preparation of Antibody Clone 3712 with Fc Point Mutations The humanized sequences of clone 3712 described above were used to construct CD137 antibody clone 3712 comprising an Fc region of human IgG1/kappa (SEQ ID NOs: 6 and 7), which contains an Fc variant of human IgG1 (clone 3712-IgG1v/kappa). Clone 3712 was cloned into expression vectors for production in transient expression CHO cells and in stable CHO cell lines.

$K_D$ Measurement of CD137 Antigen Binding on Biacore

Figure 3:
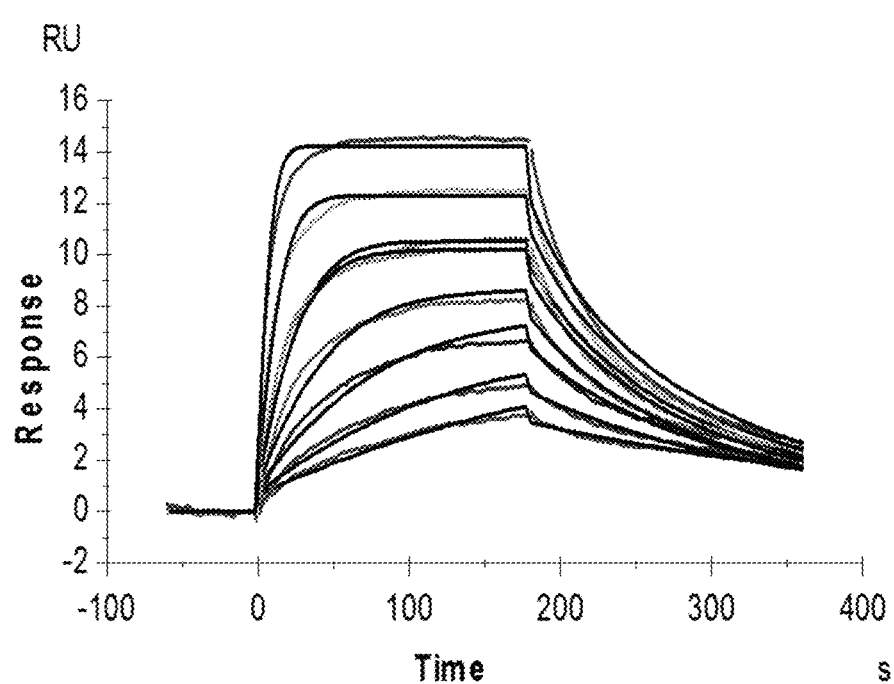
FIG. 3 is a line graph showing the binding of huCD137-C6His to clone 3712 on Biacore T200. Serially diluted clone 3712 (2.5, 5, 10, 20, 40, 80, 160, and 320 nM, in duplicate) was injected sequentially over flow cells with immobilized human CD137 protein with association time of 180 seconds; buffer flow was maintained for 180 seconds for dissociation.

Flow cells of a CMS sensor chip (GE Healthcare Life Sciences) were activated with freshly mixed 50 mmol/L NHS and 200 mmol/L EDC for 420 seconds (10 µL/min). Then, huCD137-C6His in 10 mmol/L NaAC (pH 5.0) was injected onto the activated flow cell (10 µL/min) with HBS-EP (10 mM HEPES, 150 mM NaCl, 3 mM EDTA and 0.05% P20, pH 7.4) as the running buffer. The remaining active coupling sites were blocked with a 420 second injection of 1 mol/L ethanolamine The measurement was performed under 25° C., and HBS-EP was used as the running buffer. An injection of a tested analyte and surface regeneration of the CMS sensor chip were included in each running cycle. Serially diluted clone 3712 (2.5, 5, 10, 20, 40, 80, 160, and 320 nM) was injected sequentially over both cells with an association time of approximately 180 seconds. Buffer flow was maintained for approximately 180 seconds for dissociation. To remove the tested antibodies, an injection of 10 mM glycine-HCl for approximately 30 seconds was used for regeneration. The above procedures were repeated for each concentration of serially diluted tested antibody. The raw data of the surface plasmon resonance experiments were evaluated using Biacore T200 evaluation software 3.1 with a 1:1 binding model. Flow cell 1 was used as the reference flow cell. The affinity and kinetics data of the experiment are shown in Table 5, and the raw data is provided in FIG. 3. The affinity ($K_D$ value) of clone 3712 and human CD137 protein was 18.9 nM, with a fast-on and fast-off kinetics.

TABLE 5

Kinetics Data (binding of clone 3712-IgG1v to human CD137 protein)

| Ligand | Analyte | $k_a$(1/Ms) | $k_d$(1/s) | $K_D$(M) | Rmax (RU) | Chi$^2$ (RU$^2$) |
|---|---|---|---|---|---|---|
| huCD137-C6His | Clone 3712-IgG1v | 7.30E+05 | 0.01379 | 1.89E−08 | 12.84 | 0.0936 |

$k_a$: association constant;
$k_d$: dissociation constant;
$K_D$: affinity constant CD137 Binding ELISA The binding of clone 3712-IgG1v with a recombinant CD137 receptor protein was also analyzed in standard ELISA format. The human or cynomolgus monkey CD137 receptor protein was diluted in DPBS to 1 μg/mL, and then coated onto an ELISA plate (Corning, Catalog number: 9018, high binding) with a volume of 100 μL (0.1 μg) or 50 μL (0.05 μg) per well, and incubated at 4° C. overnight. The plate was decanted and washed once; assay diluent was added 200 μL/well. After a one-hour incubation at room temperature, the plate was washed with PBST one time. Clone 3712 was diluted in assay diluent to 10 μg/mL, and then a 3-fold serial dilution in assay diluent for 11 points to final concentrations of 10000, 3333.3, 1111.1, 370.4, 123.5, 41.2, 13.7, 4.6, 1.52, 0.51 and 0.17 ng/mL. The diluted clone 3712-IgG1v was added to the assay plate, 50 μL/well, in duplicate. The plate was incubated one hour at room temperature and then washed three times with PBST. Goat anti-human IgG-H+L HRP conjugated at 1:100,000 dilution was added to the plate at 100 μL/well. The plate was then incubated one hour at room temperature followed by washing with PBST four times. The TMB substrate solution was added at 100 μL/well. The color was allowed to develop for 15 minutes, and was stopped with 100 μL/well 2N $H_2SO_4$. Absorbance at 450 nm and 620 nm was determined by a Tecan F200 Pro reader.

To determine if clone 3712-IgG1v binds mouse or rat CD137 receptors and other human proteins, such as human PD-1, LAG-3, VISTA, B7-H3, B7-H4, GITR, CD40, TIGIT, PD-L1, CD20, CD47, CD19, CD27 and LTBR, protein samples were diluted in DPBS to 1 μg/mL and then coated onto an ELISA plate (Corning, Catalog number: 9018, high binding) at 100 μL (0.1 μg) or 50 μL (0.05 μg) per well, and incubated at 4° C. overnight. The plate was decanted and washed once; assay diluent was added at 200 μL/well. After a 1-hour incubation at room temperature, the plate was washed with PBST one time. A target-specific antibody used as a positive reference/control was diluted in assay diluent to 10 μg/mL; clone 3712-IgG1v was diluted in assay diluent to 10 μg/mL and 1 μg/mL; a negative control, Avastin, was diluted in assay diluent to 10 μg/mL. These samples were added into the plate 50 μL/well. The plate was incubated 1 hour at room temperature and then washed three times with PBST. Goat anti-human IgG-H+L HRP-conjugated at 1:100,000 dilution or goat anti-mouse IgG (H+L) secondary antibody, HRP, at 1:50,000 dilution was added to the plate at 100 μL/well. The plate was incubated 1 hour at room temperature followed by washing with PBST four times. The TMB substrate solution was added 100 μL/well. The color was permitted to develop for 15 minutes and then 100 μL/well 2N $H_2SO_4$ was added to terminate the reaction. Absorbance at 450 nm and 620 nm was determined by a Tecan F200 Pro reader.

Figure 4A:
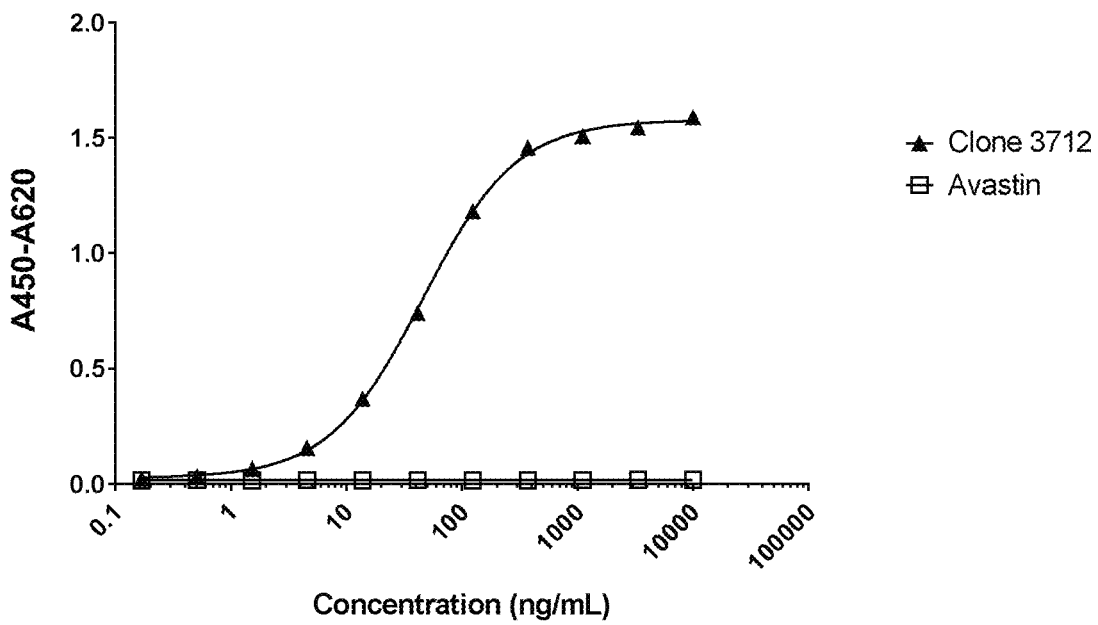
FIGS. 4A-4B are graphs showing the results of CD137 protein and humanized antibody 3712-binding ELISAs. Clone 3712 or Avastin (negative control) in serial dilution at final concentrations as shown on the x-axis were added to plates coated with recombinant human (FIG. 4A) or cyno (FIG. 4B) CD137 protein. Absorbance, shown on the y-axis, indicates antibody binding.
Figure 4B:
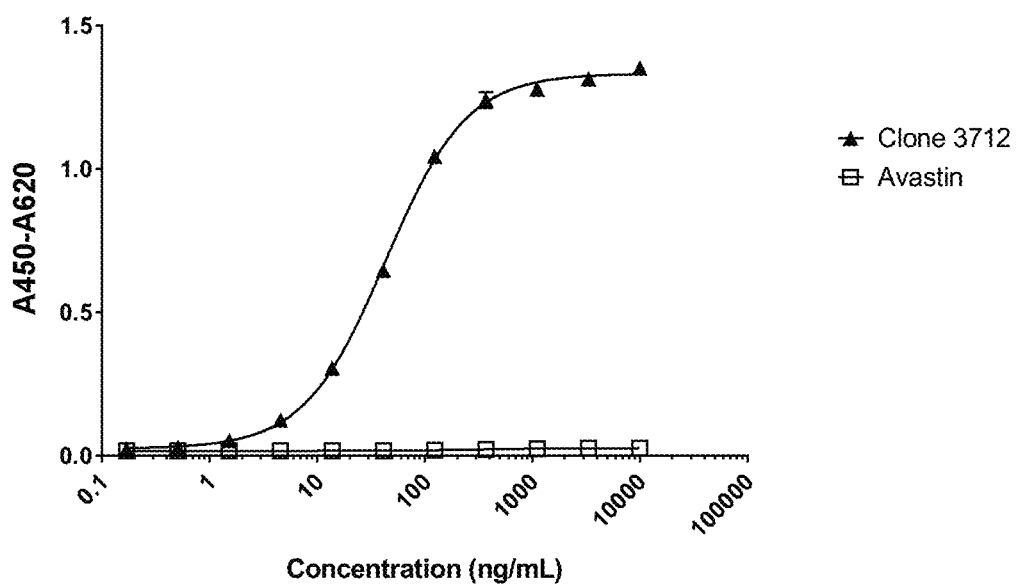

Graphpad 7.0, "[Agonist] vs. response—Variable slope (four parameters)" was used to plot the binding data and calculate binding $EC_{50}$ values. Representative data are shown in FIGS. 4A-4B. A summary of binding EC50 values is listed in Table 6. Avastin was used a control antibody for these assays. The results of these studies show that the average binding $EC_{50}$ values of clone 3712-IgG1v for human and cynomolgus monkey CD137 are 0.37 nM (i.e. 52.9 ng/mL) and 0.33 nM (i.e. 47.4 ng/mL), respectively. Clone 3712-IgG1v showed no binding affinity to mouse or rat CD137 protein.

Additionally, other human proteins, including PD-1, LAG-3, VISTA, B7-H3, B7-H4, GITR, CD40, TIGIT, PD-L1, CD20, CD47, CD19, CD27 and LT β R, were tested using ELISA assays to determine clone 3712-IgG1v binding. No binding affinity was observed. This study demonstrated the specific binding of clone 3712 to human and cyno CD137 receptors.

TABLE 6

Summary of ELISA Binding Results

| | Human CD137 Average EC50; n = 6 | Cyno CD137 Average EC50; n = 6 | Rodent CD137 | Other proteins* |
|---|---|---|---|---|
| Clone 3712-IgG1v | 0.37 nM (i.e. 52.9 ng/mL) | 0.33 nM (i.e. 47.4 ng/mL) | No affinity | No affinity |
| Avastin | No affinity | No affinity | No affinity | No affinity |

*proteins tested including PD-1, LAG-3, VISTA, B7-H3, B7-H4, GITR, CD40, TIGIT, PD-L1, CD20, CD47, CD19, CD27 and LTβR CD137 Binding FACS CHO cells over-expressing human or cynomolgus monkey CD137 and CHO parental cells were harvested by centrifugation at 1000 g for 3 minutes. The cells were resuspended in ice cold assay buffer at 2*10^6/mL and transferred to 96-well V-bottom plate with 100 μL/well. Clone 3712-IgG1v or Avastin antibody was diluted in assay buffer to 300 μg/mL, and then a 3-fold serial dilution in assay buffer was carried to prepare for 15 points with concentrations of 300000, 100000, 33333.3, 11111.1, 3703.7, 1234.6, 411.5, 137.2, 45.7, 15.2, 5.08, 1.69, 0.56, 0.19 and 0.063 ng/mL, 3× final concentration. The diluted clone 3712-IgG1v or Avastin was added to the assay plate at 50 μL/well. The plate was mixed and incubated in the dark for 2 hours at 4° C. The cells were washed 3 times by centrifugation at 1000 g for 3 min and resuspended in ice cold assay buffer containing goat F(ab')$_2$ anti-human IgG-Fc (PE), 100 μL/well. The plate was incubated in the dark for another 1 hour at 4° C. The cells were washed 2 times by centrifugation at 1000 g for 3 min and resuspended in ice cold assay buffer containing 2% PFA. The cells were then subjected to the flow cytometer immediately.

To determine if clone 3712-IgG1v binds the mouse CD137 receptor and other human cellular targets, such as human LAG-3, VISTA, B7-H3, B7-H4, GITR, CD40, TIGIT, PD-L1, CD20, CD47, CD19, CD27, LTBR, BTLA, CD160 and CD200R1, CHO cells over-expressing these targets were harvested by centrifugation at 1000 g for 3 minutes. The cells were resuspended in ice cold assay buffer at $2*10^6$/mL and transferred to 96-well V-bottom plate with 100 μL/well. Target-specific antibody was diluted in assay buffer at 30 μg/mL or 6 μg/mL, clone 3712-IgG1v was diluted in assay buffer at 30 μg/mL or 3 μg/mL, and Avastin was diluted in assay buffer at 30 μg/mL. The diluted target-specific antibody, clone 3712-IgG1v, or Avastin was added to the assay plate at 50 μL/well. The plate was incubated in the dark for 2 hours at 4° C. The cells were washed 3 times by centrifugation at 1000 g for 3 min and resuspended in 100 μL ice cold assay buffer containing goat F(ab')$_2$ anti-human IgG-Fc (PE) or PE goat anti-mouse IgG antibody. The plate was incubated in the dark for another 1 hour at 4° C. The cells were washed 2 times by centrifugation at 1000 g for 3 min and resuspended in ice cold assay buffer containing 2% PFA and analyzed on the flow cytometer immediately.

Figure 5A:
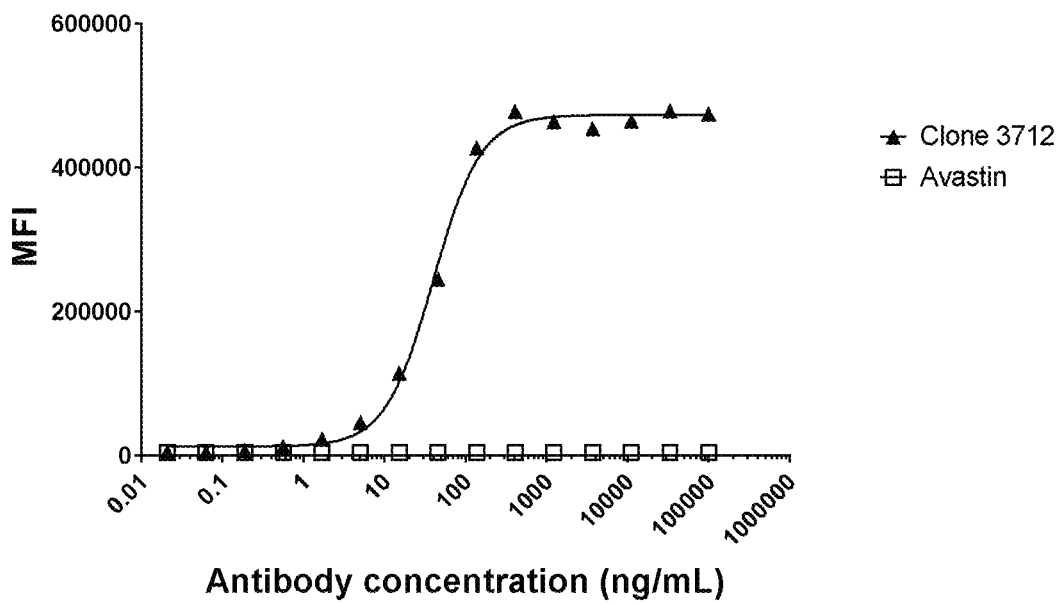
FIGS. 5A-5C are graphs depicting clone 3712 and cellular CD137 binding FACS. Clone 3712 or Avastin in serial dilution at final concentrations as shown on the x-axis were incubated with CHO-human CD137 (FIG. 5A), CHO-cyno-molgus monkey CD137 (FIG. 5B), or parental CHO (FIG. 5C) cells. Mean fluorescence intensity (MFI), shown on the y-axis, indicates antibody binding.
Figure 5B:
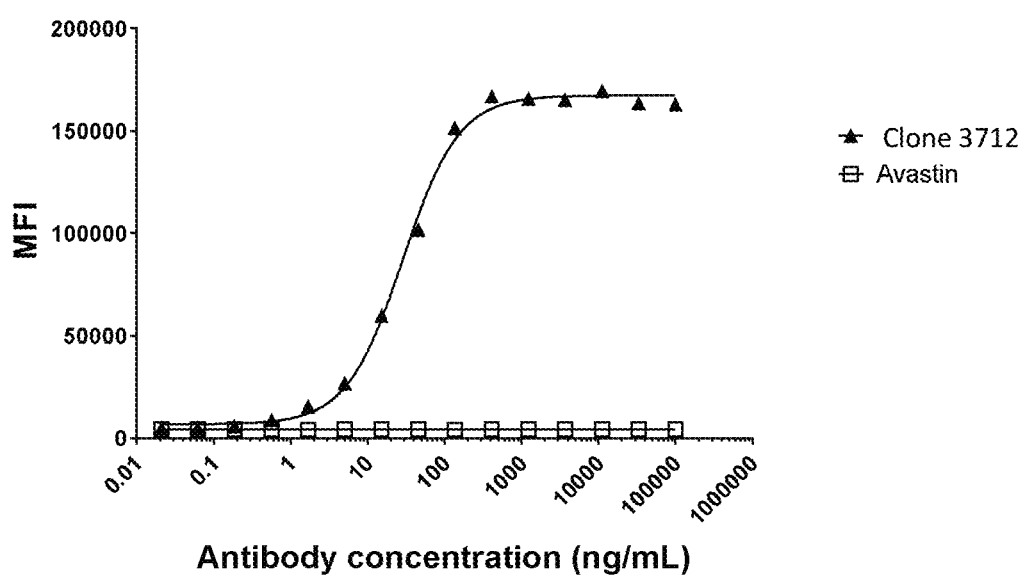
Figure 5C:
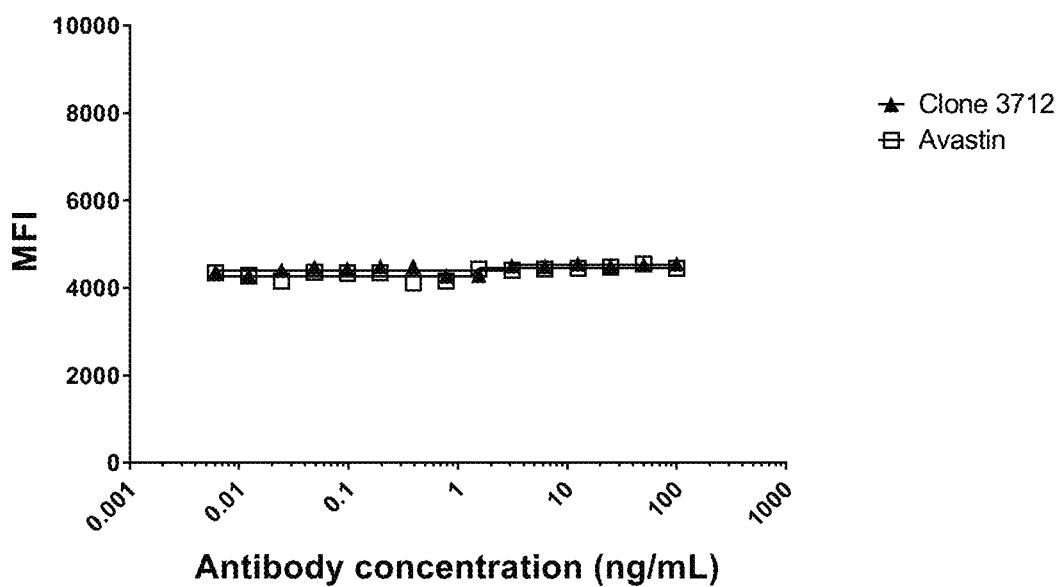

Mean fluorescence intensity (MFI) was calculated from the total cell population in the FCM experiments. Graphpad 7.0, "[Agonist] vs. response—Variable slope (four parameters)" was used to plot the binding MFI in dose response and to calculate FCM binding $EC_{50}$ values. Clone 3712-IgG1v showed potent binding to both human and cynomolgus monkey CD137 overexpressed on CHO by FCM. No binding was seen with the parental CHO cells. The reference antibody Avastin was used as a control to show specificity of the CD137 binding. Representative data are shown in FIGS. 5A-5C, and the results summarized in Table 7.

TABLE 7

Summary of FCM analysis of clone 3712 in CHO expression system

|  | Human CD137 Average EC50 n = 6 | Cyno CD137 Average EC50 n = 6 | Mouse CD137 | Other receptors* |
|---|---|---|---|---|
| Clone 3712-IgG1v | 0.35 nM (i.e. 49.7 ng/mL) | 0.26 nM (i.e. 36.9 ng/mL) | No binding | No binding |
| Avastin | No binding | No binding | No binding | No binding |

*Other receptors tested including LAG-3, VISTA, B7-H3, B7-H4, GITR, CD40, TIGIT, PD-L1, CD20, CD47, CD19, CD27, LTBR, BTLA, CD160, CD200R1 and PD-1.

To demonstrate the specificity of clone 3712-IgG1v for CD137, CHO cells over-expressing other human receptor proteins, such as LAG-3, VISTA, B7-H3, B7-H4, GITR, CD40, TIGIT, PD-L1, CD20, CD47, CD19, CD27, LTBR, BTLA, CD160, CD200R1 and PD-1, were tested by FCM. No binding signal was observed for clone 3712, consistent with the specificity demonstrated in the protein ELISA experiments described above. As expected from the ELISA data, clone 3712-IgG1v did not bind murine cellular CD137.

Binding to Endogenous CD137 on Activated CD8$^+$ T Cells

To ascertain that clone 3712-IgG1v can bind endogenous human and cynomolgus monkey CD137, PBMCs activated by immobilized anti-CD3 antibodies were examined for binding. To obtain activated T cells in human PBMC, a 24-well plate was coated with 300 μL DPBS containing 2 μg/mL AffiniPure goat anti-mouse IgG, Fcγ fragment specific at 4° C. overnight. The plate was washed 3 times with DPBS. The antibody OKT3 was added to the plate at 1 μg/mL, 100 μL/well. The plate was incubated at 37° C. for 1 hour. A freshly thawed vial of human PBMCs was transferred into a 50 mL tube containing 25 mL pre-warmed culture medium (RPMI1640 containing 10% FBS), and spun at 250 g for 10 min The cell pellet was resuspended in 2 mL complete culture medium (culture medium containing 50 uM 2-Me) and the cell density was adjusted to $3.3*10^6$ cells/mL in the complete culture medium and then 900 μL/well cell suspension was transferred to the plate. The culture was incubated at 37° C. with 5% CO$_2$ for about 48 hours. After the incubation, the cells were harvested and washed once with DPBS. The cell pellet was resuspended in cold assay buffer and the cell density was adjusted to $2*10^6$ cells/mL. 100 μL of the cell suspension was transferred to a 96-well v-bottom plate. Clone 3712-IgG1v or the Avastin antibody was diluted in assay buffer to 300 μg/mL, and then a 10-fold serial dilution in assay buffer was carried out to prepare concentrations of 300000, 30000, 3000, 300, 30, 3, 0.3 and 0.03 ng/mL, 3× final concentration. The diluted clone 3712-IgG1v or Avastin was added to the assay plate at 50 μL/well. The plate was incubated in the dark for 30 minutes at 4° C. The cells were washed 3 times by centrifugation at 1000 g for 3 min and resuspended in 50 μL ice cold assay buffer containing FITC anti-human CD3 antibody, PE anti-human CD8a antibody and APC anti-human IgG Fc antibody. The plate was incubated in the dark for another 30 minutes at 4° C. Then, the cells were washed 2 times by centrifugation at 1000 g for 3 min and resuspended in 100 μL ice cold assay buffer containing 7-AAD. After incubation in the dark for 5 minutes at 4° C., the cells were analyzed on the flow cytometer immediately.

To obtain activated T cells in PBMC of cynomolgus monkeys, a 24-well plate was coated with 300 μL DPBS containing 2 μg/mL AffiniPure F(ab')2 fragment goat anti-human IgG, Fcγ fragment specific at 4° C. overnight. The plate was washed 3 times by DPBS. An anti-CD3 antibody, Ly305, capable of binding and activating cynomolgus monkey CD3 was added to the plate at 3 μg/mL, 100 μL/well. The plate was incubated at 37° C. for 1 hour. A freshly thawed vial of cynomolgus monkey PBMCs were transferred into a 50 mL tube containing 15 mL pre-warmed culture medium (RPMI1640 containing 10% FBS), and spun at 250 g for 10 min. The cell pellet was resuspended in 2 mL culture medium and adjusted to cell density of $3.3*10^6$ cells/mL in complete culture medium and transferred 900 μL/well cell suspension into the plate. The culture was incubated at 37° C. with 5% CO$_2$ for about 48 hours. After the incubation, the cells were harvested and washed once by DPBS. The cell pellet was resuspended in cold assay buffer and the cell density was adjusted to $2*10^6$ cells/mL. A 100 μL cell suspension was transferred to a 96-well v-bottom plate. Clone 3712-IgG1v-Biotin or Avastin-Biotin antibody was diluted in assay buffer to 300 μg/mL, and then a 10-fold serial dilution in assay buffer was carried out to prepare concentrations of 300000, 30000, 3000, 300, 30, 3, 0.3 and 0.03 ng/mL, 3× final concentration. The diluted clone 3712-IgG1v-Biotin or Avastin-Biotin was added to the assay plate at 50 μL/well. The plate was incubated in the dark for 60 minutes at 4° C. The cells were washed 3 times by centrifugation at 1000 g for 3 min and resuspended in 50 μl ice cold assay buffer containing FITC anti-human CD8 Antibody (clone: SK1) and APC Streptavidin. The plate was incubated in the dark for another 60 minutes at 4° C. Then, the cells were washed 2 times by centrifugation at 1000 g for 3 min and resuspended in 100 μL ice cold assay buffer containing 7-AAD. The plate was incubated in the dark for 5 minutes at 4° C. and then analyzed on the flow cytometer immediately.

Figure 6A:
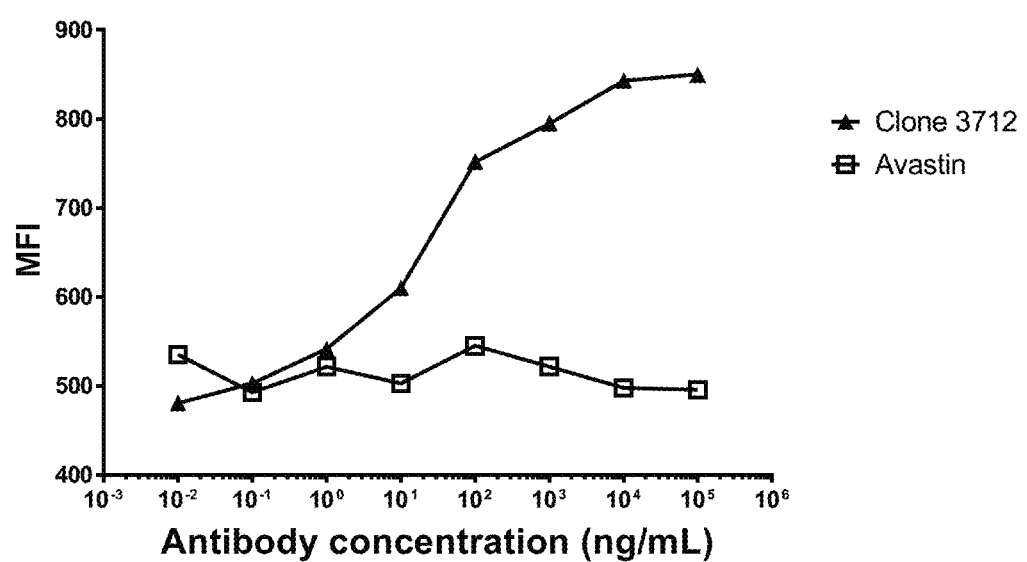
FIGS. 6A-6B are graphs depicting clone 3712 binding to endogenous CD137 on activated CD8 T cells by FACS. Clone 3712 or Avastin in serial dilution at final concentrations as shown on the x-axis were incubated with human (FIG. 6A) or cynomolgus monkey (FIG. 6B) PBMC preactivated by anti-CD3 antibodies. Mean fluorescence intensity (MFI) of CD8+ T cells, shown on the y-axis, indicates antibody binding.
Figure 6B:
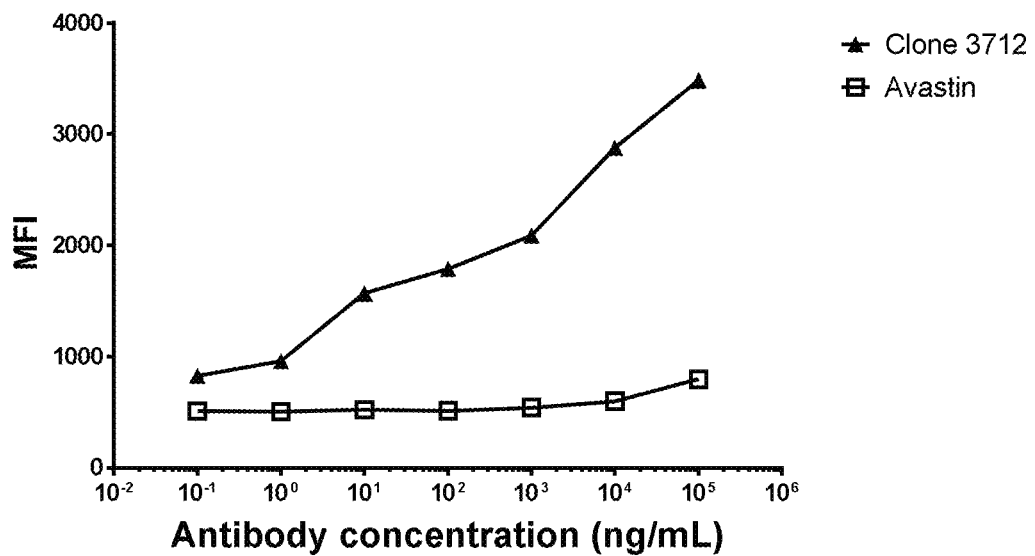

As shown in FIGS. 6A-6B, clone 3712-IgG1v showed dose-dependent binding to activated human or cynomolgus monkey CD8$^+$ T cells. It was found that clone 3712-IgG1v binds to human and cynomolgus monkey cellular CD137 receptor with similar $EC_{50}$ values (37-50 ng/mL or ~0.3 nM). Clone 3712-IgG1v was also found to bind to endogenous CD137 on activated CD8$^+$ T cells of human or cynomolgus monkey in a dose-dependent manner. Therefore, clone 3712 shows high specificity for CD137 by FCM as expected from the ELISA studies described herein.

Fc Receptors and Complement C1q Binding

FcγRI Binding Assay

CHO-K1-huFcγRI cells were harvested by centrifugation at 1000 g for 3 minutes. The cells were resuspended in ice cold assay buffer at 2*10^6/mL and transferred to a 96 well V bottom plate at 100 μL/well. Clone 3712-IgG1v or Avastin antibody was diluted in assay buffer to 30 μg/mL, and then a 2-fold serial dilution in assay buffer was carried to prepare for 15 points with concentrations of 30000, 15000, 7500, 3750, 1875, 937.5, 468.8, 234.4, 117.2, 58.6, 29.3, 14.6, 7.32, 3.66 and 1.83 ng/mL, 3× final concentration. The diluted clone 3712-IgG1v or Avastin was added to the assay plate at 50 μL/well. The plate was mixed and incubated in the dark for 2 hours at 4° C. The cells were washed 3 times by centrifugation at 1000 g for 3 min and resuspended in ice cold assay buffer containing goat F(ab')$_2$ anti-human IgG-Fc (PE) secondary antibody 100 μL/well. The plate was incubated in the dark for another 1 hour at 4° C. The cells were washed 2 times by centrifugation at 1000 g for 3 min and resuspended in ice cold assay buffer containing 2% PFA. The cells were subjected to flow cytometry analysis immediately.

Figure 7A:
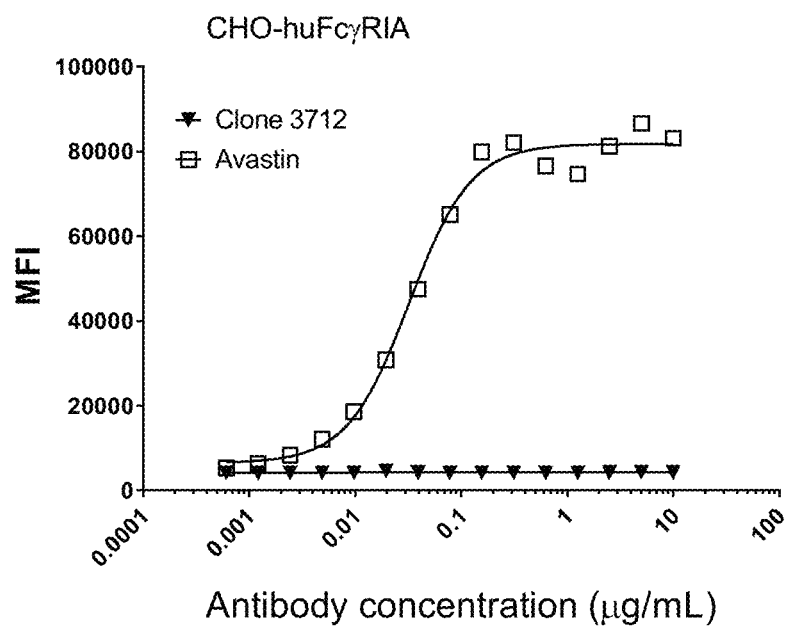
FIGS. 7A-7E are graphs showing FACS analysis of clone 3712 binding to CHO cells over-expressing human Fcγ receptors. Clone 3712 or Avastin in serial dilution at final concentrations (10, 5, 2.5, 1.25, 0.625, 0.3125, 0.1563, 0.078, 0.039, 0.0195, 0.0098, 0.0049, 0.0024, 0.0012 and 0.0006 μg/mL), as shown on the x-axis, were incubated with CHO-huFcγ receptors cells: CHO-huFcγRIA (FIG. 7A), CHO-huFcγRIIA-R131 (FIG. 7B), CHO-huFcγRIIA-H131 (FIG. 7C), CHO-huFcγRIIB (FIG. 7D), and CHO-huFcγRIIIA (FIG. 7E). Mean fluorescence intensity (MFI), shown on the y-axis, indicates antibody binding.

CHO-K1-huFcγRI cells express high levels of the human FcγRI, which has high affinity for IgG1 (Ravetch and Bolland 2001, Roopenian and Akilesh 2007), were used for FcγRI binding assay for clone 3712-IgG1v. Binding was examined through multiple concentrations of antibody, including 10, 5, 2.5, 1.25, 0.625, 0.3125, 0.1563, 0.078, 0.039, 0.0195, 0.0098, 0.0049, 0.0024, 0.0012 and 0.0006 μg/mL (from top 10 μg/mL, 2-fold serial dilution, 15 dilution points). Binding was detected by flow cytometry using a PE conjugated, polyclonal, anti-human Fc F(ab')$_2$ fragment. Three independent experiments were run. FIG. 7A shows representative data of clone 3712-IgG1v exhibiting no binding to FcγRI, while the reference human IgG1 antibody, Avastin, showed high binding affinity with an $EC_{50}$ value of 32.2 ng/mL (~0.2 nM).

FcγRIIA Binding Assay

CHO-K1-huFcγRIIA-Arg131 and CHO-K1-huFcγRIIA-His131 cells were harvested by centrifugation at 1000 g for 3 minutes. The cells were resuspended in ice cold assay buffer at 2*10^6/mL and transferred to a 96 well V bottom plate at 100 μL/well. Clone 3712-IgG1v or Avastin antibody was diluted in assay buffer to 300 μg/mL, and then a 2-fold serial dilution in assay buffer was undertaken to prepare concentrations of 300000, 150000, 75000, 37500, 18750, 9375, 4688, 2344, 1172, 586, 293, 146, 73.2, 36.6 and 18.3 ng/mL, 3× final concentration. The diluted clone 3712-IgG1v or Avastin was added to the assay plate at 50 μL/well. The plate was mixed and incubated in the dark for 2 hours at 4° C. The cells were washed 3 times by centrifugation at 1000 g for 3 min and resuspended in ice cold assay buffer containing goat F(ab')$_2$ anti-human IgG-Fc (PE) secondary antibody at 100 μL/well. The plate was incubated in the dark for another hour at 4° C. The cells were washed twice by centrifugation at 1000 g for 3 min and resuspended in ice cold assay buffer containing 2% PFA. The cells were subjected to flow cytometry immediately.

Figure 7B:
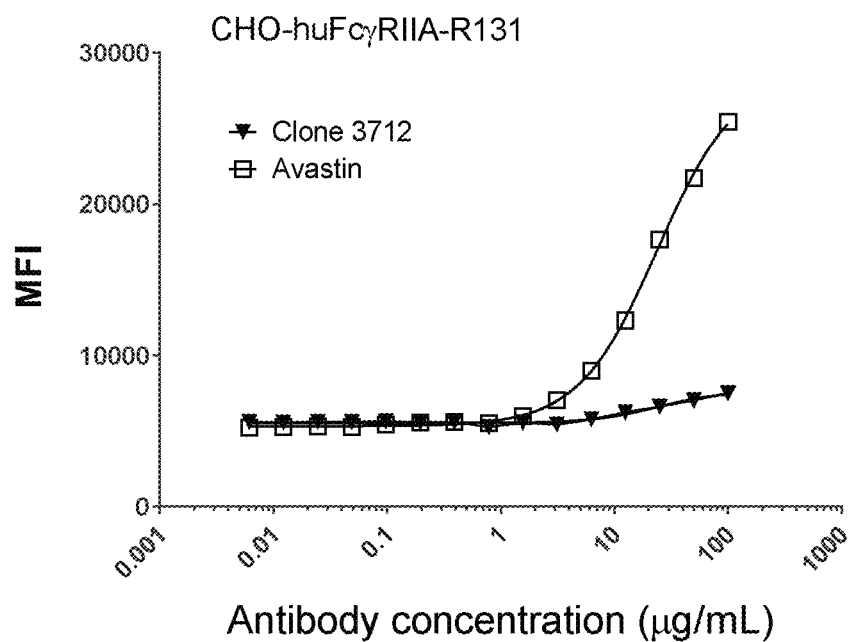
Figure 7C:
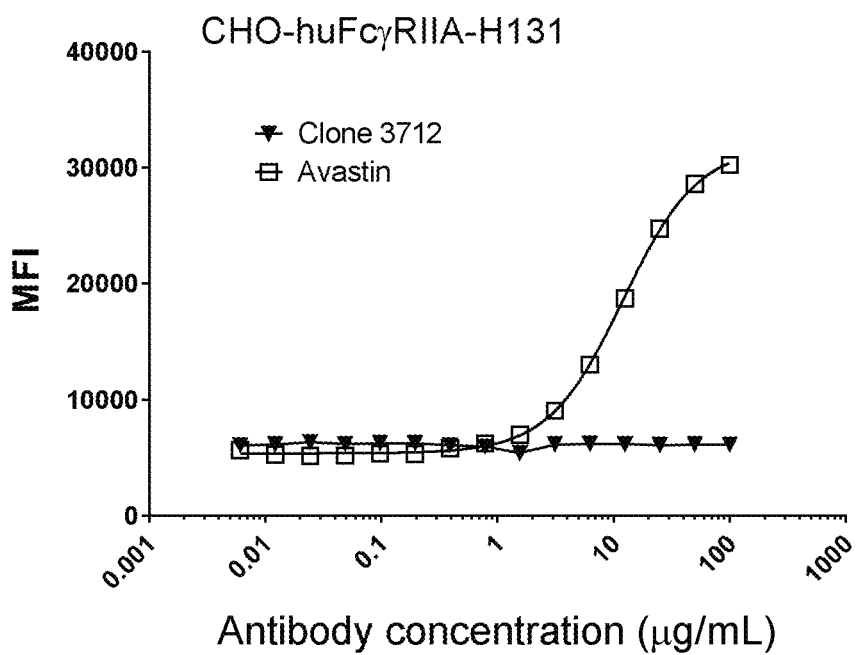

CHO-K1-huFcγRIIA-Arg131 and CHO-K1-huFcγRIIA-His131 cells express the activating FcγRIIA receptor, which has a low binding affinity for IgG1. Both were investigated for the FcγRIIA binding assay. Binding was examined in a range of concentrations including: 100, 50, 25, 12.5, 6.25, 3.125, 1.56, 0.78, 0.39, 0.195, 0.098, 0.049, 0.024, 0.012 and 0.006 μg/mL (from top 100 μg/mL, 2-fold serial dilution, 15 dilution points). Binding was again detected by flow cytometry using a PE-conjugated, polyclonal, anti-human Fc F(ab')$_2$ fragment. At least three independent experiments were run. FIGS. 7B and 7C show representative data of clone 3712-IgG1v, which exhibited weak binding to huFcγRIIA-Arg131 and no binding to huFcγRIIA-His131. The reference control, Avastin, demonstrated moderate binding in both assays, as expected for a normal human IgG1.

FcγRIIB Binding Assay

CHO-K1-huFcγRIIB-Ile232 cells were harvested by centrifugation at 1000 g for 3 minutes. The cells were resuspended in ice cold assay buffer at 2*10^6/mL and transferred to a 96 well V bottom plate at 100 μL/well. Clone 3712-IgG1v or Avastin antibody was diluted in assay buffer to 300 μg/mL, and then a 2-fold serial dilution in assay buffer was used to prepare concentrations of 300000, 150000, 75000, 37500, 18750, 9375, 4688, 2344, 1172, 586, 293, 146, 73.2, 36.6 and 18.3 ng/mL, 3× final concentration. The diluted clone 3712 or Avastin was added to the assay plate at 50 μL/well. The plate was mixed and incubated in the dark for 2 hours at 4° C. The cells were washed 3 times by centrifugation at 1000 g for 3 min and resuspended in ice cold assay buffer containing goat F(ab')$_2$ anti-human IgG-Fc (PE) secondary antibody at 100 μL/well. The plate was incubated in the dark for another hour at 4° C. The cells were washed twice by centrifugation at 1000 g for 3 min and resuspended in ice cold assay buffer containing 2% PFA. The cells were subjected to flow cytometry immediately.

Figure 7D:
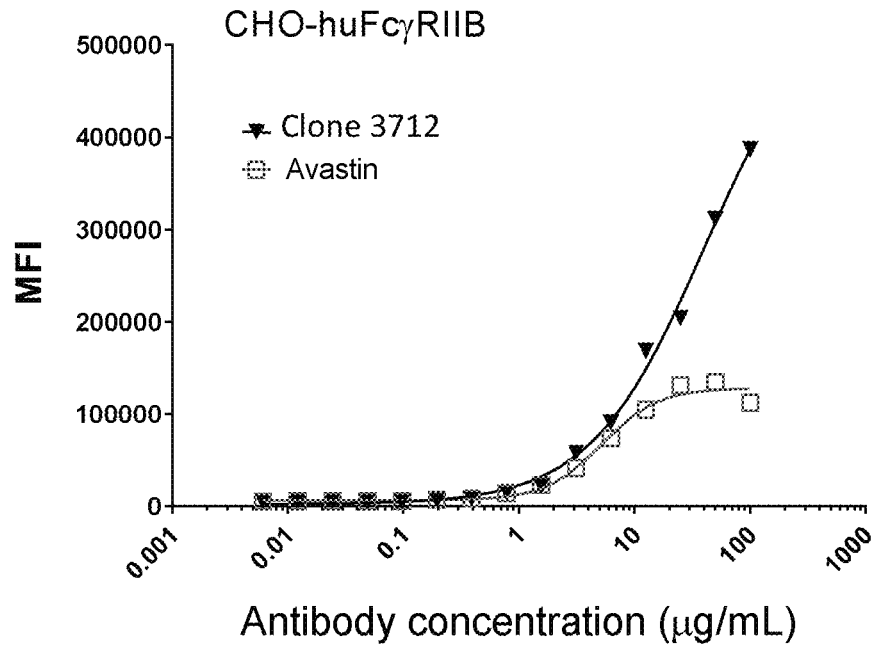

A transfected CHO cell line, CHO-K1-huFcγRIIB-Ile232, comprising cells expressing high levels of FcγRIIB, was used for the FcγRIIB binding assay. Test concentrations included the following: 100, 50, 25, 12.5, 6.25, 3.125, 1.56, 0.78, 0.39, 0.195, 0.098, 0.049, 0.024, 0.012, and 0.006 μg/mL (from top 100 μg/mL, 2-fold serial dilution, 15 dilution points). Binding by the test antibody was detected by polyclonal, anti-human Fc F(ab')$_2$ fragment. At least three independent experiments were performed and representative data is shown in FIG. 7D. Clone 3712-IgG1v and Avastin showed moderate binding affinity to human FcγRIIB while clone 3712-IgG1v did not show saturation at high concentrations (50 and 100 μg/mL), in contrast to Avastin.

FcγRIIIA Binding Assay

CHO-K1-huFcγRIIIA-Phe158 cells were harvested by centrifugation at 1000 g for 3 minutes. The cells were resuspended in ice cold assay buffer at 2*10^6/mL and transferred to a 96 well V bottom plate with 100 μL/well. Clone 3712-IgG1v or Avastin antibody was diluted in assay buffer to 300 μg/mL, and then a 2-fold serial dilution in assay buffer was undertaken to prepare final concentrations of 300000, 150000, 75000, 37500, 18750, 9375, 4688, 2344, 1172, 586, 293, 146, 73.2, 36.6 and 18.3 ng/mL, 3× final concentration. The diluted clone 3712-IgG1v or Avastin was added to the assay plate at 50 μL/well. The plate was mixed and incubated in the dark for 2 hours at 4° C. The cells were washed 3 times by centrifugation at 1000 g for 3 min and resuspended in ice cold assay buffer containing goat F(ab')2 anti-human IgG-Fc (PE) secondary antibody at 100 μL/well. The plate was incubated in the dark for another hour at 4° C. The cells were washed twice by centrifugation at 1000 g for 3 min and resuspended in ice cold assay buffer containing 2% PFA. The cells were subjected to flow cytometry immediately.

Figure 7E:
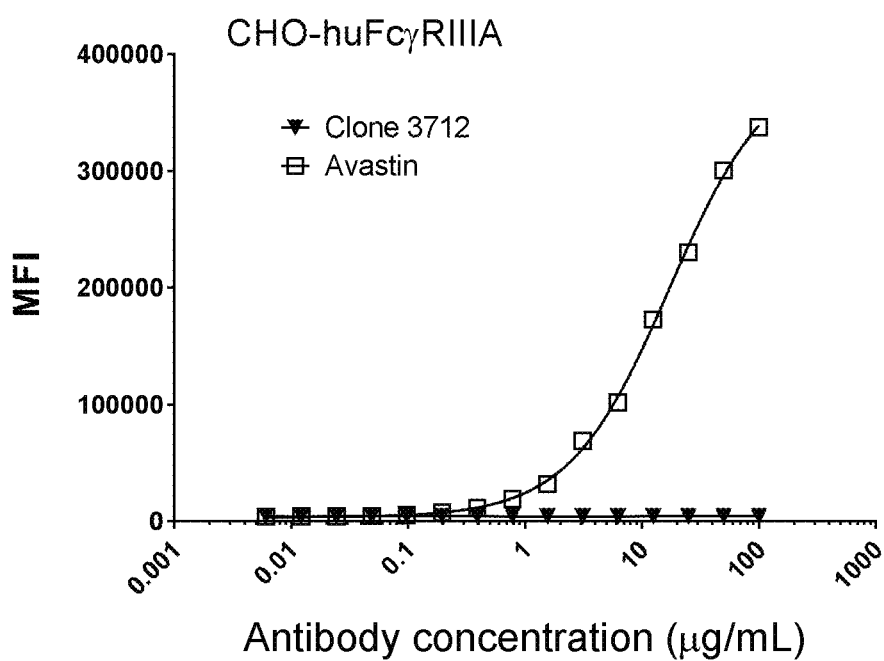

CHO-K1-huFcγRIIIA-Phe158 cells express high levels of the human FcγRIIIA, which has a relatively high affinity for IgG1. As such, the cells were used for the FcγRIIIA binding assay. Binding was examined through multiple concentrations of antibody: 100, 50, 25, 12.5, 6.25, 3.125, 1.56, 0.78, 0.39, 0.195, 0.098, 0.049, 0.024, 0.012 and 0.006 μg/mL (from top 100 μg/mL, 2-fold serial dilution, 15 dilution points). Binding was detected by flow cytometry using a PE-conjugated, polyclonal, anti-human Fc F(ab')2 fragment. Three independent experiments were run. FIG. 7E shows representative data demonstrating that clone 3712-IgG1v has no detectable binding to FcγRIIIA, while the reference human IgG1 antibody, Avastin, showed the expected moderate binding.

FcRn Binding Assay

Clone 3712-IgG1v and a control IgG1 monoclonal antibody (Avastin) were diluted in DPBS to 1 μg/mL and coated onto an ELISA plate (Corning, Catalog number: 9018, high binding) at 100 μL/well overnight at 4° C. The plate was decanted and washed once; assay diluent was added at 200 μL/well. After a 1-hour incubation at room temperature, the plate was washed with PBST (pH 6.0) once. Human FcRn protein was diluted in assay diluent (pH 6.0) to 10 μg/mL, and then a 2-fold serial dilution in assay diluent (pH 6.0) was carried out to prepare final concentrations of 10000, 5000, 2500, 1250, 625, 312.5 and 156.25 ng/mL. The diluted FcRn protein was added to the assay plate at 50 μL/well in duplicate. The plate was incubated 1 hour at room temperature and then washed three times with PBST (pH 6.0). Mouse anti-His tag antibody, HRP-conjugated, at a 1:20,000 dilution (pH 6.0) was added to the plate at 100 μL/well. The plate was incubated 1 hour at room temperature followed by washing with PBST (pH 6.0) four times. The TMB substrate solution was added at 100 μL/well. The color was developed for 12 minutes and then 100 μL/well 2N $H_2SO_4$ was added to terminate the reaction. Absorbance at 450 nm and 620 nm was determined by Tecan F200 Pro reader.

Figure 8A:
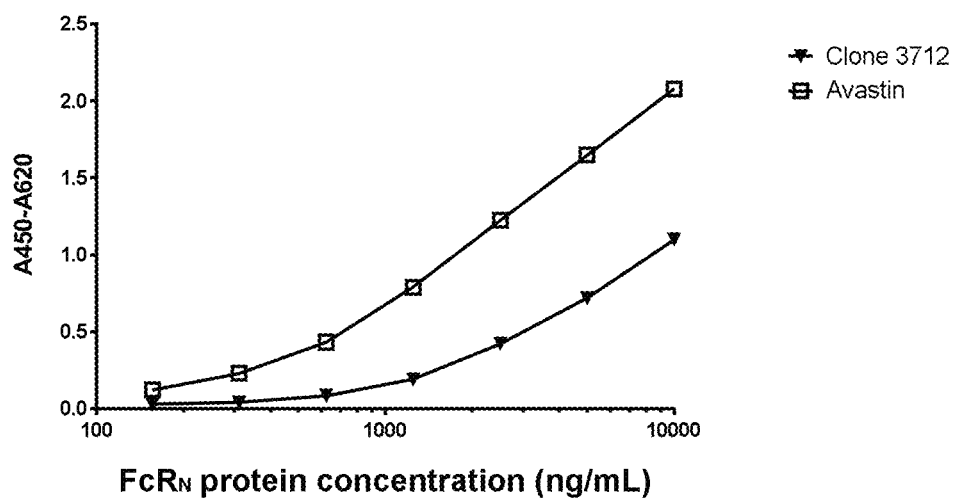
FIGS. 8A-8B are graphs showing the binding of clone 3712 to FcRn (FIG. 8A) and to C1q (FIG. 8B), as measured by ELISAs.

The binding of FcRn to clone 3712-IgG1v and human IgG1 Avastin was determined by ELISA. Clone 3712-IgG1v and Avastin were coated separately onto plastic ELISA plates followed by incubation with human FcRn protein with a His tag at concentrations of 10000, 5000, 2500, 1250, 625, 312.5, and 156.3 ng/mL (2-fold serial dilution, 7 dilution points). FcRn bound to coated antibody was detected by the anti-His tag-HRP antibody. Three independent experiments were performed and representative data is shown in FIG. 8A. Clone 3712-IgG1v demonstrated expected binding to FcRn, although with a weak signal intensity as compared to that of the reference antibody Avastin. Biacore binding of 3712 and human FcRn was also performed and the results confirmed positive binding with kinetics similar to human IgG1 and IgG4.

C1q ELISA

Clone 3712 and a control IgG1 monoclonal antibody (Avastin) were diluted in DPBS to 8, 4, 2, 1, 0.5, 0.25 and 0.125 μg/mL and was coated onto an ELISA plate (Corning, Catalog number: 9018, high binding) 100 μL/well in duplicate, 4° C. overnight. The plate was decanted and washed once; assay diluent was added 200 μL/well. After a 1-hour incubation at room temperature, the plate was washed with PBST one time. Human C1q protein was diluted in assay diluent to 2 μg/mL. The diluted C1q protein was added to the assay plate 50 μL/well. The plate was incubated 1 hour at room temperature and then washed three times with PBST. Sheep anti-human C1q antibody HRP-conjugated at a 1:800 dilution was added to the plate at 100 μL/well. The plate was incubated 1 hour at room temperature followed by washing with PBST four times. The TMB substrate solution was added at 100 μL/well. The color was developed for 7 minutes, and the 100 μL/well 2N $H_2SO_4$ was added to terminate the reaction. Absorbance at 450 nm and 620 nm was determined by Tecan F200 Pro reader.

Figure 8B:
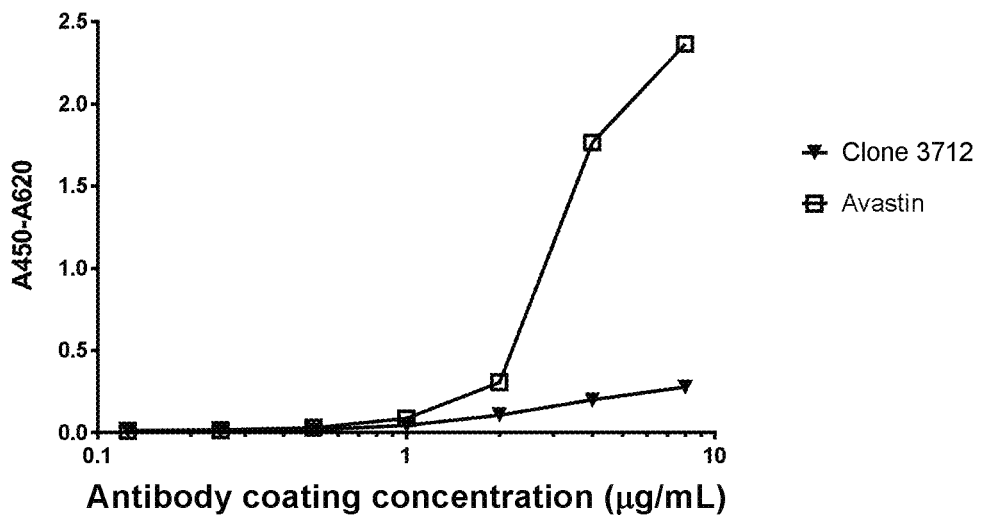

Complement activation and lysis of cells via the classical pathway is initiated through binding of C1q to the Fc portion of an IgG molecule. The binding of C1q to clone 3712-IgG1v and human IgG1 Avastin was determined by ELISA. Clone 3712-IgG1v and Avastin were coated separately onto plastic ELISA plates at multiple concentrations: 0.125, 0.25, 0.5, 1, 2, 4, and 8 μg/mL, followed by incubation with recombinant human C1q with a His tag at a concentration of 2 μg/mL. C1q bound to antibody was detected by the anti-human C1q-HRP antibody. Three independent experiments were performed and the representative data are shown in FIG. 8B. Clone 3712-IgG1v showed reduced binding to C1q as compared to the reference antibody Avastin.

Clone 3712-IgG1v is a humanized recombinant IgG1/κ with point-mutations in the Fc region that has been engineered to reduce binding to C1q and the activating Fcγ receptors to minimize Fc effector activity. The engineered Fc was designed to retain binding to FcRγIIB and FcRn. Experiments described here demonstrated that clone 3712 showed no or minimal binding to human FcγRI, FcγRIIA-Arg131, FcγRIIA-His131, FcγRIIIa, and complement C1q, whereas the reference human IgG1 antibody Avastin showed the binding profile as expected from literature. Clone 3712 exhibited binding to human FcγRIIB and FcRn. The results are consistent with the expected profile of the engineered Fc in clone 3712-IgG1v: retaining binding to human FcγRIIB and FcRn, but losing binding to other Fc receptors and C1q.

Activation of CD137 Signaling in Reporter Assays

CHO-K1 or CHO-K1-huFcγRIIB-Ile232 cells were harvested by centrifugation at 250 g for 5 minutes. The cells were resuspended in pre-warmed F12K medium containing 1% FBS at 2.5*10^6 cells/mL and transferred to a 96 well cell culture plate at 100 μL/well. Meanwhile, 100 μL/well F12K medium containing 1% FBS was added to a third cell culture plate. DPBS was added to the edge of the cell culture plate. The plate was incubated at 37° C. in 5% $CO_2$ overnight. The next day, GS-H2-huCD137 cells were harvested following centrifugation at 250 g for 5 minutes. The GS-H2-huCD137 cells were resuspended in pre-warmed MEM medium containing 1% FBS at 6*10^4 cells/mL, and 50 μL/well of cell suspension was added to the cell culture plate. Clone 3712-IgG1v or Avastin antibody was diluted in MEM medium containing 1% FBS to 25 μg/mL, and then a 4-fold serial dilution in assay buffer was carried out to prepare final concentrations of 25000, 6250, 1562.5, 390.625, 97.65625, 24.414, 6.104, 1.526, 0.381, 0.095, and 0.024 ng/mL. The diluted clone 3712-IgG1v or Avastin was added to the cell culture plate at 50 μL/well. The plate was mixed and incubated at 37° C., in 5% $CO_2$ for about 18 hours. After the incubation, the cell culture supernatant was subjected for IL-8 detection using a human IL-8 assay kit from Cisbio.

Figure 9:
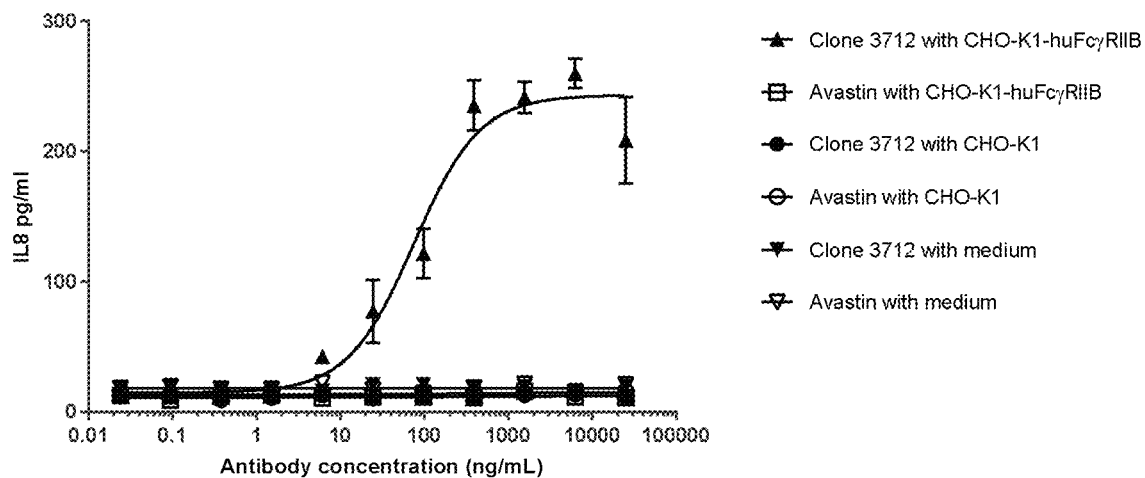
FIG. 9 is a graph showing the results of a CD137 reporter activity assay. Clone 3712 or Avastin in serial dilution at final concentrations at concentrations of 25000, 6250, 1562.5, 390.6, 97.7, 24.4, 6.10, 1.53, 0.381, 0.095, and 0.024 ng/mL, as shown on the x-axis, were added to a plate in which CD137 reporter cells were co-cultured with CHO-K1-huFcγRIIB, CHO-K1, or medium without cells. IL-8 concentration, shown on the y-axis, indicates activation of the CD137 reporter cells.

Clone 3712-IgG1v showed dose-dependent agonistic activity under crosslinking conditions. When the CD137 reporter cells were co-cultured with CHO-K1-huFcγRIIB cells, clone 3712 induced CD137 activation, leading to IL8 secretion from the reporter cells. Clone 3712-IgG1v did not activate CD137 without crosslinking (co-culture with the control CHO cells or no co-culture). Avastin was used as a control to show the specificity of the CD137 activation. IL-8 concentration in the culture supernatant was quantified and used to evaluate the activation of CD137 reporter cells. Representative data are shown in FIG. 9. At least 3 independent experiments were performed and results were comparable. The average $EC_{50}$ value calculated from the CD137 reporter dose response curves of clone 3712-IgG1v was 44.4 ng/mL (~0.31 nM; n=6).

Human CD8$^+$ T Cell Co-Stimulation Assay

CHO-K1 or CHO-K1-huFcγRIIB-Ile232 cells were harvested by centrifugation at 250 g for 5 minutes. The cells were resuspended in pre-warmed F12K medium containing 10% FBS at 2.5*10^6 cells/mL and transferred to 96-well cell culture plate at 100 μL/well. Meanwhile, 100 μL/well F12K medium containing 10% FBS was added to a third cell culture plate. DPBS was added to the edge of the cell culture plate. The plate was incubated at 37° C. in 5% $CO_2$ overnight. The next day, a freshly thawed vial of human CD8$^+$ T cells was transferred into a 50 mL tube containing 25 mL pre-warmed culture medium (RPMI1640 containing 10% FBS), and spun at 250 g for 10 min. The cell pellet was resuspended in 2 mL culture medium at 0.5-1*10^6 cells/mL, and a 50 μL/well cell suspension was added into the plate. Clone 3712-IgG1v or Avastin antibody was diluted to 100 μg/mL in RPMI medium containing 10% FBS and 0.4 μg/mL OKT3, and then a 4-fold serial dilution in assay buffer was prepared, yielding final concentrations of 100000, 25000, 6250, 1562.5, 390.6, 97.7, 24.4, 6.1, 1.53 and 0.38 ng/mL, 4× final concentration. The diluted clone 3712-IgG1v or Avastin was added to the cell culture plate at 50 μL/well. The plate was mixed and incubated at 37° C. in 5% $CO_2$ for about 72 hours. After the incubation, the cell culture supernatant was subjected to IFN-γ detection using a human IFN-γ assay kit from Cisbio.

Figure 10:
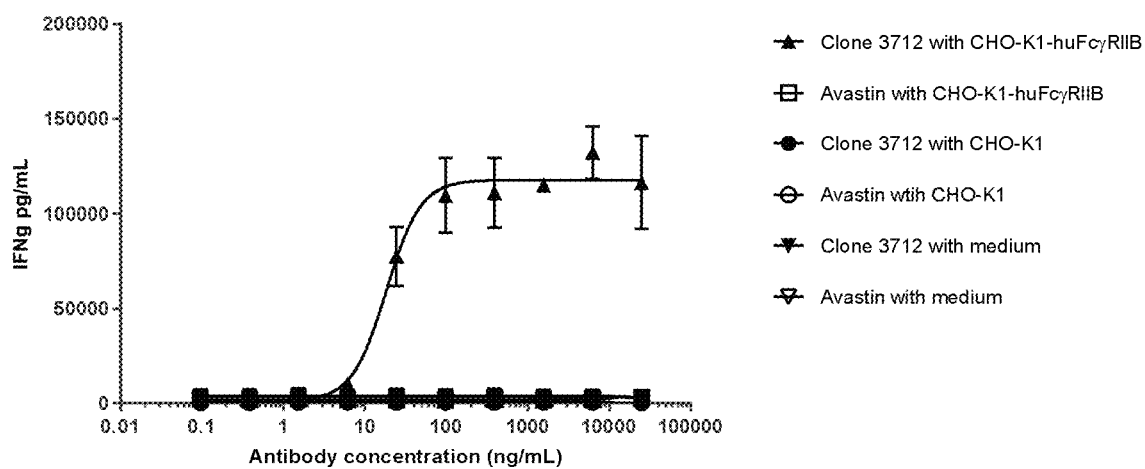
FIG. 10 is a graph showing the results of a human CD8+ T cell co-stimulation assay. Clone 3712 or Avastin in serial dilution at final concentrations of 25000, 6250, 1562.5, 390.6, 97.7, 24.4, 6.10, 1.53, 0.381, and 0.095 ng/mL, as shown on the x-axis, were added to a plate in which human CD8+ T cells were co-cultured with CHO-K1-huFcγRIIB, CHO-K1, or medium. IFNγ concentration, shown in the y-axis, indicates activation of the human CD8+ T cells.

Clone 3712-IgG1v showed dose-dependent agonistic activity to activate human CD8$^+$ T cells when co-cultured with CHO-K1-huFcγRIIB cells. There was no activity observed for clone 3712 when the human CD8$^+$ T cells were co-cultured either with CHO-K1 cells or medium. Avastin was used as a control to show the specificity of the CD137 activation. Representative data of at least three independent experiments are shown in FIG. 10. CD8$^+$ T cells from 6 donors were tested and the results were comparable. The average $EC_{50}$ value calculated from the CD8$^+$ T cell co-stimulation assay dose response curves of clone 3712 was 30.6 ng/mL (~0.21 nM; n=12).

Example 4: Pharmacokinetic Study of Humanized Antibodies

C57BL/6 mice (6-7 weeks old, 19-20 g, male, purchased from SLAC Laboratory Animal Co. LTD) were used for the study. Antibodies were formulated in PBS and administered via tail vein injection at 3 mg/kg in groups of 4 mice. No abnormal clinical symptoms were observed during the entire in-life study.

Figure 11:
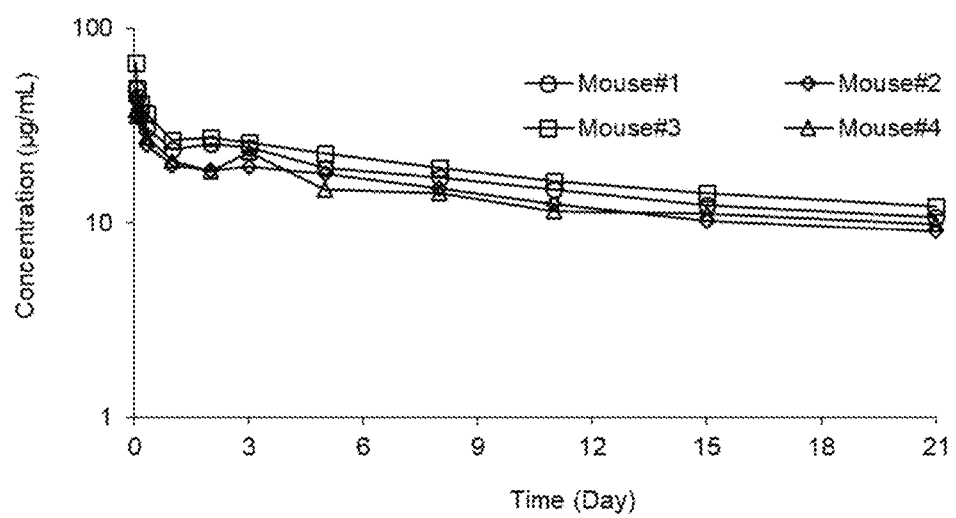
FIG. 11 is a graph showing the pharmacokinetics of clone 3712 in mice. Individual plasma concentration-time profiles of clone 3712 after an IV dose of 3 mg/kg in male C57BL/6 mice are depicted.

Blood sampling was performed pre-dose, 1 h, 2 h, 4 h, 8 h, 1 d, 2 d, 3 d, 5 d, 8 d, 11 d, 15 d and 21 d by serial bleeding. 10 μL of blood per time point was added to 40 uL of a PBS-BSA solution. The sample was then mixed well and centrifuged at 2000 g for 5 minutes at 4° C. The supernatant was put on dry ice immediately after collection and stored at approximately −70° C. until analysis. Blood antibody concentrations were determined by ELISA. FIG. 11 shows the blood antibody concentration of clone 3712-IgG1v after a single intravenous injection of 3 mg/kg. The results and pharmacokinetics parameters are summarized in Table 8 below.

TABLE 8

Individual and mean plasma concentration-time data of clone 3712 after an IV dose at 3 mg/kg in male C57BL/6 mice.

| Sampling time (Day) | Clone 3712-IgG1v Concentration (μg/mL) | | | | Mean (μg/mL) | SD | CV(%) |
|---|---|---|---|---|---|---|---|
| | Mouse#1 | Mouse#2 | Mouse#3 | Mouse#4 | | | |
| 0 | BQL | BQL | BQL | BQL | BQL | NA | NA |
| 0.0417 | 49.5 | 43.3 | 66.2 | 38.0 | 49.3 | 12.2 | 24.8 |
| 0.0833 | 44.9 | 35.9 | 49.5 | 35.4 | 41.4 | 6.94 | 16.8 |
| 0.1667 | 37.7 | 34.1 | 40.7 | 37.0 | 37.4 | 2.74 | 7.32 |
| 0.333 | 31.0 | 25.3 | 36.3 | 27.3 | 30.0 | 4.82 | 16.1 |
| 1 | 23.9 | 19.7 | 26.9 | 21.0 | 22.9 | 3.18 | 13.9 |
| 2 | 25.6 | 18.6 | 27.5 | 18.3 | 22.5 | 4.74 | 21.1 |
| 3 | 24.4 | 19.6 | 26.1 | 23.1 | 23.3 | 2.76 | 11.9 |
| 5 | 19.3 | 17.9 | 22.9 | 14.9 | 18.8 | 3.31 | 17.6 |
| 8 | 17.1 | 15.2 | 19.4 | 14.4 | 16.5 | 2.23 | 13.5 |
| 11 | 15.0 | 12.5 | 16.4 | 11.6 | 13.8 | 2.21 | 15.9 |
| 15 | 12.3 | 10.2 | 14.3 | 11.2 | 12.0 | 1.76 | 14.6 |
| 21 | 10.7 | 9.06 | 12.2 | 9.78 | 10.4 | 1.37 | 13.1 |
| PK parameters | Mouse#1 | Mouse#2 | Mouse#3 | Mouse#4 | Mean | SD | CV(%) |
| CL (mL/day/kg) | 5.51 | 6.08 | 5.03 | 6.11 | 5.68 | 0.518 | 9.11 |
| Vss (mL/kg) | 111 | 139 | 96.3 | 137 | 121 | 20.9 | 17.3 |
| V1 (mL/kg) | 54.0 | 63.7 | 36.7 | 73.8 | 57.1 | 15.8 | 27.7 |
| Alpha $t_{1/2}$ (day) | 0.127 | 0.140 | 0.0698 | 0.259 | 0.149 | 0.0796 | 53.4 |
| Beta $t_{1/2}$ (day) | 14.1 | 16.1 | 13.4 | 15.8 | 14.9 | 1.29 | 8.71 |
| AUC (day * μg/mL) | 545 | 493 | 597 | 491 | 532 | 50.2 | 9.44 |
| MRT (day) | 20.2 | 22.9 | 19.2 | 22.5 | 21.2 | 1.81 | 8.52 |

Example 5: In Vivo Evaluation of Efficacy of Humanized Antibodies

Materials and Methods

Mice

Human CD137 knock-in mice (C57BL/6, B-h4-1BB) and CD137/PD-1 double knock-in mice (C57BL/6, B-hPD-1/h4-1BB) were purchased from Biocytogen, Inc (Beijing, China). C57BL/6J mice were purchased from Beijing Vital River Laboratory Animal Technology Co., Ltd. (Beijing, China). All mice were maintained under specific pathogen-free conditions. Animal care and use were in accordance with institutional and NIH protocols and guidelines, and all studies were approved by the Animal Care and Use Committee of relevant institutions.

Cell Lines

Murine colon cancer MC38 cells were purchased from ShunRan Biotech (Shanghai, China) and cultured in 5% $CO_2$ and maintained in vitro in DMEM supplemented with 10% heat-inactivated fetal bovine serum. B16-OVA was cultured in 5% $CO_2$ and maintained in vitro in DMEM supplemented with 10% heat-inactivated fetal bovine serum (Gibco), 2 mmol/L L-glutamine, 100 units/mL penicillin, and 100 μg/mL streptomycin.

Efficacy Studies

Figure 12A:
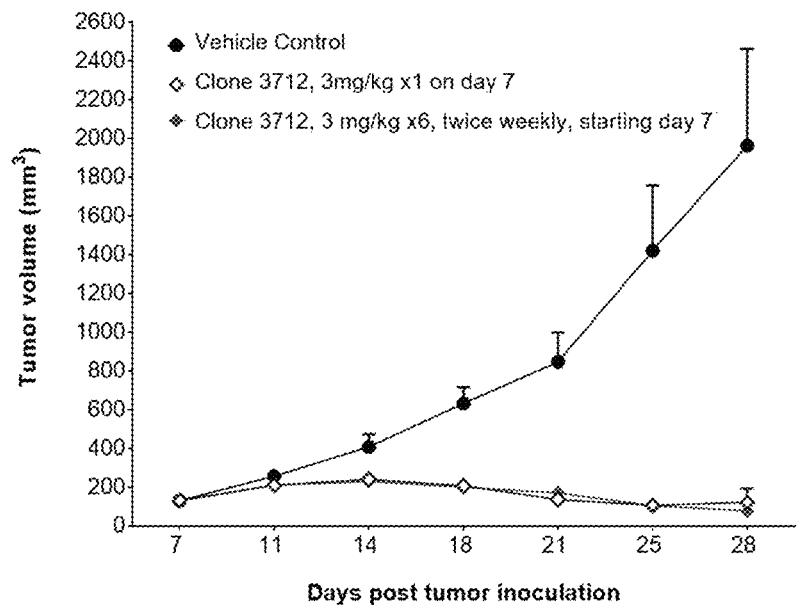
Figure 12B:
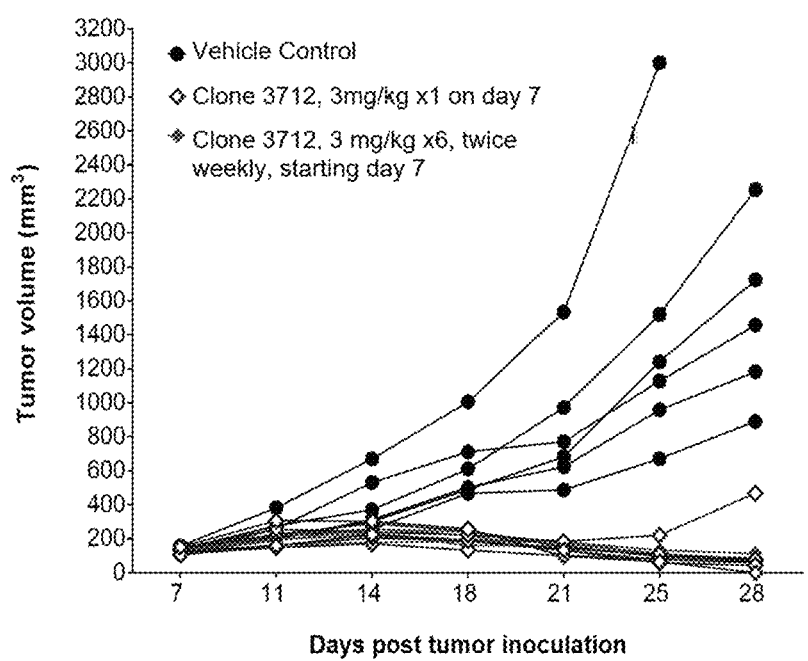

Murine colon cancer MC38 cells (0.5×10^6 cells in 0.1 mL PBS) were subcutaneously implanted into homozygous B-h4-1BB mice. Mice were divided into control and treatment groups (n=5-6), when the tumor size was approximately 150±50 mm³. Treatment was administered by intraperitoneal injections. Tumor sizes were measured by caliper twice a week and calculated as tumor volume using the formula: 0.5×length×width². The average ±SEM of tumor sizes are shown in FIGS. 12A and 12B.

Tumor growth inhibition (TGI) was determined during the dosing period by the formula: TGI=(Ct−Tt)/(Ct−C0)×100 where Ct=mean tumor volume of control at time t, Tt=mean tumor volume of treated at time t, and C0=mean tumor volume of control at time 0, which is the same for all randomized groups.

The antitumor efficacy of anti-CD137 antibodies in syngeneic mouse tumor models has been well documented (Melero et al. 1997, Murillo et al. 2008). Clone 3712 does not cross-react with murine CD137, so mice with the human CD137 extracellular domain knocked-in to replace the murine sequence were used to examine the antitumor activity of clone 3712.

Dosing Regimens

The first study compared the dosing regimens of clone 3712-IgG1v in the murine MC38 syngeneic tumor model, as shown in FIGS. 12A and 12B. When administered intraperitoneally at 3 mg/kg either once only or multiple doses in a twice weekly schedule, clone 3712 showed a comparable antitumor effect against the established tumors, with tumor growth inhibition of 100% and 103% at the end of experiment on day 21 post-dosing for the single dose and multiple doses groups, respectively (Table 9). A P value of T.TEST in Excel was performed to compare treatment and vehicle control groups.

Individual mouse data are shown in FIG. 12B. A single injection of clone 3712-IgG1v at 3 mg/kg was able to control the growth of pre-established MC38 carcinoma for 3 weeks, which demonstrates the robust antitumor activity of clone 3712-IgG1v in a preclinical tumor model.

TABLE 9

Tumor growth data in various groups as shown in FIG. 12

| Treatment | Tumor | Days post tumor inoculation (treatment started on Day 7) | | | | | | |
|---|---|---|---|---|---|---|---|---|
| | | 7 | 11 | 14 | 18 | 21 | 25 | 28 |
| Vehicle | Mean volume (mm³) | 130.6 | 256.7 | 408.0 | 632.1 | 846.2 | 1421.0 | 1963.8 |
| | TGI | | 0% | 0% | 0% | 0% | 0% | 0% |
| Clone 3712 3 mg/kg × 1 | Mean volume (mm³) | 130.6 | 210.3 | 239.8 | 206.6 | 136.0 | 106.1 | 122.5 |
| | TGI | | 37% | 61% | 85% | 99% | 102% | 100% |
| | P value (vs. Vehicle) | 0.999 | 0.257 | 0.034 | 0.001 | 0.001 | 0.003 | 0.004 |
| Clone 3712 3 mg/kg × 6 | Mean volume (mm³) | 130.6 | 209.8 | 229.7 | 199.7 | 169.8 | 104.5 | 77.7 |
| | TGI | | 37% | 64% | 86% | 95% | 102% | 103% |
| | P value (vs. Vehicle) | 0.9978 | 0.1659 | 0.0233 | 0.0005 | 0.0013 | 0.0029 | 0.0036 |

Efficacy of Clone 3712 Compared with Urelumab and Utomilumab Analogs

Figure 13A:
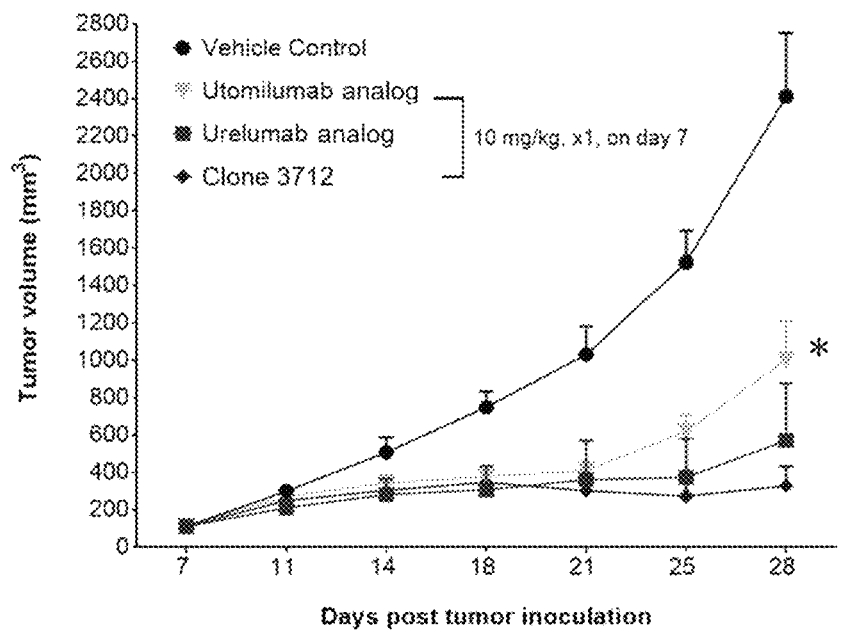
FIGS. 13A-13B are graphs showing tumor growth curves in various groups. Murine colon cancer MC38 cells were subcutaneously implanted into homozygous B-h4-1BB mice on day 0. Mice with established tumors were divided into control and treatment groups (n=6) on day 7, and treatments as shown were administered by intraperitoneal injections.

The next experiment compared the efficacy of clone 3712-IgG1 v and reference antibody urelumab and utomilumab analogs prepared in-house according to published sequences. When dosed at 10 mg/kg once on day 7, clone 3712 and urelumab showed comparable inhibition of tumor growth, whereas utomilumab was inferior as compared to clone 3712 (FIG. 13A). As shown in Table 6 below, utomilumab analog, urelumab analog and clone 3712 administered at 10 mg/kg resulted in tumor growth inhibition of 61%, 80%, and 91%, respectively, at the end of the experiment (day 21 post-injection of the single dose).

Figure 13B:
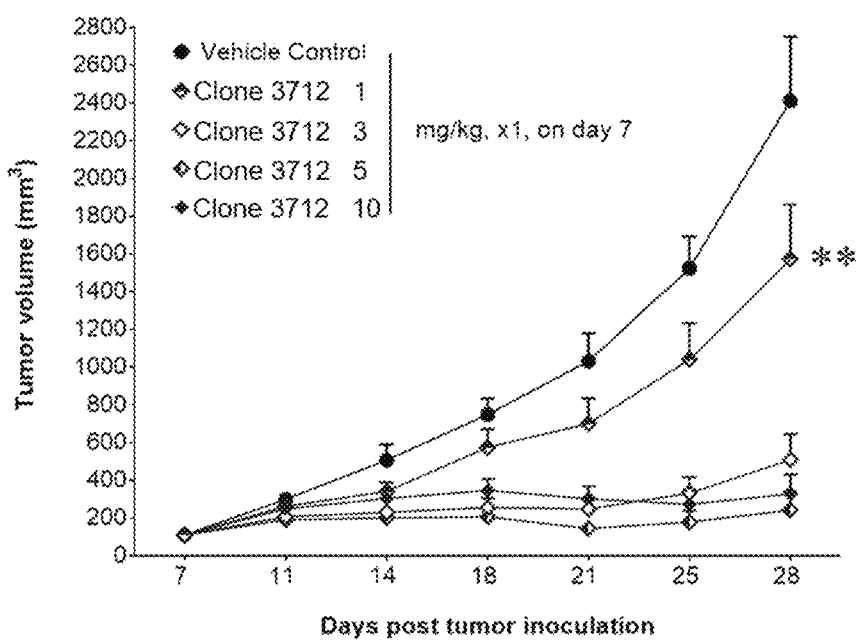

A dose titration of clone 3712-IgG1v was also performed in the study. As shown in FIG. 13B, clone 3712-IgG1v at 3, 5, and 10 mg/kg administered only once showed comparable suppression of the tumor growth, but the 1 mg/kg dose was insufficient, as TGI was below 50% at all time points. The detailed tumor volume and analysis data of TGI are listed in Table 10. P value of T.TEST in Excel was performed to compare treatment and vehicle control groups.

TABLE 10

Tumor growth data in various groups as shown in FIG. 13

| Treatment | Tumor | Days post tumor inoculation (treatment started on Day 7) | | | | | | |
|---|---|---|---|---|---|---|---|---|
| | | 7 | 11 | 14 | 18 | 21 | 25 | 28 |
| Vehicle control | Mean volume (mm$^3$) | 111.2 | 299.8 | 507.6 | 749.5 | 1031.4 | 1523.3 | 2412.7 |
| | TGI | | 0% | 0% | 0% | 0% | 0% | 0% |
| Utomilumab analog 10 mg/kg × 1 | Mean volume (mm$^3$) | 111.2 | 272.6 | 343.8 | 378.8 | 411.3 | 619.2 | 1003.8 |
| | TGI | — | 14% | 41% | 58% | 67% | 64% | 61% |
| | P value (vs. Vehicle) | 0.996 | 0.586 | 0.102 | 0.003 | 0.003 | 0.001 | 0.006 |
| Urelumab analog 10 mg/kg × 1 | Mean volume (mm$^3$) | 111 | 211 | 282 | 307 | 361 | 374 | 571 |
| | TGI | — | 47% | 57% | 69% | 73% | 81% | 80% |
| | P value (vs. Vehicle) | 0.974 | 0.145 | 0.083 | 0.016 | 0.026 | 0.002 | 0.002 |
| Clone 3712 10 mg/kg × 1 | Mean volume (mm$^3$) | 111 | 249 | 305 | 347 | 302 | 273 | 329 |
| | TGI | — | 27% | 51% | 63% | 79% | 89% | 91% |
| | P value (vs. Vehicle) | 0.979 | 0.249 | 0.050 | 0.003 | 0.001 | <0.001 | <0.001 |
| Clone 3712 5 mg/kg × 1 | Mean volume (mm$^3$) | 111 | 191 | 201 | 207 | 145 | 179 | 242 |
| | TGI | — | 57% | 77% | 85% | 96% | 95% | 94% |
| | P value (vs. Vehicle) | 0.980 | 0.036 | 0.005 | <0.001 | <0.001 | <0.001 | <0.001 |
| Clone 3712 3 mg/kg × 1 | Mean volume (mm$^3$) | 111 | 207 | 230 | 257 | 248 | 331 | 509 |
| | TGI | — | 49% | 70% | 77% | 85% | 84% | 83% |
| | P value (vs. Vehicle) | 0.998 | 0.063 | 0.010 | 0.001 | 0.001 | <0.001 | <0.001 |
| Clone 3712 1 mg/kg × 6 | Mean volume (mm$^3$) | 111 | 262 | 341 | 575 | 700 | 1040 | 1574 |
| | TGI | — | 20% | 42% | 27% | 36% | 34% | 36% |
| | P value (vs. Vehicle) | 0.989 | 0.413 | 0.110 | 0.204 | 0.130 | 0.091 | 0.089 |

Antitumor Effects of Combination of Clone 3712 and an Anti-PD-1 Antibody

Figure 14:
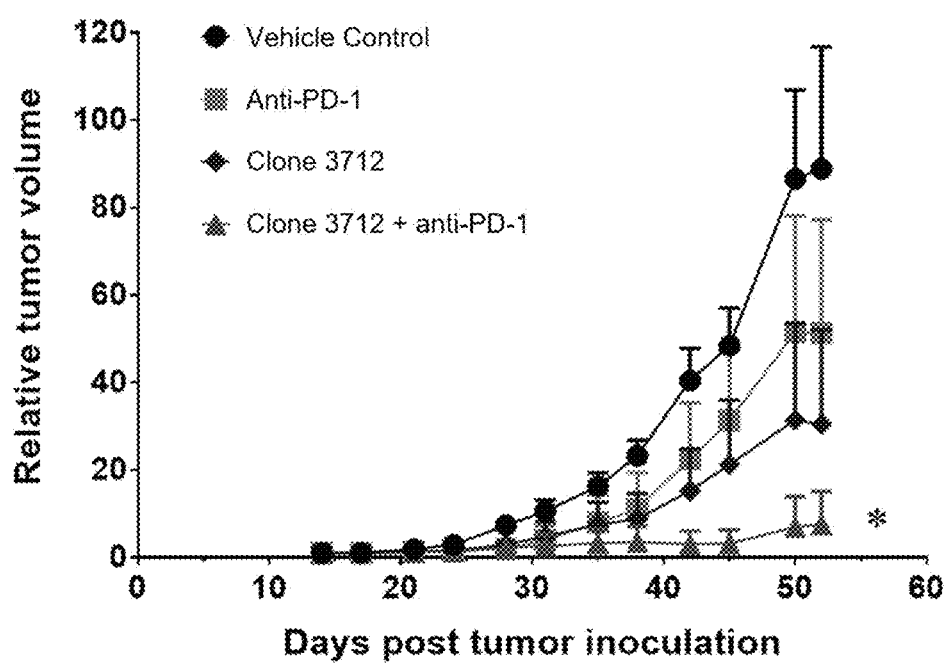
FIG. 14 is a graph showing the combination efficacy of clone 3712 with an anti-PD-1 antibody in a murine tumor model. Murine melanoma B16-OVA cells were subcutaneously implanted on day 0 into WT B6 mice engrafted with hPD-1/4-1BB mouse donor bone marrow cells after lethal irradiation. Tumor volumes were measured along 3 orthogonal axes (a, b, and c) and calculated as tumor volume=abc/2. After tumors was established (day 14), mice were divided into control and treatment groups (n=5) treated with 100 μg of anti-PD-1 antibody on days 14, 21 and 28, or 100 μg of anti-CD137 clone 3712 administered by intraperitoneal injections on day 14, or a combinational treatment with the same dosing schedule of the single agents. Tumor growth was measured twice a week. The relative tumor size was calculated by dividing the tumor size with the initial tumor size on day 14. The average ±SEM of tumor sizes are shown. Mean values were compared using multiple t tests in Prism. Statistically significant differences p<0.05 is noted with * when compared to the single agent groups.

A possible synergistic antitumor activity between a CD137 agonist antibody and a PD-1 blocking antibody has been reported (Tolcher et al. 2017, Azpilikueta et al. 2016). The B16 melanoma syngeneic tumor model was used to test the clone 3712-IgG1v and anti-PD-1 combination. Seven to eight weeks old WT B6 mice were lethally irradiated with a single dose of 950 rads. The next day, irradiated mice were adoptively transferred with 2-3×10$^6$ hPD-1/4-1BB mouse donor bone marrow cells. Mice were maintained on sulfamethoxazole and trimethoprim (Bactrim) antibiotics diluted in drinking water for 4 weeks after reconstitution before the tumor efficacy experiment was started. Approximately 1×10^6 B16-OVA cells were injected subcutaneously on the right flank into bone marrow chimera mice. Tumor volumes were measured along 3 orthogonal axes (a, b, and c) and calculated as tumor volume=abc/2. After tumor was established (~9-12 days, ~100 mm$^3$), mice were treated with 100 μg (~5 mg/kg) of anti-PD-1 antibody on days 14, 21 and 28, or 100 μg (~5 mg/kg) of anti-4-1BB antibody administered by intraperitoneal injection on day 14, or the combinational treatment, as indicated. Tumor growth was measured twice a week. The relative tumor size was calculated by dividing the tumor size by the initial tumor size on day 14. As shown in FIG. 14, combination of clone 3712-IgG1v and anti-PD-1 resulted in a more significant inhibition of the tumor growth as compared to either of the single agent treatment groups. TGI numbers on Day 52 of study termination for the single agent anti-PD-1, clone 3712-IgG1v and combination groups were 42%, 66% and 91%, respectively.

Example 6: Epitope Mapping of CD137 Antibodies

The extracellular part of CD137 receptor protein consists of four domains. Genes of CD137 receptor human/mouse chimeras were synthesized using standard laboratory techniques. The different chimeras were designed by exchanging domains or modules of the human CD137 receptor with corresponding mouse CD137 receptor. The chimeras were designed based on evaluation of the human and mouse sequences and 3D investigation of human CD137 receptor. The synthesized genes were assigned project specific ID numbers (see Table 11).

TABLE 11

Identity of chimeric constructs

| ID construct | Description of coding region of the chimeric DNA constructs |
|---|---|
| Ly048 | Human CD137 with mouse domain CRD2 |
| Ly049 | Human CD137 with mouse domain CRD3 |
| Ly050 | Human CD137 with mouse domain CRD4 |
| Ly051 | Mouse CD137 with human domain CRD2 |
| Ly052 | Mouse CD137 with human domain CRD3 |
| Ly110 | Mouse CD137 with human domain CRD2 and CRD3 |

The binding of clone 3712-IgG1v with chimeric CD137 receptor protein was analyzed in standard ELISA format. For the data shown in FIGS. 16A-B, Clone 3712-IgG1v was diluted in DPBS to 1 μg/mL, and then coated onto an ELISA plate (Corning, Catalog number: 9018, high binding) with a volume of 50 μL (0.05 μg) per well, and incubated at 4° C.

overnight. The plate was decanted and washed once; assay diluent was added 200 µL/well. After one-hour incubation at room temperature, the plate was washed with PBST one time. CD137 receptor human/mouse chimeras were diluted in assay diluent to 100 or 10 µg/mL, and then a 4-fold serial dilution in assay diluent for 11 points to final concentrations of 100000, 25000, 6250, 1562.5, 390.63, 97.66, 24.41, 6.10, 1.53, 0.38 and 0.095 ng/mL or 10000, 2500, 625, 156.25, 39.06, 9.77, 2.44, 0.61, 0.15, 0.038 and 0.0095 ng/mL. The diluted CD137 receptor was added to the assay plate, 50 µL/well, in duplicate. The plate was incubated one hour at room temperature and then washed three times with PBST. Goat anti-human IgG-H+L HRP conjugated at 1:100,000 20 dilution was added to the plate at 100 µL/well. The plate was then incubated one hour at room temperature followed by washing with PBST four times. The TMB substrate solution was added at 100 µL/well. The color was allowed to develop for 15 minutes, and was stopped with 100 µL/well 2N H2SO4. Absorbance at 450 nm and 620 nm was determined by a Tecan F200 Pro reader.

For the data shown in FIGS. 16C-D, chimeric CD137 receptor protein samples were diluted in DPBS to 5 µg/mL and then coated onto an ELISA plate (Corning, Catalog number: 9018, high binding) at 50 µL (0.25 µg) per well, and incubated at 4° C. overnight. The plate was decanted and washed once; assay diluent was added at 200 µL/well. After a 1-hour incubation at room temperature, the plate was washed with PBST one time. Clone 3712 was diluted in assay diluent to 100 or 10 µg/mL, and then a 4-fold serial dilution in assay diluent for 11 points to final concentrations of 100000, 25000, 6250, 1562.5, 390.63, 97.66, 24.41, 6.10, 1.53, 0.38 and 0.095 ng/mL or 10000, 2500, 625, 156.25, 39.06, 9.77, 2.44, 0.61, 0.15, 0.038 and 0.0095 ng/mL. The diluted clone 3712 was added to the assay plate, 50 µL/well, in duplicate. The plate was incubated 1 hour at room temperature and then washed three times with PBST. Goat anti-human IgG-H+L HRP-conjugated at 1:100,000 dilution or goat anti-mouse IgG (H+L) secondary antibody, HRP, 10 at 1:50,000 dilution was added to the plate at 100 µL/well. The plate was incubated 1 hour at room temperature followed by washing with PBST four times. The TMB substrate solution was added 100 µL/well. The color was permitted to develop for 15 minutes and then 100 µL/well 2N H2SO4 was added to terminate the reaction. Absorbance at 450 nm and 620 nm was determined by a Tecan F200 Pro reader.

None of the human CD137 antibodies tested bound to murine CD137. Accordingly, if a given antibody does not bind to a particular chimera, this indicates that the antibody is specific for one of the domains which has been replaced with a murine domain in that chimera.

The binding pattern for clone 3712 shows that the amino acid residues critical for binding are likely located in domain 2 and 3 (CRD2-3), in contrast to Utomilumab and Urelumab, which bind to CRD3-4 and CRD1-2 respectively (Chin et al., 2018; Li et al., 2018).

Example 7: Evaluation of Additional Anti-CD137 Humanized Antibodies (i) Binding Affinity KD Measurements of CD137 Antigen Binding were made according to the protocol described in Example 2 above. The chimeric and humanized antibodies were tested in an antigen-binding assay on Octet Red 96 to estimate binding kinetics. Antibodies were loaded onto anti-human Fc (AHC) biosensors. Loaded sensors were dipped into a serial dilution of CD137 protein (300 nM, 1:3 down, 7 points) in assay buffer (PBS with 0.1% BSA, 0.02% Tween-20 (pH 7.2)). Kinetic constants calculated using a monovalent (1:1) model are shown in Table 12 below. Except for clone 3714, all humanized antibodies showed similar or slightly lower but acceptable affinity compared with the parental chimeric reference antibody 371.

TABLE 12

Kinetic Constants of Humanized Anti-CD137 Antibodies

| Loading Sample ID | KD (M) | on(1/Ms) | kdis(1/s) |
|---|---|---|---|
| 371 (chimera) | 3.9E−09 | 2.8E+05 | 1.1E−03 |
| 3711 | 2.50E−09 | 1.90E+05 | 4.60E−04 |
| 3712 | 1.00E−08 | 3.10E+05 | 3.10E−03 |
| 3713 | 3.80E−09 | 2.90E+05 | 1.10E−03 |
| 3714 | <1.0E−12 | 1.30E+05 | <1.0E−07 |
| 3715 | 5.90E−09 | 3.10E+05 | 1.80E−03 |
| 3716 | 7.00E−09 | 3.20E+05 | 2.20E−03 |
| 3717 | 2.30E−09 | 1.50E+05 | 3.40E−04 |
| 3718 | 8.30E−09 | 3.10E+05 | 2.60E−03 |
| 3719 | 8.50E−09 | 3.10E+05 | 2.60E−03 |

Figure 15:
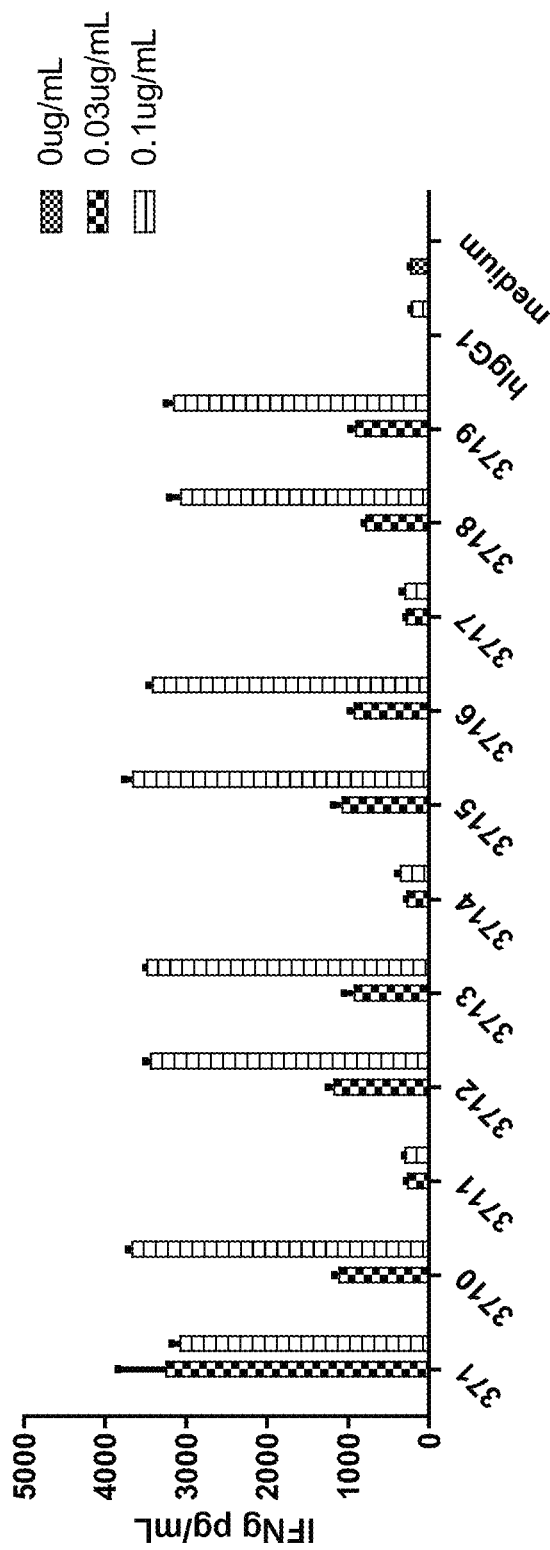
FIG. 15 is a diagram showing T cell stimulation activity for the humanized antibodies as indicated at different concentrations.

Evaluation of the antibodies by T Cell Functional Assays was performed according to the protocol described in Example 2. Clones 3711, 3714, and 3717 demonstrated low T cell stimulation activity (FIG. 15).

(ii) Competitive Binding of Clone 3712 and CD137 Ligand to CD137 Receptor

Competition between CD137L and clone 3712 for binding to CD137 receptor was determined in standard ELISA format. Competitive binding profile of clone3712 to CD137 receptor was compared with those of reference anti-CD137 antibodies 371, 370, 372, 375, 390 and 402 (See WO2019/113039, the relevant disclosures of which are incorporated by reference for the subject matter and purpose referenced herein). CD137 receptor was diluted in DPBS to 1 µg/mL, and then coated onto an ELISA plate (Corning, Catalog number: 9018, high binding) with a volume of 50 µL (0.05 µg) per well, and incubated at 4° C. overnight. The plate was decanted and washed once; assay diluent was added 200 µL/well. After one-hour incubation at room temperature, the plate was washed with PBST one time. clone 3712, 371, 370, 372, 375, 390, 402 and SSI-361 (negative control antibody) were diluted in assay diluent to 9 µg/mL, and then diluted serial in assay diluent for 11 points to final concentrations of 9000, 3000, 900, 300, 90, 30, 9, 3, 0.9, 0.3 and 0.09 ng/mL. The diluted CD137 receptor was added to the assay plate, 50 µL/well, in duplicate. The plate was incubated one hour at room temperature. CD137L was diluted in assay diluent to 6 µg/mL, and then diluted in serial in assay diluent for 11 points to final concentrations of to get the serial concentration 6000, 2000, 600, 200, 60, 20, 6, 2, 0.6, 0.2, 0.06 ng/ml, or diluted to final concentration of 40 ng/ml. The diluted CD137L was added to the assay plate, 50 µL/well, in duplicate. The plate was incubated one hour at room temperature and then washed three times with PBST. Goat anti-human IgG-H+L HRP conjugated at 1:100,000 20 dilution was added to the plate at 100 µL/well. The plate was then incubated one hour at room temperature followed by washing with PBST four times. The TMB substrate solution was added at 100 µL/well. The color was allowed to develop for 15 minutes, and was stopped with 100 µL/well 2N H2SO4. Absorbance at 450 nm and 620 nm was determined by a Tecan F200 Pro reader.

Figure 17:
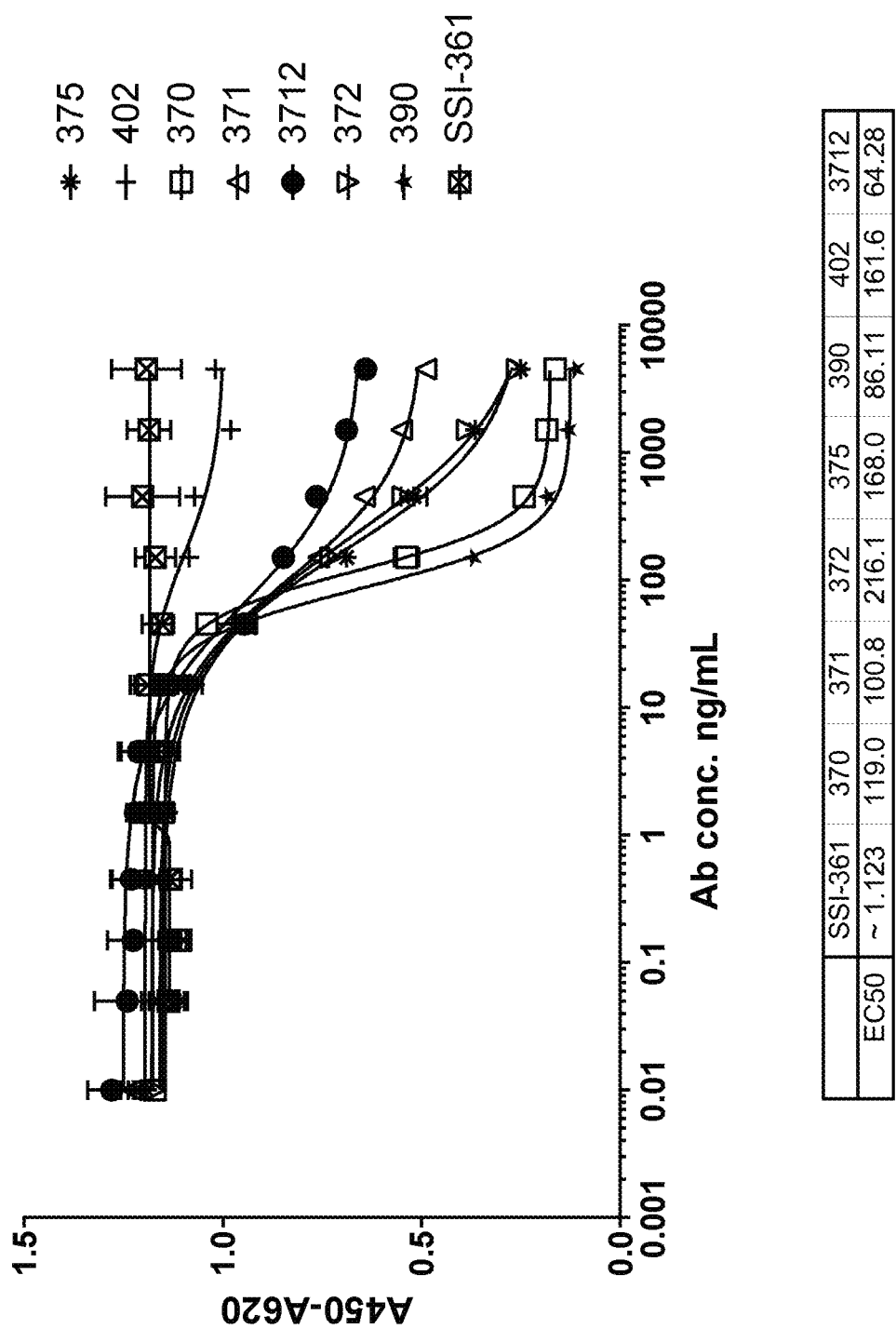
FIG. 17 is a diagram showing the binding of various anti-CD137 antibodies to the CD137 receptor.

The results shown in FIG. 17 suggest that the binding of clone 3712 to the CD137 receptor partially blocked the binding of CD137 receptor to CD137L.

Example 8: Efficacy Evaluation of Clone 3712 in the A375 NPG Mouse In Vivo Melanoma Model The humanized $V_H$ and $V_L$ sequences of clone 3712 described above were used to construct an anti-CD137 antibody (clone 3712-IgG1v disclosed in Example 3 above) comprising an Fc region of human IgG1/kappa (SEQ ID NOs: 6 and 7), which contains an Fc variant of human IgG1. 3712-IgG1v was cloned into expression vectors for production in transient expression CHO cells and in stable CHO cell lines, according to methods described in Example 3 above.

Cell Culture

The A375 cell line was obtained from iCell Bioscience Inc, and maintained in vitro as a monolayer culture in DMEM medium supplemented with 10% heat inactivated fetal bovine serum, at 37° C. in an atmosphere of 5% CO2 in air. The tumor cells were routinely subcultured every 3-5 days by trypsin-EDTA treatment. Cells growing in an exponential growth phase were harvested and counted for tumor grafting.

Animals

NPG (NOD-Prkdc$^{scid}$Il2rg$^{null}$) mice provided by Joinnlab company are used for the study, which are all males, 4 weeks old, weighing approximately 19-31 g. A total number of 20 mice were randomized by weight into 3 groups.

Human Immune Cells and Tumor Grafting

G-CSF-mobilized peripheral blood CD34(+) hemopoietic stem cells were isolated from peripheral blood stem cells (PBSC) by magnetic activated cell sorting (MACS), and then were transplanted into NPG mice irradiated with sublethal dose of X ray by marrow cavity transplantation. After 12 weeks after transplantation, each mouse is grafted subcutaneously at the right flank with $2\times10^6$ of A375 cells in 0.2 ml of PBS.

Immunomodulatory Agent Treatment

Mice of Groups 1 were treated with PBS and mice of Groups 2 were treated with clone 3712-IgG1v at 5 mg/kg twice weekly through intravenous injection starting at day 1, day 4, day 8, day 11, day 15, day 18, day 22, day 25 and day 29 for a total of 9 doses.

Endpoints

Tumors were measured twice weekly in two dimensions using a vernier caliper, starting from day 4, and the volumes were expressed in mm3 using the formula: $V=0.5\ a\times b^2$, where a and b are the long and short diameters of the tumor, respectively. The major endpoint of the study was tumor growth inhibition (TGI). TGI is expressed as: TGI (%)=$100\times(1-T/C)$. T and C are the mean tumor volume of the treated and control groups, respectively, on day 29.

Figure 18:
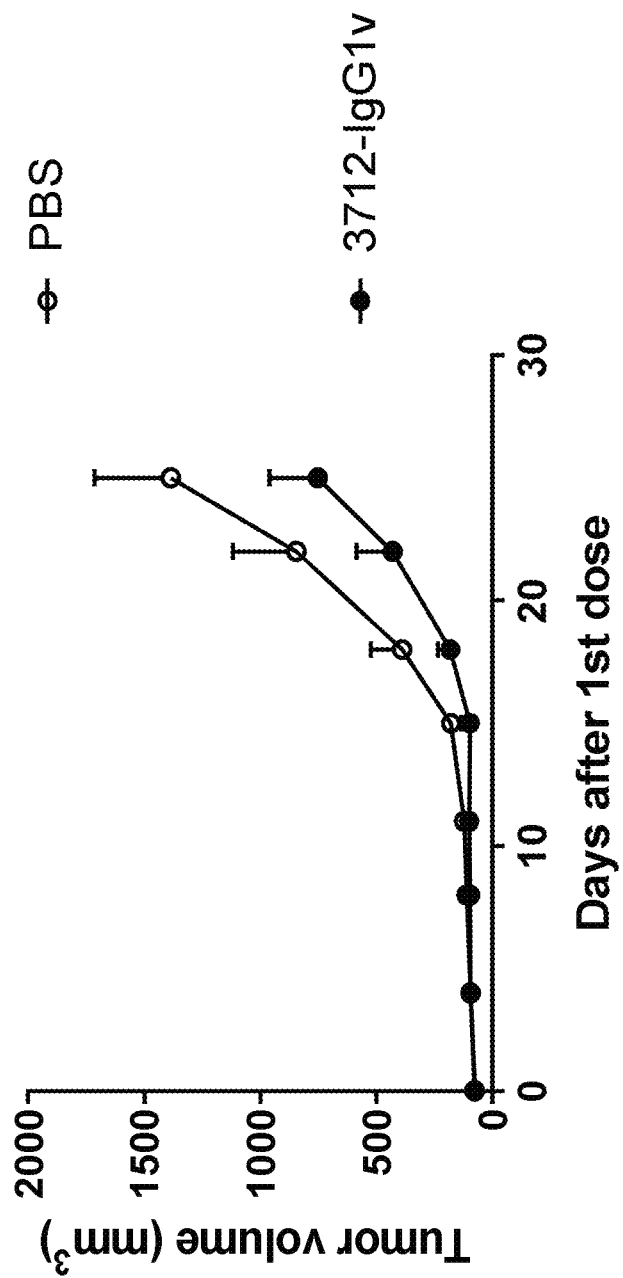
FIG. 18 is a diagram showing inhibition of tumor growth inhibition by clone 3712-IgG1v.

As shown in FIG. 18, the treatment of 3712-IgG1v (Group 2) demonstrated significant tumor growth inhibition (TGI=41%, p=0.09), compared with the PBS-treated control group (Group 1).

Example 9: Cytokine Release Activity Assessment

The in vitro cytokine release assays using human whole blood and PBMCs suggested a low risk of 3712-IgG1v, either in soluble or solid forms, to induce cytokine release storm, and compared with a CD28 agonistic antibody (TGN1412) and a CD3 agonistic antibody (OKT3).

(i) Cytokine Release of High-Density Pre-Cultured PBMC Induced by Soluble 3712-IgG1v PBMC from four healthy donors were tested in the high-density culture experiments to assess the potential risk of cytokine induction by soluble 3712-IgG1v. CD28 agonist antibody TGN1412 and CD3 antibody OKT3 were used as positive controls, while Avastin was used as negative control. The culture supernatants at 2 and 24 hours post antibody treatment were analyzed for the levels of IFN-γ, TNF-α, IL-6 and IL-2. At 2 hour time point, none of the tested antibodies induced changes of these cytokines. At 24 hours TGN1412 and/or OKT3 caused elevation of IFN-γ, TNF-α, IL-6 and IL-2 in all donors, but 3712-IgG1v, as well as Avastin, at a wide range of concentrations (from 3 ng/mL to 300 μg/mL) did not induce any noticeable change. The data suggest that the risk of 3712-IgG1v to induce cytokine storm may be low.

(ii) Cytokine Release of PBMC Induced by Plate-Bound 3712-IgG1v

Plate-bound 3712-IgG1v was tested in culture with PBMCs from four healthy donors to assess its ability to induce cytokine production. CD28 agonist antibody TGN1412 and CD3 antibody OKT3 were used as positive controls, while Avastin was used as negative control. The culture supernatants at 2 and 24 hours post incubation were analyzed for the levels of IFN-γ, TNF-α, IL-6 and IL-2. At 2 hour time point, none of the tested antibodies induced changes of these cytokine. At 24 hours, TGN1412 and/or OKT3 caused elevation of IFN-γ, TNF-α, IL-6 and IL-2 in all donors except for TNF-α and IL-6 in donor 1, but 3712-IgG1v, as well as Avastin, at a wide range of concentrations (from 0.1 μg/well to 100 μg/well) did not induce any noticeable change. The data suggest that the risk of 3712-IgG1v to induce cytokine storm may be low.

(iii) Cytokine Release of Whole Blood Induced by Soluble 3712-IgG1v

The immune modulating activity of 3712-IgG1v (LYV1) was also examined using whole blood samples from a cohort of 15 healthy donors. The whole blood within 4 hours of blood draw was incubated with 3712-IgG1v or controls. Levels of cytokines in the plasma were evaluated using the Luminex platform. Whole blood incubated with PWM was used as a positive control and whole blood incubated with PBS was used to determine background responses. Plasma samples were examined for IL-6, IL-8, IL-10, IFN-γ and TNF-α. As expected, incubation of whole blood with positive control PWM resulted in a significant increase in secretion of all cytokines compared to whole blood incubated with PBS.

To benchmark data generated for the sample against data reported from the clinic, two clinical antibodies, Lemtrada and Erbitux, with known cytokine release rates were ran in parallel. Erbitux is recognised to have low levels of infusion related reactions and was used to set the baseline for positive cytokine release. In contrast, Lemtrada is associated with a high rate of infusion reaction in the clinic (Bugelski, Achuthanandam, Capocasale, Treacy, & Bouman-Thio, 2009) and was used to establish a high responding clinical control.

The mean levels of IL-6, IL-8, IL-10, IFN-γ and TNF-α following treatment of whole blood with Lemtrada were significantly above cultures treated with 3712-IgG1v or Erbitux®. Statistical analysis showed no significant difference between the levels of IL-6, IL-10, IFN-γ and TNF-α produced in response to 3712-IgG1v when compared to Erbitux®, irrespective of the concentration.

In sum, the effect of 3712-IgG1v on cytokine release was examined in a comprehensive set of in vitro assays including high density pre-culture of human PBMC before cytokine release assay and whole human blood of healthy donors for 24 hours. 3712-IgG1v was tested after being coated onto culture plate and then cultured with human PBMC for 2 and 24 hours before cytokine detection. 3712-IgG1v, as well as clinical reference antibody Avastin® or Erbitux®, did not show noticeable activity in inducing cytokine release in these assays, suggesting the risk of 3712-IgG1v to induce cytokine storm in human would be low.

Example 10: Pharmacokinetics and Toxicology Studies in Cynomolgus Monkey

Based on target sequence homology, conserved binding affinity and FcγRIIB-dependent CD137 agonism, cynomolgus monkey was identified as the only pharmacologically relevant nonclinical species for assessing the PK and safety profile of 3712-IgG1v.

Pharmacokinetics Study

To understand the PK profile of 3712-IgG1v following i.v. infusion(s), the intended route of administration in human, two single-dose (3, 10 or 30 mg/kg, or 0, 10, 30 or 100 mg/kg) studies and one repeat-dose study (0, 10, 30 or 100 mg/kg) were conducted in naïve cynomolgus monkeys.

Single-Dose Pharmacokinetics

Following a single i.v. administration of 3712-IgG1v, systemic exposure was achieved in all animals with no significant gender difference. Dose normalized systemic exposure (AUC and $C_{max}$) data suggested a linear pattern of kinetics in the dose range of 3-100 mg/kg. The average $T_{1/2}$ ranged from 64.6 to 133 hours, CL from 0.355 to 0.488 mL/hr/kg and mean Vdss from 54.9 to 69.7 mL/kg in the dose range of 3-30 mg/kg, indicating 3712-IgG1v was presumably distributed in blood and was slowly eliminated from the circulation. Formation of anti-3712-IgG1v-antibody (ADA) was detected in most animals, with higher incidences in animals receiving lower doses, suggesting 3712-IgG1v is immunogenic in monkeys.

Repeat-Dose Pharmacokinetics

The repeat-dose PK was evaluated in conjunction with a repeat-dose toxicology study in cynomolgus monkeys. Following repeated i.v. doses of 3712-IgG1v (QW×5 at 0, 10, 30 or 100 mg/kg), significant decreases in systemic exposure were observed in animals in the 10 and 30 mg/kg groups, which are likely the result of increased clearance and the impact of ADA. Formation of ADA was mainly detected in lower dose groups, as 10/10, 8/10 and 2/10 of the animals in 10, 30 and 100 mg/kg groups were found positive on Day 29, respectively. The high prevalence of ADA in 10 and 30 mg/kg groups compromised our ability to assess PK accurately. In the 100 mg/kg dose group where most animals were ADA negative, mild accumulation was noted, with accumulation ratios (ARs) of 1.6 for male and 1.7 for female.

Toxicology Study

The evaluation of the potential risk to humans receiving 3712-IgG1v was conducted in two US-GLP compliant toxicology studies in naïve cynomolgus monkeys. The first was a single-dose study to evaluate the potential acute toxicity of an i.v. infusion of 3712-IgG1v (at 0, 10, 30, or 100 mg/kg) and to determine the maximum tolerated dose (MTD). The second, a pivotal, 29-day repeat-dose toxicity study was conducted by administering five i.v. infusions of 0, 10, 30 or 100 mg/kg, QW, for 29-days with a 6-week recovery period. The potential target organ and the sub-chronic toxicity were assessed, as well as the reversibility, persistence, or delayed occurrence of any toxicity. Safety pharmacology and injection site reaction were also evaluated as part of the repeat-dose general toxicology study.

Single-Dose Toxicity

A US-GLP compliance, single-dose toxicology study was conducted to evaluate the potential acute toxicities of 3712-IgG1v in naïve cynomolgus monkeys. A total of eight monkeys were assigned to 4 groups (1/sex/group) and received 0 (vehicle), 10, 30 or 100 mg/kg of 3712-IgG1v via a 60-min i.v. infusion. The animals were observed for 14 days post dosing for the evaluations of viability, clinical observations, body weight, food consumption, clinical pathology (hematology, serum chemistry, coagulation, and urinalyses), toxicokinetics (TK), and immunogenicity. In addition, non-GLP compliant analyses of immunotoxicity (cytokines), lymphocyte phenotyping and soluble target antigen were performed. On Day 15, all animals were necropsied and subjected to gross (macroscopic) and histopathological (microscopic) examinations.

There were no unscheduled deaths during the course of study. No treatment-related effects on clinical observations, body weight, food consumption, clinical pathology, immunotoxicity or lymphocyte phenotyping were observed. In addition, necropsy examinations revealed no test article-related macroscopic or microscopic findings.

The systemic exposure to 3712-IgG1v (both $C_{max}$ and $AUC_{0-168}$) appeared to increase proportionally with increasing dose and there was no marked sex difference observed in systemic exposure at any dose level. ADA was positive in ½, ½, ½ and ½ of animals receiving 0, 10, 30 and 100 mg/kg 3712-IgG1v, respectively. However, the titers were very low in all but one female animal in the 10 mg/kg group (the values were 36, 1120, 70, and 12 on Day 14 for the 0, 10, 30 and 100 mg/kg groups, respectively). Following the i.v. infusion of clone 3712-IgG1v, serum CD137 protein increased from the baseline level of 0.1 ng/mL to 1.3 ng/mL in dose-dependent manner, suggesting that 3712-IgG1v could bind and stabilize CD137 protein in the circulation of the cynomolgus monkeys.

In conclusion, a single i.v. infusion of 3712-IgG1v at 10, 30, 100 mg/kg was well tolerated. Therefore, the MTD of a single i.v. dose of 3712-IgG1v in cynomolgus monkeys was considered to be no less than 100 mg/kg.

Repeat-Dose Toxicity

The potential sub-chronic toxic effects of 3712-IgG1v were investigated in a US-GLP compliant, 29-day repeat-dose toxicology study in cynomolgus monkeys. The study design included a 42-day recovery phase to assess the reversibility, persistence, or any delayed occurrence of adverse effects. A total of 40 monkeys were assigned to 4 groups (5/sex/group) and received a 60-min i.v. infusion of 0 (vehicle), 10, 30, and 100 mg/kg 3712-IgG1v, once per week for 29 days (QW×5). At the initiation of dosing, monkeys were at ages of approximate 2.5 to 3.5 years and the body weights ranged from 2.0 to 2.7 kg. On Day 30, the main group animals (3/sex/group) were euthanized and necropsied while the recovery group animals (2/sex/group) were observed for additional 42 days until euthanization on Day 71.

The animals were evaluated for mortality, clinical observations (including injection site observation), body weight, food consumption, body temperature, safety pharmacology (ECG, heart rate, blood pressure, respiration parameters and neurological examinations), ophthalmic examinations, clinical pathology (hematology, coagulation, serum chemistry and urinalysis), TK, immunogenicity (ADA analysis), organ weight and gross pathological and histopathological examinations. In addition, non-GLP compliant analyses of immunotoxicity (cytokines), lymphocyte phenotyping and soluble target antigen were performed.

Systemic exposure was achieved in all animals. There was no sex difference in systemic exposure following the $1^{st}$ i.v. infusion and the systemic exposure (AUC0-168 h and Cmax) increased dose-proportionally. The formation of ADA was detected in 10/10, 8/10 and 2/10 animals in the 10, 30 and 100 mg/kg groups on Day 29, respectively. Decreased systemic exposure following the $4^{th}$ dose was observed in the 10 mg/kg group where the impact of ADA formation on drug exposure was significant. However, a mild accumulation was observed in the 100 mg/kg group, where most animals were ADA negative.

No unscheduled death occurred during the course of the study. There were no test article-related changes with regard to clinical observations, local irritation at the injection site, body weight, food consumption, body temperature, safety pharmacology, ophthalmic examinations, clinical pathology (hematology, coagulation, coagulation, and urinalysis), safety pharmacology (electrocardiography, blood pressure, heart rate, respiration and neurological examinations), immunology (B and T lymphocyte phenotyping, cytokine analysis), or pathology changes (organ weights, macroscopic and microscopic observations). All differences observed in clinical pathology and immunology parameters were not considered test article-related because they were small in magnitude, not dose related, and/or within the historical reference ranges for this laboratory.

In conclusion, repeated i.v. infusions of 3712-IgG1v to male and female cynomolgus monkeys at 10, 30, or 100 mg/kg for 29 days (QW×5) were well tolerated. No test article-related toxicity or toxic organ was identified. The no-observed-adverse-effect level (NOAEL) was considered to be 100 mg/kg in this study. At this dose level, the mean Cmax and $AUC_{0-168}$ following the $4^{th}$ dose were 4930 μg/mL and 355000 μg*h/mL for males, and 4010 μg/mL and 300000 μg*h/mL for females, respectively.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A humanized anti-CD137 antibody, which comprises a heavy chain that comprises a heavy chain variable ($V_H$) region and a light chain that comprises a light chain variable ($V_L$) region, wherein the $V_H$ comprises the amino acid sequence of SEQ ID NO:3, and wherein the $V_L$ comprises the amino acid sequence of SEQ ID NO: 5.

2. The humanized anti-CD137 antibody of claim 1, wherein the antibody is an IgG1 molecule.

3. The humanized anti-CD137 antibody of claim 2, wherein the heavy chain further comprises an Fc variant having a modified effector activity as compared to a wild-type Fc counterpart.

4. The humanized anti-CD137 antibody of claim 3, wherein the Fc variant comprises the amino acid sequence of SEQ ID NO:42.

5. The humanized anti-CD137 antibody of claim 4, wherein the heavy chain comprises the amino acid sequence of SEQ ID NO:6.

6. The humanized anti-CD137 antibody of claim 5, wherein the light chain comprises the amino acid sequence of SEQ ID NO:7.

7. A pharmaceutical composition, comprising the humanized anti-CD137 antibody of claim 1 and a pharmaceutically acceptable carrier.

8. The pharmaceutical composition of claim 7, wherein the humanized anti-CD137 antibody comprises a heavy chain comprising the amino acid sequence of SEQ ID NO:6 and a light chain comprising the amino acid sequence of SEQ ID NO:7.

9. A method of treating cancer in a subject, comprising administering to the subject in need thereof an effective amount of the pharmaceutical compositions of claim 7, wherein the cancer is colon cancer or melanoma.

10. The method of claim 9, wherein the pharmaceutical composition comprises the humanized anti-CD137 antibody, which comprises a heavy chain comprising the amino acid sequence of SEQ ID NO:6 and a light chain comprising the amino acid sequence of SEQ ID NO:7.

11. The method of claim 10, further comprising administering to the subject an immunomodulatory agent.

12. The method of claim 11, wherein the immunomodulatory agent is a checkpoint inhibitor.

13. The method of claim 12, wherein the checkpoint inhibitor is an anti-PD-1 antibody.

14. The method of claim 13, wherein the anti-PD-1 antibody is pembrolizumab, SSI-361, nivolumab, avelumab, durvalumab, or atezolizumab.

15. The method of claim 9, wherein the human patient has an advanced cancer, a metastatic cancer, or an unresectable malignancy.

16. The method of claim 10, wherein the pharmaceutical composition comprising the humanized anti-CD137 antibody is administered to the human patient at a dose of 0.3 to 10 mg/kg.

17. The method of claim 16, wherein the pharmaceutical composition comprising the humanized anti-CD137 antibody is administered to the human patient once every 2-4 weeks.

* * * * *

SEQUENCE LISTING

```
<160> NUMBER OF SEQ ID NOS: 45

<210> SEQ ID NO 1
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 1

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ala Gly Phe
            20                  25                  30

Glu Met His Trp Ile Lys Gln Thr Pro Val His Gly Leu Gly Trp Ile
        35                  40                  45

Gly Ala Ile Asp Pro Lys Thr Gly Gly Thr Asp Tyr Asn Gln Lys Phe
    50                  55                  60

Lys Asp Lys Ala Leu Leu Thr Ala Asp Lys Ser Ser Asn Thr Ala Tyr
65                  70                  75                  80

Met Glu Leu Arg Ser Leu Thr Ser Glu Asp Ser Ala Val Tyr Tyr Cys
                85                  90                  95

Thr Arg Asp Leu Gly Tyr Phe Asp Val Trp Gly Thr Gly Thr Thr Val
            100                 105                 110

Thr Val Ser Ser
        115

<210> SEQ ID NO 2
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 2

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Ser Asn
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Ser Glu Lys Leu Pro Arg
```

```
                    85                  90                  95

Thr Phe Gly Gly Gly Thr Lys Leu Glu Ile Arg Arg
                100                 105

<210> SEQ ID NO 3
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Gly Phe
            20                  25                  30

Glu Met His Trp Val Arg Gln Ala Pro Gly Gln Gly Leu Glu Trp Met
        35                  40                  45

Gly Ala Ile Asp Pro Lys Thr Gly Gly Thr Asp Tyr Asn Gln Lys Phe
    50                  55                  60

Lys Asp Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Gly Tyr Phe Asp Val Trp Gly Gln Gly Thr Leu Val
                100                 105                 110

Thr Val Ser Ser
            115

<210> SEQ ID NO 4
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Asn
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Lys Leu Pro Arg
                85                  90                  95

Thr Phe Gly Gly Gly Thr Lys Val Glu Ile Arg Arg
                100                 105

<210> SEQ ID NO 5
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 5
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Asn
            20                  25                  30

Leu Asn Trp Tyr Gln Lys Pro Gly Gly Ala Val Lys Leu Leu Ile
                35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65              70                  75                  80

Glu Asp Phe Ala Thr Tyr Phe Cys Gln Gln Ser Glu Lys Leu Pro Arg
                85                  90                  95

Thr Phe Gly Gly Gly Thr Lys Val Glu Ile Arg Arg
                100                 105
```

<210> SEQ ID NO 6
<211> LENGTH: 445
<212> TYPE: PRT
<213> ORGANISM: Artificial Sequence
<220> FEATURE:
<223> OTHER INFORMATION: Synthetic Polypeptide

<400> SEQUENCE: 6

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Gly Phe
            20                  25                  30

Glu Met His Trp Val Arg Gln Ala Pro Gly Gln Gly Leu Glu Trp Met
                35                  40                  45

Gly Ala Ile Asp Pro Lys Thr Gly Gly Thr Asp Tyr Asn Gln Lys Phe
    50                  55                  60

Lys Asp Arg Val Thr Met Thr Arg Asp Thr Ser Ile Ser Thr Ala Tyr
65              70                  75                  80

Met Glu Leu Ser Arg Leu Arg Ser Asp Thr Ala Val Tyr Tyr Cys
                85                  90                  95

Ala Arg Asp Leu Gly Tyr Phe Asp Val Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Val Glu Pro Lys Ser Cys Asp Lys Thr His Thr
    210                 215                 220

Cys Pro Pro Cys Pro Ala Pro Glu Leu Leu Gly Pro Ser Val Phe Leu
225                 230                 235                 240

Phe Pro Pro Lys Pro Lys Asp Thr Leu Met Ile Ser Arg Thr Pro Glu
                245                 250                 255
```

Val Thr Cys Val Val Asp Val Glu His Glu Asp Pro Glu Val Lys
          260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 7
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Asn
            20                  25                  30

Leu Asn Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Ser Glu Lys Leu Pro Arg
                85                  90                  95

Thr Phe Gly Gly Gly Thr Lys Val Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 8

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Ala Gly Phe
            20                  25                  30

Glu Met His Trp Val Arg Gln Ala Pro Gly Gln Gly Leu Gly Trp Met
        35                  40                  45

Gly Ala Ile Asp Pro Lys Thr Gly Gly Thr Asp Tyr Asn Gln Lys Phe
    50                  55                  60

Lys Asp Arg Val Thr Met Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Asp Leu Gly Tyr Phe Asp Val Trp Gly Gln Gly Thr Leu Val
            100                 105                 110

Thr Val Ser Ser
        115

<210> SEQ ID NO 9
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 9

Gln Val Gln Leu Val Gln Ser Gly Ala Glu Val Val Lys Pro Gly Ala
1               5                   10                  15

Ser Val Lys Leu Ser Cys Lys Ala Ser Gly Tyr Thr Phe Ala Gly Phe
            20                  25                  30

Glu Met His Trp Ile Arg Gln Ala Pro Gly Gln Gly Leu Gly Trp Ile
        35                  40                  45

Gly Ala Ile Asp Pro Lys Thr Gly Gly Thr Asp Tyr Asn Gln Lys Phe
    50                  55                  60

Lys Asp Arg Ala Thr Leu Thr Ala Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Asp Leu Gly Tyr Phe Asp Val Trp Gly Gln Gly Thr Leu Val
            100                 105                 110

Thr Val Ser Ser
        115
```

-continued

```
<210> SEQ ID NO 10
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 10
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Ser Asn
            20                  25                  30

Leu Asn Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Ser Glu Lys Leu Pro Arg
                85                  90                  95

Thr Phe Gly Gly Gly Thr Lys Leu Glu Ile Arg Arg
            100                 105

```
<210> SEQ ID NO 11
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 11
```

Gln Val Gln Leu Gln Gln Ser Gly Ala Glu Leu Val Arg Pro Gly Ala
1               5                   10                  15

Ser Val Thr Leu Ser Cys Lys Ala Ser
            20                  25

```
<210> SEQ ID NO 12
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 12
```

Gly Tyr Thr Phe Ala Gly Phe Glu Met His
1               5                   10

```
<210> SEQ ID NO 13
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 13
```

Trp Ile Lys Gln Thr Pro Val His Gly Leu Gly Trp Ile Gly
1               5                   10

```
<210> SEQ ID NO 14
<211> LENGTH: 17
<212> TYPE: PRT
<213> ORGANISM: Artificial Sequence
<220> FEATURE:
<223> OTHER INFORMATION: Synthetic Polypeptide
```

<400> SEQUENCE: 14

Ala Ile Asp Pro Lys Thr Gly Gly Thr Asp Tyr Asn Gln Lys Phe Lys
1               5                   10                  15

Asp

<210> SEQ ID NO 15
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 15

Lys Ala Leu Leu Thr Ala Asp Lys Ser Ser Asn Thr Ala Tyr Met Glu
1               5                   10                  15

Leu Arg Ser Leu Thr Ser Glu Asp Ser Ala Val Tyr Tyr Cys Thr Arg
            20                  25                  30

<210> SEQ ID NO 16
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 16

Asp Leu Gly Tyr Phe Asp Val
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 17

Trp Gly Thr Gly Thr Thr Val Thr Val Ser Ser
1               5                   10

<210> SEQ ID NO 18
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 19
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 19

Val Arg Gln Ala Pro Gly Gln Gly Leu Glu Trp Met Gly
1               5                   10

```
<210> SEQ ID NO 20
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 20

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 21
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 21

Trp Gly Gln Gly Thr Leu Val Thr Val Ser Ser
1               5                   10

<210> SEQ ID NO 22
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 22

Gln Val Gln Leu Val Gln Ser Gly Ala Glu Val Val Lys Pro Gly Ala
1               5                   10                  15

Ser Val Lys Val Ser Cys Lys Ala Ser
            20                  25

<210> SEQ ID NO 23
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 23

Val Arg Gln Ala Pro Gly Gln Gly Leu Gly Trp Met Gly
1               5                   10

<210> SEQ ID NO 24
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 24

Arg Val Thr Met Thr Ala Asp Thr Ser Ile Ser Thr Ala Tyr Met Glu
1               5                   10                  15

Leu Ser Arg Leu Arg Ser Asp Asp Thr Ala Val Tyr Tyr Cys Thr Arg
            20                  25                  30

<210> SEQ ID NO 25
<211> LENGTH: 25
<212> TYPE: PRT
<213> ORGANISM: Artificial Sequence
```

<220> FEATURE:
<223> OTHER INFORMATION: Synthetic Polypeptide

<400> SEQUENCE: 25

Gln Val Gln Leu Val Gln Ser Gly Ala Glu Val Val Lys Pro Gly Ala
1               5                   10                  15
Ser Val Lys Leu Ser Cys Lys Ala Ser
            20                  25

<210> SEQ ID NO 26
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 26

Ile Arg Gln Ala Pro Gly Gln Gly Leu Gly Trp Ile Gly
1               5                   10

<210> SEQ ID NO 27
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 27

Arg Ala Thr Leu Thr Ala Asp Thr Ser Ile Ser Thr Ala Tyr Met Glu
1               5                   10                  15
Leu Ser Arg Leu Arg Ser Asp Asp Thr Ala Val Tyr Tyr Cys Thr Arg
            20                  25                  30

<210> SEQ ID NO 28
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 28

Asp Ile Gln Met Thr Gln Thr Thr Ser Ser Leu Ser Ala Ser Leu Gly
1               5                   10                  15
Asp Arg Val Thr Ile Ser Cys
            20

<210> SEQ ID NO 29
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 29

Arg Ala Ser Gln Asp Ile Arg Ser Asn Leu Asn
1               5                   10

<210> SEQ ID NO 30
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 30

Trp Tyr Gln Gln Lys Pro Asp Gly Thr Val Lys Leu Leu Ile Tyr
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 31

Tyr Thr Ser Arg Leu His Ser
1               5

<210> SEQ ID NO 32
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 32

Gly Val Pro Ser Arg Phe Ser Gly Ser Gly Ser Gly Thr Asp Tyr Ser
1               5                   10                  15

Leu Thr Ile Ser Asn Leu Glu Gln Glu Asp Ile Ala Thr Tyr Phe Cys
            20                  25                  30

<210> SEQ ID NO 33
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 33

Gln Gln Ser Glu Lys Leu Pro Arg Thr
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 34

Phe Gly Gly Gly Thr Lys Leu Glu Ile Arg
1               5                   10

<210> SEQ ID NO 35
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 36
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 36

Trp Tyr Gln Gln Lys Pro Gly Lys Ala Pro Lys Leu Leu Ile Tyr
1               5                   10                  15

<210> SEQ ID NO 37
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 37

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 38
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 38

Phe Gly Gly Gly Thr Lys Val Glu Ile Arg Arg
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 39

Trp Tyr Gln Gln Lys Pro Gly Gly Ala Val Lys Leu Leu Ile Tyr
1               5                   10                  15

<210> SEQ ID NO 40
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 40

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Phe Cys
            20                  25                  30

<210> SEQ ID NO 41
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 41

Phe Gly Gly Gly Thr Lys Leu Glu Ile Arg Arg
1               5                   10

<210> SEQ ID NO 42
<211> LENGTH: 329
<212> TYPE: PRT
<213> ORGANISM: Artificial Sequence
<220> FEATURE:
<223> OTHER INFORMATION: Synthetic Polypeptide

<400> SEQUENCE: 42

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Glu His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 43
<211> LENGTH: 118
<212> TYPE: PRT
<213> ORGANISM: Artificial Sequence
<220> FEATURE:

<223> OTHER INFORMATION: Synthetic Polypeptide

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Thr Thr Gly Thr Thr Tyr Phe Asp Tyr Trp Gly Gln Gly Thr
            100                 105                 110

Leu Val Thr Val Ser Ser
        115

<210> SEQ ID NO 44
<211> LENGTH: 107
<212> TYPE: PRT
<213> ORGANISM: Artificial Sequence
<220> FEATURE:
<223> OTHER INFORMATION: Synthetic Polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Arg
            100                 105

<210> SEQ ID NO 45
<211> LENGTH: 231
<212> TYPE: PRT
<213> ORGANISM: Artificial Sequence
<220> FEATURE:
<223> OTHER INFORMATION: Synthetic Polypeptide

<400> SEQUENCE: 45

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Asn Pro Asp Gly Thr Val Lys Leu Leu Ile
        35                  40                  45

Tyr Tyr Thr Ser Asn Leu His Ser Glu Val Pro Ser Arg Phe Ser Gly

```
                50                  55                  60
Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Asp Phe Thr Leu Pro Phe
                 85                  90                  95

Thr Phe Gly Gly Gly Thr Lys Leu Glu Ile Arg Arg Ala Gln Val Gln
                100                 105                 110

Leu Gln Gln Pro Gly Ala Glu Leu Val Lys Pro Gly Ala Ser Val Arg
            115                 120                 125

Met Ser Cys Lys Ala Ser Gly Tyr Thr Phe Thr Asn Tyr Asn Met Tyr
            130                 135                 140

Trp Val Lys Gln Ser Pro Gly Gln Gly Leu Glu Trp Ile Gly Ile Phe
145                 150                 155                 160

Tyr Pro Gly Asn Gly Asp Thr Ser Tyr Asn Gln Lys Phe Lys Asp Lys
                165                 170                 175

Ala Thr Leu Thr Ala Asp Lys Ser Ser Asn Thr Ala Tyr Met Gln Leu
            180                 185                 190

Ser Ser Leu Thr Ser Glu Asp Ser Ala Val Tyr Tyr Cys Ala Arg Ser
            195                 200                 205

Gly Gly Ser Tyr Arg Tyr Asp Gly Gly Phe Asp Tyr Trp Gly Gln Gly
            210                 215                 220

Thr Thr Leu Thr Val Ser Ser
225                 230
```